US011434490B2

(12) United States Patent
Ryckelynck et al.

(10) Patent No.: US 11,434,490 B2
(45) Date of Patent: Sep. 6, 2022

(54) FLUOROGEN-BINDING RNA APTAMERS

(71) Applicants: CENTRE NATIONAL DE LA RECHERCHE SCIENTIFIQUE, Paris (FR); UNIVERSITÉ DE STRASBOURG, Strasbourg (FR); SIMON FRASER UNIVERSITY, Burnaby (CA); THE UNITED STATES OF AMERICA, AS REPRESENTED BY THE SECRETARY, DEPARTMENT OF HEALTH AND HUMAN SERVICES, Rockville, MD (US)

(72) Inventors: Michael Ryckelynck, Strasbourg (FR); Alexis Autour, Strasbourg (FR); Peter Unrau, North Vancouver (CA); Elena Dolgosheina, Vancouver (CA); Sunny Chiu Yuk Jeng, Vancouver (CA); Shanker Shyam Sundhar Panchapakesan, North Madavilagam (IN); Amir Abdolahzadeh, Maple Ridge (CA); Razvan Cojocaru, Port Coquitlam (CA); Adrian Ferré D'Amaré, Rockville, MD (US); Robert Trachman, Rockville, MD (US)

(73) Assignees: Centre National De La Recherche, Paris (FR); Scientifique Université De Strasbourg, Strasbourg (FR); Simon Fraser University, Burnaby (CA); The United States of America, As Represented by The Secretary, Department of Health and Human Services, Rockville, MD (US)

( * ) Notice: Subject to any disclaimer, the term of this patent is extended or adjusted under 35 U.S.C. 154(b) by 124 days.

(21) Appl. No.: 16/608,127

(22) PCT Filed: Apr. 23, 2018

(86) PCT No.: PCT/IB2018/052808
§ 371 (c)(1),
(2) Date: Oct. 24, 2019

(87) PCT Pub. No.: WO2018/198013
PCT Pub. Date: Nov. 1, 2018

(65) Prior Publication Data
US 2020/0181618 A1 Jun. 11, 2020

Related U.S. Application Data

(60) Provisional application No. 62/489,346, filed on Apr. 24, 2017.

(51) Int. Cl.
*C12N 15/115* (2010.01)
*C12Q 1/68* (2018.01)

(52) U.S. Cl.
CPC ........ *C12N 15/115* (2013.01); *C12N 2310/16* (2013.01); *C12N 2320/10* (2013.01)

(58) Field of Classification Search
None
See application file for complete search history.

(56) References Cited

FOREIGN PATENT DOCUMENTS

WO 2013016694 1/2013

OTHER PUBLICATIONS

International Search Report and Written Opinion dated Jul. 5, 2018 in Application No. PCT/IB2018/052808.
Lawrence et al., "Shape Complementarity at Protein/ Protein Interfaces," J. Mol. Biol., 234, pp. 346-950.
Lorsch et al., "In Vitro Selection of RNA Aptamers Specific for Cyanocobalamin," Biochemistry, 33, pp. 973-982 (1994).
Leontis et al., "Geometric Nomenclature and Classification of RNA Base Pairs," RNA, 7, pp. 499-512 (2001).
Phan et al., "Small-Molecule Interaction with a Five-Guanine-Tract G-Quadruplex Structure from the Human MYC Promoter," Nature Chemical Biology, 1, pp. 167-173 (2005).
Shaner et al., "A Guide to Choosing Fluorescent Proteins," Nature Methods, 2, pp. 905-909 (2005).
Jarikote et al., "Exploring Base-Pair-Specific Optical Properties of the DNA Stain Thiazole Orange," Chem. Eur. J., 13, pp. 300-310 (2007).
McCoy et al., "Phaser Crystallographic Software," J. Appl. Cryst., 40, pp. 658-674 (2007).
Adams et al., "PHENIX: a comprehensive Python-Based System for Macromolecular Structure Solution," Acta Cryst., D66, pp. 213-221 (2010).
Emsley et al., "Features and Development of Coot," Acta Cryst., D66, pp. 486-501 (2010).
Kabsch, "XDS," Acta Cryst., D66, pp. 125-132 (2010).
Paige et al., "RNA Mimics of Green Fluorescent Protein," Science, 333, pp. 642-646 (2011).
Smirnov et al., "Biological Significance of 5S rRNA Import Into Human Mitochondria: Role of Ribosomal Protein MRP-L18," Genes & Development, 25, pp. 1289-1305 (2011).

(Continued)

*Primary Examiner* — Sean McGarry
(74) *Attorney, Agent, or Firm* — Snell & Wilmer L.L.P.

(57) ABSTRACT

RNA aptamers are disclosed with distinct fluorescent properties, fluorophore binding affinities, and salt dependence. Also disclosed are corresponding fluorophores, with selected fluorophores evidencing high cellular permeability. The aptamer's high fluorophore affinities, the high brightness of the bound complexes, and their thermal and salt stability, provide distinct aspects of the disclosed aptamers.

17 Claims, 40 Drawing Sheets
Specification includes a Sequence Listing.

(56) References Cited

OTHER PUBLICATIONS

Nicoludis et al., "Optimized End-Stacking Provides Specificity of N-Methyl Mesoporphyrin IX for Human Telomeric G-Quadruplex DNA," J. Am. Chem. Soc., 134, pp. 20446-20456 (2012).

Dolgosheina et al., "RNA Mango Aptamer-Fluorophore: A Bright, High-Affinity Complex for RNA Labeling and Tracking," ACS Chemical Biology, dx.doi.org/10.1021/cb500499x (2014).

Huang et al., "A G-Quadruplex-Containing RNA Activates Fluorescence in a GFP-Like Fluorophore," Nature Chemical Biology, 10, pp. 686-691 (2014).

Karunatilaka et al., "Post-transcriptional Modifications Modulate Conformational Dynamics in Human U2-U6 snRNA Complex," RNA, 20, pp. 16-23 (date unknown).

Warner et al., "Structural Basis for Activity of Highly Efficient RNA Mimics of Green Fluorescent Protein," Nature Structural & Molecular Biology, 8, pp. 658-663 (2014).

Filonov et al., "In-Gel Imaging of RNA Processing Using Broccoli Reveals Optimal Aptamer Expression Strategies," Chemistry & Biology, 22, pp. 649-660 (2015).

Ryckelynck et al., "Using Droplet-Based Microfluidics to Improve the Catalytic Properties of RNA Under Multiple-Turnover Conditions," RNA, 21, pp. 458-469 (not dated).

Autour et al., "iSpinach: a Fluorogenic RNA Aptamer Optimized for in Vitro Applications," Nucleic Acids Research, 44, pp. 2491-2500 (2016).

Dolgosheina et al., "Fluorophore-Binding RN Aaptamers and Their Applications," WIREs RNA, doi: 10.1002/wrna.1383 (2016).

Jeng et al., "Fluorophore Ligand Binding and Complex Stabilization of the RNA Mango and RNA Spinach Aptamers," RNA, 22, pp. 1884-1892 (not dated).

Rodriguez et al., "The Growing and Glowing Toolbox of Fluorescent and Photoactive Proteins," Trends in Biochemical Sciences, 42, 111-129 (2017).

Tan et al., "Fluoromodules Consisting of a Promiscuous RNA Aptamer and Red or Blue Fluorogenic Cyanine Dyes: Selection, Characterization, and Bioimaging," J. Am. Chem. Soc., DOI: 10.1021/jacs.7b04211 (2017).

Trachman III et al., "Structural basis for High-Affinity Fluorophore Binding and Activation by RNA Mango," Nature Chemical Biology (2017).

Trachman III et al., "Structural Principles of Fluorescent RNA Aptamers," Trends in Pharmacological Sciences, http://dx.doi.org/10.1016/j.tips.2017.06.007 (2017).

Autour et al., "Fluorogenic RNA Mango Aptamers for Imaging Small Non-Coding RNAs in Mammalian Cells," Nature Communications, 9, 656 (2018).

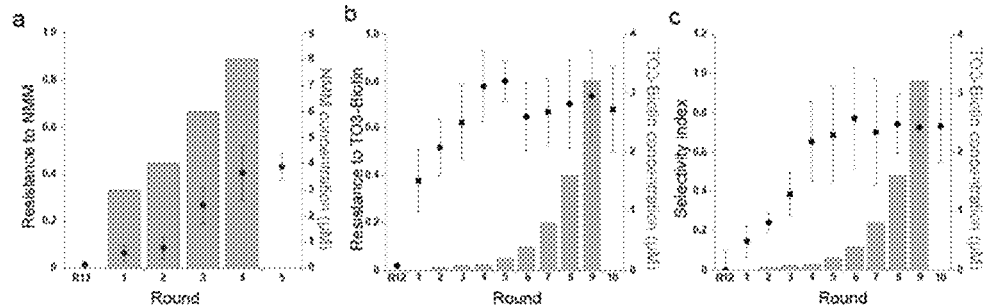
Figure 6
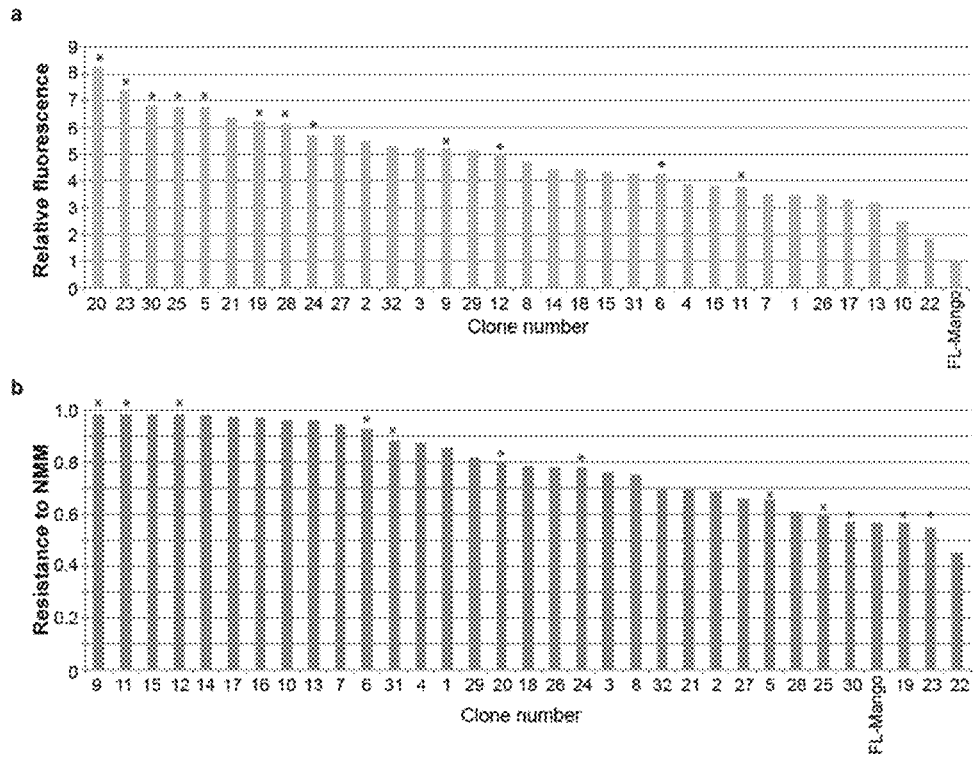
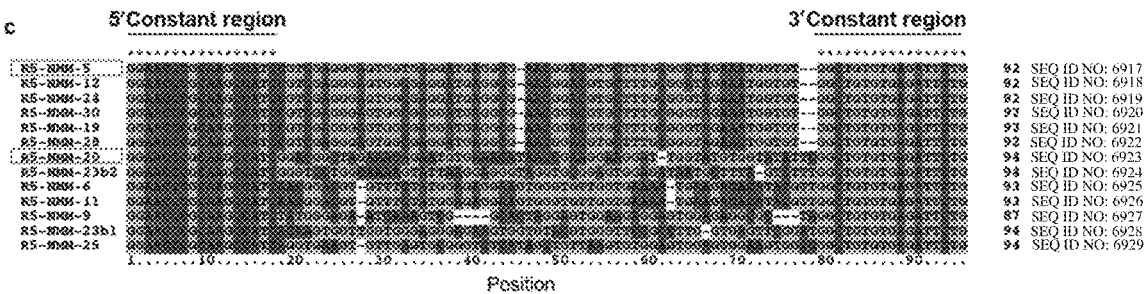
Figure 7

|  |  | Rel. F$_c$ | K$_D$ |  |
|---|---|---|---|---|
| R2-1 (full-length) | ...GTGCGTACC-GAA-GG-AGA-GG-AGA-GG-AAGA-GG-AGA-GTGCGCGTGTTG... | 1.0 ± 0.2 | 0.6 ± 0.1 | SEQ ID NO: 7005 |
| Mango II | GGCACGTAC-GAA-GG-AGA-GG-AGA-GG-AAGA-GG-AGA-GTACGTGC | 1.0 ± 0.2 | 0.3 ± 0.1 | SEQ ID NO: 7006 |
| Variant 1 | GGCACGTAC-GAA-GG-AGA-GG-TGC-GG---AGA-GG-AGA-GTACGTGC | 0.9 ± 0.2 | 3.5 ± 0.3 | SEQ ID NO: 7007 |
| Variant 2 | GGCACGTAC-GAA-GG-GAC-GG-AGA-GG---AGA-GG-AGA-GTACGTGC | 0.7 ± 0.1 | 7.1 ± 0.4 | SEQ ID NO: 7008 |
| Variant 3 | GGCACGTAC-GAA-GG-GAC-GG-TGC-GG-AAGA-GG-AGA-GTACGTGC | 1.1 ± 0.2 | 8.2 ± 1.7 | SEQ ID NO: 7009 |
| Variant 4 | GGCACGTAC-GAA-GG-AGA-GG-AGA-GG---AGA-GG-AGA-GTACGTGC | 0.7 ± 0.4 | 4.7 ± 0.8 | SEQ ID NO: 7010 |
| Variant 5 | GGCACGTAC-GAA-GG-AGA-GG-TGC-GG-AAGA-GG-AGA-GTACGTGC | 0.9 ± 0.2 | 0.9 ± 0.1 | SEQ ID NO: 7011 |
| Variant 6 | GGCACGTAC-GAA-GG-GAC-AGA-GG-AAGA-GG-AGA-GTACGTGC | 1.1 ± 0.1 | 12 ± 1 | SEQ ID NO: 7012 |
| Variant 7 | GGCACGTAC-GAA-GG-AGA-GG-AGA-GG-ATGA-GG-AGA-GTACGTGC | 0.9 ± 0.2 | 2.5 ± 0.3 | SEQ ID NO: 7013 |

Figure 9A

|  |  | Rel. F$_c$ | K$_D$ |  |
|---|---|---|---|---|
| R5-NMM-5 (full-length) | ...ACCCGCAAGCCATCCGT-CGA-GG-GAGT-GG-TGA-GG-ATGA-GG-CGA-ACGGACGTGCTTTG... | 1.0 ± 0.2 | 10 ± 1 | SEQ ID NO: 7014 |
| Mango IV | ------GGCACGTAC-CGA-GG-GAGT-GG-TGA-GG-ATGA-GG-CGA-GTACGTGC | 1.0 ± 0.2 | 13 ± 1 | SEQ ID NO: 7015 |
| Variant 1 | ---------------GG-GAGT-GG-TGA-GG-ATGA-GG-CGA-ACGGACGTGCTTTG... | 0.3 ± 0.1 | 78 ± 6 | SEQ ID NO: 7016 |
| Variant 2 | ---------------------------------------GGCGGACGTGCTTTG... | u.d. | u.d. | SEQ ID NO: 7017 |
| Variant 3 | GGCCGCAAGCCATCCGT-CGA-GG-GAGT-GG-TGA-GG-ATGA-GG-CGA-ACGGACGTGCTTTG... | 0.9 ± 0.1 | 28 ± 2 | SEQ ID NO: 7018 |
| Variant 4 | ------GGAAGCCTCCGT-CGA-GG-GAGT-GG-TGA-GG-ATGA-GG-CGA-ACGGAGTGCTT | 0.3 ± 0.2 | 7 ± 1 | SEQ ID NO: 7019 |
| Variant 5 | ------GGACGTACT-CGA-GG-GAGT-GG-TGA-GG-ATGA-GG-CGA-AGTACGT | 1.0 ± 0.2 | 7 ± 2 | SEQ ID NO: 7020 |
| Variant 6 | ---------GGCACGTA-CGA-GG-GAGT-GG-TGA-GG-ATGA-GG-CGA-GTACGTGC | 0.5 ± 0.1 | 18 ± 10 | SEQ ID NO: 7021 |
| Variant 7 | ---------GGCACGTAC-CAG-GG---AGT-GG-TGA-GG-ATGA-GG-CG--GTACGTGC | 0.8 ± 0.2 | 10 ± 3 | SEQ ID NO: 7022 |
| Variant 8 | ---------GGCACGTAC-GAA-GG-GAGT-GG-TGA-GG-ATGA-GG-AGA-GTACGTGC | 0.6 ± 0.1 | 20 ± 1 | SEQ ID NO: 7023 |
| Variant 9 | ---------GGCACGTAC-CGA-GG-GAC---GG-TGA-GG-ATGA-GG-CGA-GTACGTGC | 0.2 ± 0.1 | 260 ± 20 | SEQ ID NO: 7024 |
| Variant 10 | ---------GGCACGTAC-CGA-GG-GAGT-GG-TGC-GG-ATGA-GG-CGA-GTACGTGC | 0.9 ± 0.2 | 10 ± 1 | SEQ ID NO: 7025 |
| Variant 11 | ---------GGCACGTAC-CGA-GG-GAGT-GG-A--GA-GG-CGA-GTACGTGC | 0.5 ± 0.1 | 7 ± 1 | SEQ ID NO: 7026 |
| Variant 12 | ---------GGCACGTAC-CGA-GG-AAGT-GG-TGA-GG-ATGA-GG-CGA-GTACGTGC | 0.4 ± 0.1 | 70 ± 30 | SEQ ID NO: 7027 |
| Variant 13 | ---------GGCACGTAC-CGA-GG---AGT-GG-TGA-GG-ATGA-GG-CGA-GTACGTGC | 0.4 ± 0.1 | 6 ± 1 | SEQ ID NO: 7028 |
| Variant 14 | ---------GGCACGTAC-CGA-GG-GAAT-GG-TGA-GG-ATGA-GG-CGA-GTACGTGC | 0.3 ± 0.1 | 300 ± 30 | SEQ ID NO: 7029 |
| Variant 15 | ---------GGCACGTAC-CGA-GG-GA-T-GG-TGA-GG-ATGA-GG-CGA-GTACGTGC | 0.2 ± 0.1 | 140 ± 20 | SEQ ID NO: 7030 |
| Variant 16 | ---------GGCACGTAC-CGA-GG---AGA-GG-TGA-GG-ATGA-GG-CGA-GTACGTGC | 0.7 ± 0.2 | 7 ± 1 | SEQ ID NO: 7031 |
| Variant 17 | ---------GGCACGTAC-CGA-GG-GAGT-GG-TGA-GG-AAGA-GG-CGA-GTACGTGC | 0.6 ± 0.1 | 40 ± 2 | SEQ ID NO: 7032 |
| Variant 18 | ---------GGCACGTAC-CGA-GG-GAGT-GG-TGA-GG-ATGA-GG-AGA-GTACGTGC | 0.6 ± 0.1 | 26 ± 1 | SEQ ID NO: 7033 |
| Variant 19 | ---------GGCACGTAC-CGA-GG-GAGT-GG-TGA-GG-ATGA-GG-CAA-GTACGTGC | 0.8 ± 0.2 | 26 ± 4 | SEQ ID NO: 7034 |
| Variant 20 | ---------GGCACGTAC-GAA-GG-GAGT-GG-TGA-GG-ATGA-GG-CGA-GTACGTGC | 0.7 ± 0.1 | 40 ± 2 | SEQ ID NO: 7035 |

Figure 9B

|  |  | Rel. F$_c$ | K$_D$ |  |
|---|---|---|---|---|
| R5-NMM-28 (full-length) | ...GTGAAACATAACC-GAA-GG-AA-GG-ATT-GG-TATGT-GG-TATATTC-GGCTGTGTGAGATTCTG | 1.0 ± 0.1 | 14 ± 1 | SEQ ID NO: 7036 |
| Mango III | ----GGCACGTAC-GAA-GG-AA-GG-ATT-GG-TATGT-GG-TATATTC-GTACGTGCC | 1.0 ± 0.1 | 7.3 ± 0.4 | SEQ ID NO: 7037 |
| Variant 1 | ...GTGAAACATAACC-GAA-GG-AA-GG-ATT-GG-TATGT-GG-TATATTC-GGCTGTGTGAGATTCT | 0.9 ± 0.1 | 35 ± 2 | SEQ ID NO: 7038 |
| Variant 2 | ...GTGAAACATAACC-GAA-GG-AA-GG-ATT-GG-TATGT-GG-TATATTC-GGCTGTGTG | 0.6 ± 0.1 | 140 ± 8 | SEQ ID NO: 7039 |
| Variant 3 | GTGAAACATAACC-GAA-GG-AA-GG-ATT-GG-TATGT-GG-TATATTC-GGCTGTGTGAGATTCTG | 0.9 ± 0.1 | 170 ± 6 | SEQ ID NO: 7040 |
| Variant 4 | ---------GG-GAA-GG-AA-GG-ATT-GG-TATGT-GG-TATATTC-GGCTGTGTGAGATTCTG | 1.0 ± 0.1 | 15 ± 1 | SEQ ID NO: 7041 |
| Variant 5 | GTGAAACATAACC-GAA-GG-AA-GG-ATT-GG-TATGT-GG-TATATTC-GGCTGTGTG | 1.0 ± 0.1 | 12 ± 1 | SEQ ID NO: 7042 |
| Variant 6 | GTGAAACATAACC-GAA-GG-AA-GG-ATT-GG-TATGT-GG-TATATTC-GGCTGTGTG | 1.1 ± 0.1 | 52 ± 3 | SEQ ID NO: 7043 |
| Variant 7 | ---GGACATAACC-GAA-GG-AA-GG-ATT-GG-TATGT-GG-TATATTC-GGCTGTGTGAGATTCTG | 1.1 ± 0.1 | 12 ± 1 | SEQ ID NO: 7044 |
| Variant 8 | ----GGCACG-GAA-GG-AA-GG-ATT-GG-TATGT-GG-TATATTC-CGTGCC | 1.0 ± 0.1 | 5.6 ± 0.3 | SEQ ID NO: 7045 |
| Variant 9 | ----GGCACG-TAC-GG-AA-GG-ATT-GG-TATGT-GG-TATAGTA-CGTGCC | 1.0 ± 0.1 | 46 ± 3 | SEQ ID NO: 7046 |
| Variant 10 | ----GGCACG-GAA-GG-AA-GG-ATT-GG-TATGT-GG-TATA-----CGTGCC | u.d. | u.d. | SEQ ID NO: 7047 |
| Variant 11 | ----GGCACG------GG-AA-GG-ATT-GG-TATGT-GG-TATATTC-CGTGCC | u.d. | u.d. | SEQ ID NO: 7048 |

Figure 9C

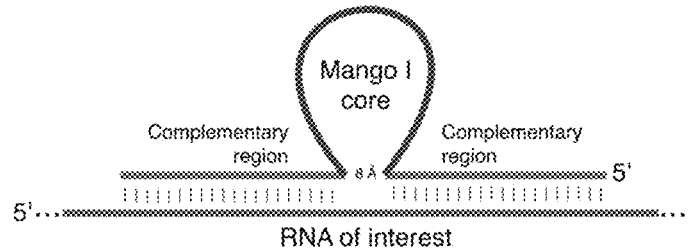

Figure 20

| Schematic | RFU | Schematic | RFU | Schematic | RFU | Schematic | RFU |
|---|---|---|---|---|---|---|---|
| SEQ ID NO: 7049 / SEQ ID NO: 7050 / SEQ ID NO: 7051 | 32 | SEQ ID NO: 7049 / SEQ ID NO: 7050 / SEQ ID NO: 7052 | 18 | SEQ ID NO: 7049 / SEQ ID NO: 7050 / SEQ ID NO: 7053 | 19 | SEQ ID NO: 7049 / SEQ ID NO: 7050 | 10 |
| SEQ ID NO: 7049 / SEQ ID NO: 7054 / SEQ ID NO: 7051 | 27 | SEQ ID NO: 7049 / SEQ ID NO: 7054 / SEQ ID NO: 7052 | 23 | SEQ ID NO: 7049 / SEQ ID NO: 7054 / SEQ ID NO: 7053 | 18 | SEQ ID NO: 7049 / SEQ ID NO: 7054 | 7 |
| SEQ ID NO: 7055 / SEQ ID NO: 7050 / SEQ ID NO: 7051 | 31 | SEQ ID NO: 7055 / SEQ ID NO: 7050 / SEQ ID NO: 7052 | 24 | SEQ ID NO: 7055 / SEQ ID NO: 7050 / SEQ ID NO: 7053 | 38 | SEQ ID NO: 7055 / SEQ ID NO: 7050 | 6 |
| SEQ ID NO: 7055 / SEQ ID NO: 7054 / SEQ ID NO: 7051 | 37 | SEQ ID NO: 7055 / SEQ ID NO: 7054 / SEQ ID NO: 7052 | 18 | SEQ ID NO: 7055 / SEQ ID NO: 7054 / SEQ ID NO: 7053 | 32 | SEQ ID NO: 7055 / SEQ ID NO: 7054 | 5 |
| SEQ ID NO: 7055 / SEQ ID NO: 7056 / SEQ ID NO: 7051 | 25 | SEQ ID NO: 7055 / SEQ ID NO: 7056 / SEQ ID NO: 7052 | 21 | SEQ ID NO: 7055 / SEQ ID NO: 7056 / SEQ ID NO: 7053 | 37 | SEQ ID NO: 7055 / SEQ ID NO: 7056 | 5 |
| SEQ ID NO: 7057 / SEQ ID NO: 7054 / SEQ ID NO: 7051 | 57 | SEQ ID NO: 7057 / SEQ ID NO: 7054 / SEQ ID NO: 7052 | 17 | SEQ ID NO: 7057 / SEQ ID NO: 7054 / SEQ ID NO: 7053 | 43 | SEQ ID NO: 7057 / SEQ ID NO: 7054 | 8 |
| SEQ ID NO: 7051 | 101 | SEQ ID NO: 7052 | 94 | SEQ ID NO: 7053 | 93 | | 100 |

Figure 21

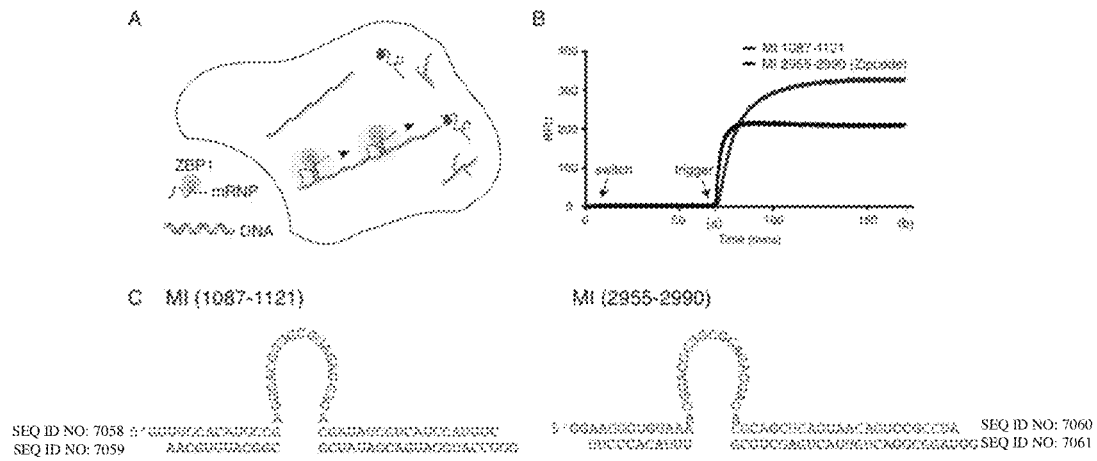
Figure 22
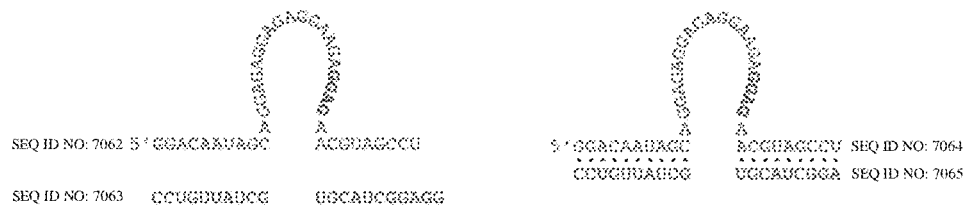
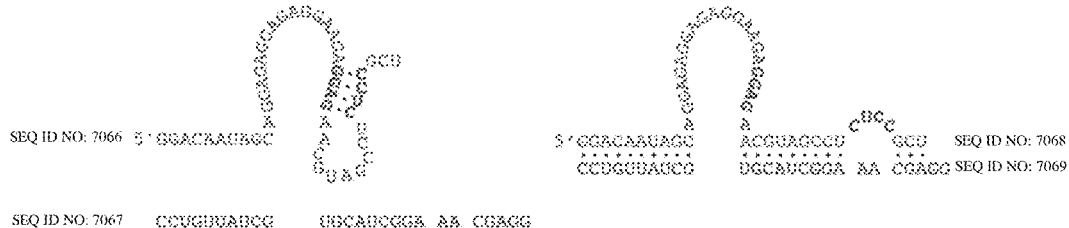
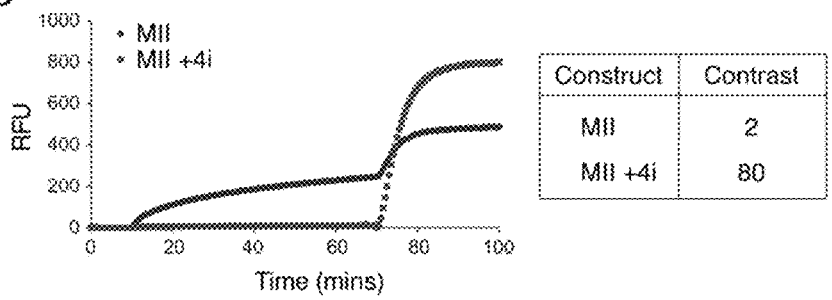
Figure 23

A

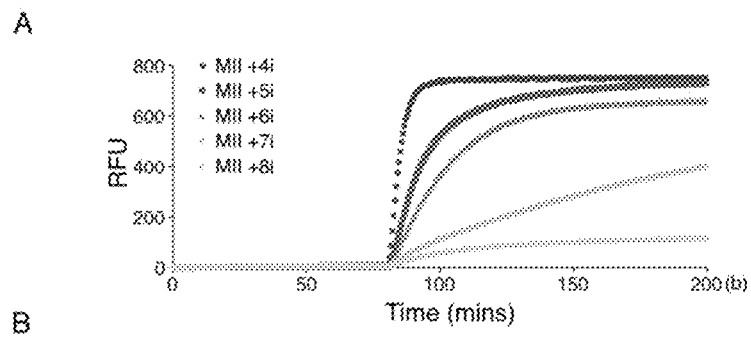

B

| Name | Mango II bipartite switch | Contrast | |
|---|---|---|---|
| MII +4i | ggacaatagca aggagaggacaggaagaggaga acgtagccta CUCC ccccc | 80 | SEQ ID NO: 7070 |
| MII +5i | ggacaatagca agcagaggacaggaaGAGGAGA acgtagccta CUCCU ccccc | 158 | SEQ ID NO: 7071 |
| MII +6i | ggacaatagca aggagaggacaggaAGAGGAGA acgtagccta CUCCUC ccccc | 150 | SEQ ID NO: 7072 |
| MII +7i | ggacaatagca aggagaggacaggaAGAGGAGA acgtagccta CUCCUCU ccccc | 80 | SEQ ID NO: 7073 |
| MII +8i | ggacaatagca aggagaggacaggaAGAGGAGA acgtagccta CUCCUCUU ccccc | 19 | SEQ ID NO: 7074 |

Figure 24

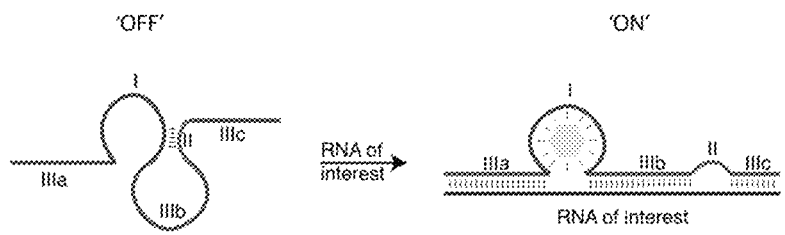

Figure 25

| Sequence Names | Piece 1 | |
|---|---|---|
| Consensus | GGACAATAGCA--GA-GGGAGTGGTGAGGATGAGG-CX--AACGTAGCCT | SEQ ID NO: 7075 |
| 12 Sequences | 10        20        30        40        50 | |
| MIV.1.seq | GGACAATAGCA-----GGGAGTGGTGAGGATGAGG-----AACGTAGCCT | SEQ ID NO: 7076 |
| MIV.2.seq | GGACAATAGCA---A-GGGAGTGGTGAGGATGAGG-----AACGTAGCCT | SEQ ID NO: 7077 |
| MIV.3.seq | GGACAATAGCA---GA-GGGAGTGGTGAGGATGAGG----AACGTAGCCT | SEQ ID NO: 7078 |
| MIV.4.seq | GGACAATAGCA---A-GGGAGTGGTGAGGATGAGG-C---AACGTAGCCT | SEQ ID NO: 7079 |
| MIV.5.seq | GGACAATAGCA---A-GGGAGTGGTGAGGATGAGG-CG--AACGTAGCCT | SEQ ID NO: 7080 |
| MIV.6.seq | GGACAATAGCA---A-GGGAGTGGTGAGGATGAGG-CGA-AACGTAGCCT | SEQ ID NO: 7081 |
| MIV.7.seq | GGACAATAGCA--GA-GGGAGTGGTGAGGATGAGG-C---AACGTAGCCT | SEQ ID NO: 7082 |
| MIV.8.seq | GGACAATAGCA--GA-GGGAGTGGTGAGGATGAGG-CG--AACGTAGCCT | SEQ ID NO: 7083 |
| MIV.9.seq | GGACAATAGCA--GA-GGGAGTGGTGAGGATGAGG-CGA-AACGTAGCCT | SEQ ID NO: 7084 |
| MIV.10.seq | GGACAATAGCA-CGA-GGGAGTGGTGAGGATGAGG-C---AACGTAGCCT | SEQ ID NO: 7085 |
| MIV.11.seq | GGACAATAGCA-CGA-GGGAGTGGTGAGGATGAGG-CG--AACGTAGCCT | SEQ ID NO: 7086 |
| MIV.12.seq | GGACAATAGCA-CGA-GGGAGTGGTGAGGATGAGG-CGA-AACGTAGCCT | SEQ ID NO: 7087 |

Figure 26

| Construct | Contrast |
|---|---|
| MIV.4 | 2.2120 |
| MIV.5 | 3.0303 |
| MIV.6 | 2.8747 |
| MIV.7 | 2.4497 |
| MIV.8 | 4.1781 |
| MIV.9 | 4.4402 |
| MIV.10 | 5.1584 |
| MIV.11 | 14.4080 |
| MIV.12 | 14.0661 |
| MIV | 1.5470 |

Figure 27

SEQ ID NO: 7088
MII.HBAZ1 targets mRNA in zipcode region 5' TAGGCGGACTATGACTTAGTTGCGTTACACCCTTTC 5'GG GAAAGGGTGTAA A GGAG A GGAG A GGAAGA GGAG A CGCAACTAAGTC CTCCT TCCGCCTA SEQ ID NO: 7089

3'   CTTTCCCACATT ------------------------- GCGTTGATTCAG ----- AGGCGGAT SEQ ID NO: 7090

SEQ ID NO: 7091
MII.HBA1 targets human beta actin 5' CGAGGCCCAGAGAGAGAGGCATCCTCACCCTGAAGT
SEQ ID NO: 7092
5'GG ACTTCAGGGTGA A GGAG A GGAG A GGAAGA GGAG A GGATGCCTCTCT CTCCT CTCTGGGCCTCG 3'   TGAAGTCCCACT ------------------------- CCTACGGAGAGA -AC-- GAGACCCGGAGC GG
SEQ ID NO: 7093

MII.HBA2 targets human beta actin 5' GGCACCCAGCACAATGAAGATCAAGATCATTG SEQ ID NO: 7094

5'GG CAATGATCTT A GGAG A GGAG A GGAAGA GGAG A GATCTTCATT CTCCT GTGCTGGGTG SEQ ID NO: 7095

3'   GTTACTAGAA --------------------------- CTAGAAGTAA ----- CACGACCCAC GG SEQ ID NO: 7096

MII.HBA3 targets human beta actin 5' AACTGGAACGGTGAAGGTGACAGCAGTCGG SEQ ID NO: 7097

5'GG CCGACTGCTG A GGAG A GGAG A GGAAG A GGAG A TCACCTTCAC CTCCT CGTTCCAGTT SEQ ID NO: 7098

3'   GGCTGACGAC ---------------------------- AGTGGAAGTG ------ GCAAGGTCAA GG SEQ ID NO: 7099

MI.B2 (targets mouse beta actin mRNA 1087 - 1121) sequence conserved in humans
5'GG UUGCACAUGCCG A GGGACGGUGCGGAGAGGAG A GAGCCGUUGU CUCC ACGACCAGCGC SEQ ID NO: 7100
3'   ...AACGUGUACGGC ------------------------ CUCGGCAACA -GC- UGCUGGUCGCG... SEQ ID NO: 7101

MII.B2 (targets mouse beta actin mRNA 1087 - 1121) sequence conserved in humans
5'GG UUGCACAUGCCG A GGAGAGGAGAGGAAGAGGAG A GAGCCGUUGU CUCCU ACGACCAGCGC SEQ ID NO: 7102
3'   ...AACGUGUACGGC ------------------------- CUCGGCAACA -GC--- UGCUGGUCGCG... SEQ ID NO: 7103

MII.O4 (RNA Mango II Probe for osk mRNA in drosophila from 970-1009)
5'GGCGCATTTACGCTG A GGAGAGGAGAGGAAGAGGAG A GCTTGCTGGTAGAAA CTCCT TTGTTGAGAT SEQ ID NO: 7104
3'CCGCGTAAATGCGAC ------------------------- CGAACGACCATCTTT ----- AACAACTCTA GG
SEQ ID NO: 7105

Figure 28

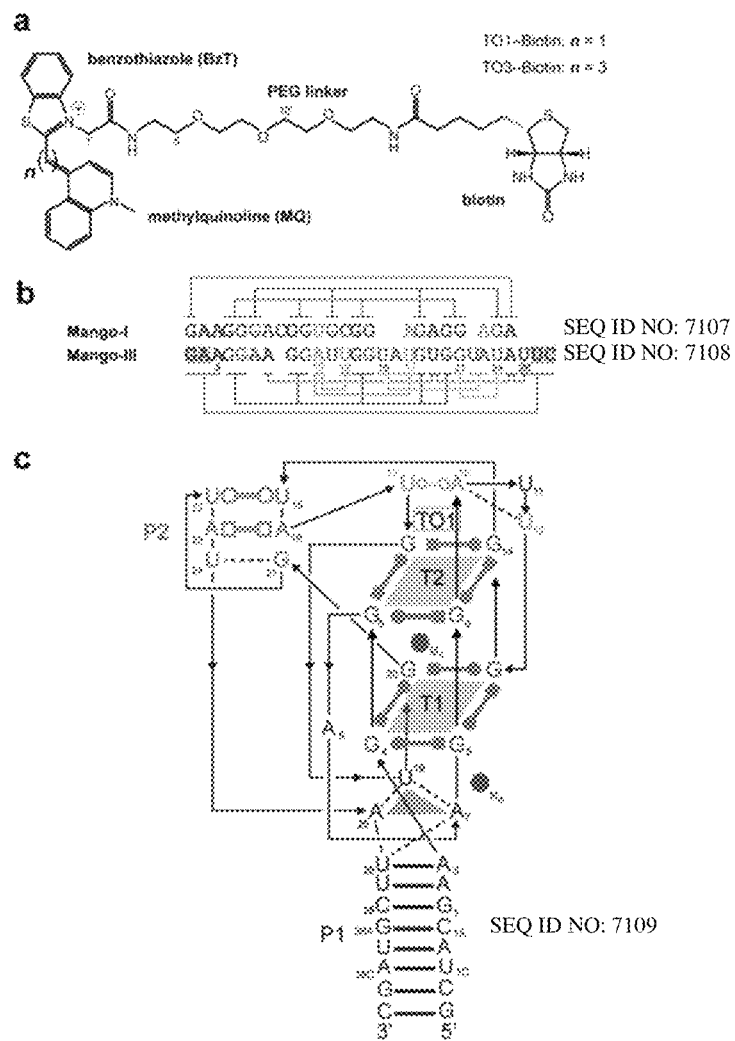
Figures 46A-C

| Aptmt. | Sequence | | $K_d$-TO1B (nM) | TO1B Brightness (Relative) | $K_d$-TO3B (nM) | TO3B Brightness (Relative) |
|---|---|---|---|---|---|---|
| Mango III-A15U | GGCACGUACGAARGAAGGUAGGUAAGGUAUAGUCGUACGGGC | SEQ ID NO: 7117 | 1.0 ± 0.8 | 1.17 ± 0.02 | 170 ± 20 | 0.06 ± 0.02 |
| Mango III-WT | GGCACGUACGAARGAAGGUAGGUAAGGUAUAGUCGUACGGGC | SEQ ID NO: 7118 | 1.0 ± 0.8 | 1.00 ± 0.02 | 92 ± 9 | 1.00 ± 0.03 |
| Mango III-A15G-U23A | GGCACGUACGAARGAAGGUAGGUAAGGUAUAGUCGUACGGGC | SEQ ID NO: 7119 | 34 ± 1 | 0.78 ± 0.02 | 22 ± 17 | 1.31 ± 0.17 |
| Mango III-U23A | GGCACGUACGAARGAAGGUAGGUAAGGUAUAGUCGUACGGGC | SEQ ID NO: 7120 | 28 ± 1 | 0.81 ± 0.03 | 82 ± 9 | 0.98 ± 0.03 |
| Mango III-A15G | GGCACGUACGAARGAAGGUAGGUAAGGUAUAGUCGUACGGGC | SEQ ID NO: 7121 | 14 ± 1 | 0.88 ± 0.03 | 160 ± 20 | 0.75 ± 0.03 |
| Mango III-A15G-U23G | GGCACGUACGAARGAAGGUAGGUAAGGUAUAGUCGUACGGGC | SEQ ID NO: 7122 | 87 ± 4 | 0.87 ± 0.01 | 180 ± 20 | 0.67 ± 0.03 |
| Mango III-U23G | GGCACGUACGAARGAAGGUAGGUAAGGUAUAGUCGUACGGGC | SEQ ID NO: 7123 | 1000 ± 3 | 0.41 ± 0.03 | 1100 ± 900 | 0.36 ± 0.03 |
| Mango III-U23C | GGCACGUACGAARGAAGGUAGGUAAGGUAUAGUCGUACGGGC | SEQ ID NO: 7124 | 170 ± 9 | 0.34 ± 0.02 | 810 ± 400 | 0.6 ± 0.08 |
| Mango III-A15G-U23C | GGCACGUACGAARGAAGGUAGGUAAGGUAUAGUCGUACGGGC | SEQ ID NO: 7125 | 640 ± 80 | 0.26 ± 0.04 | ND | 0.06 ± 0.02 |
| Mango III-A15C-U23A | GGCACGUACGAARGAAGGUAGGUAAGGUAUAGUCGUACGGGC | SEQ ID NO: 7126 | 950 ± 10 | 0.26 ± 0.01 | 420 ± 20 | 0.42 ± 0.03 |
| Mango III-A15C | GGCACGUACGAARGAAGGUAGGUAAGGUAUAGUCGUACGGGC | SEQ ID NO: 7127 | 500 ± 30 | 0.29 ± 0.01 | ND | 0.08 ± 0.02 |
| Mango III-A15C-U23G | GGCACGUACGAARGAAGGUAGGUAAGGUAUAGUCGUACGGGC | SEQ ID NO: 7128 | 530 ± 400 | 0.14 ± 0.01 | 3600 ± 3000 | 0.22 ± 0.03 |
| Mango III-A15C | GGCACGUACGAARGAAGGUAGGUAAGGUAUAGUCGUACGGGC | SEQ ID NO: 7129 | 1600 ± 200 | 0.19 ± 0.01 | ND | 0.08 ± 0.02 |
| Mango III-A15G-U23C | GGCACGUACGAARGAAGGUAGGUAAGGUAUAGUCGUACGGGC | SEQ ID NO: 7130 | 1700 ± 300 | 0.08 ± 0.01 | ND | 0.08 ± 0.02 |
| Mango III-A15G-U23A | GGCACGUACGAARGAAGGUAGGUAAGGUAUAGUCGUACGGGC | SEQ ID NO: 7131 | 4400 ± 300 | 0.06 ± 0.01 | 170 ± 110 | 0.11 ± 0.03 |
| Mango III-A15G-U23G | GGCACGUACGAARGAAGGUAGGUAAGGUAUAGUCGUACGGGC | SEQ ID NO: 7132 | 2000 ± 600 | 0.04 ± 0.01 | 270 ± 180 | 0.13 ± 0.02 |

Figure 52

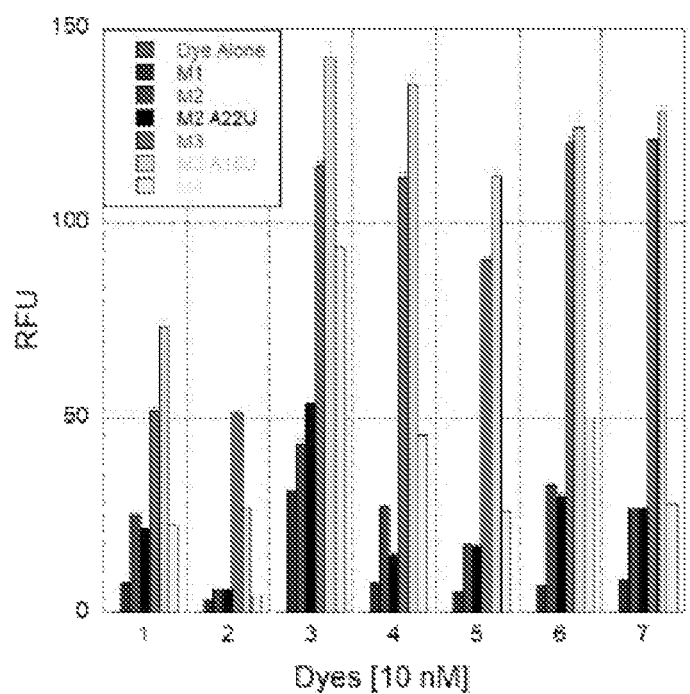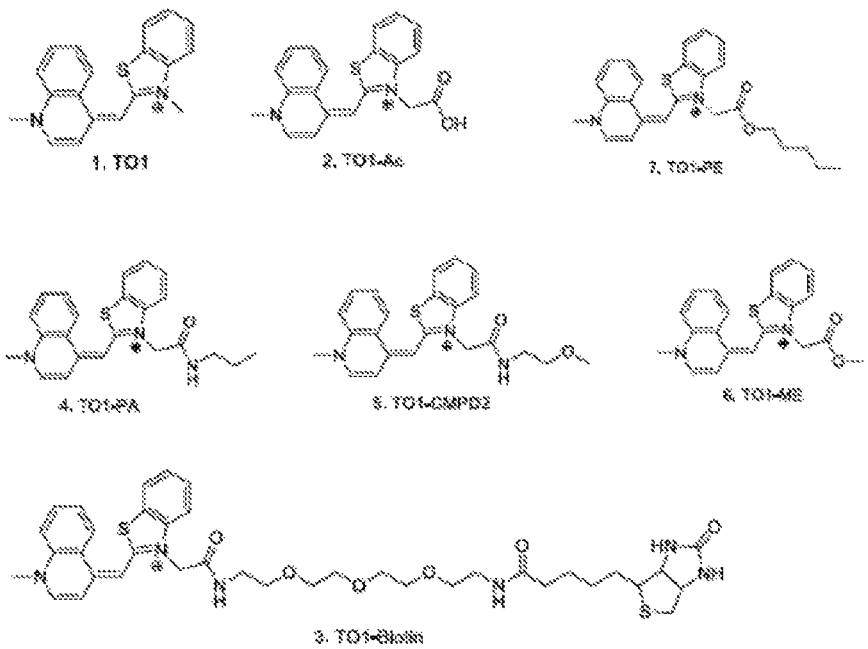
Figure 53

FLUOROGEN-BINDING RNA APTAMERS

FIELD

The invention is in the field of nucleic acid biochemistry, providing RNA aptamers that bind heterocyclic fluorophores, adapted for use in measuring or testing processes that include fluorogenic hybridization assays.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 7551601100_SL.txt. The text file is about 1,362 KB, was created on Mar. 26, 2021, and is being submitted electronically via EFS Web.

BACKGROUND

RNA plays many important roles in cellular biology. However, directly imaging biologically important RNAs has been hindered by a lack of fluorescent tools equivalent to the fluorescent proteins available to study cellular proteins. Preferably, RNA labelling systems should preserve biological function, have photophysical properties similar to existing fluorescent proteins, and be compatible with established live and fixed cell protein labelling strategies.

Since their creation, fluorogenic RNA aptamers that enhance the fluorescence of an unbound fluorophore have sparked significant interest and hold great potential, for example to enable the visualization of RNA molecules within a cell. However, their application has in some cases been limited due to their inability to fold into a correct tertiary structure that simultaneously binds a target fluorophore tightly and in an orientation that maximizes fluorescence (Dolgosheina, E. V. and Unrau, P. J. (2016), Fluorophore-binding RNA aptamers and their applications. WIREs RNA, 7: 843-851). Optimization of both fluorophore binding and bound complex brightness is desirable for fluorescent RNA imaging tags, particularly for the study of cellular RNAs.

SUMMARY

Aptamers are disclosed with distinct fluorescent properties, fluorophore binding affinities, and salt dependence, with specific embodiments designated herein Mango-II, III and IV. Also disclosed are corresponding fluorophores, with selected fluorophores evidencing high cellular permeability. The aptamer's high fluorophore affinities, the high brightness of the bound complexes, and their thermal and salt stability, provide distinct aspects of the disclosed aptamers. The aptamers may accordingly be adapted to work with existing microscope methodologies optimized for the study of proteins. Aspects of the present innovation accordingly involve the use of the disclosed aptamers to study RNA function and dynamics both in vitro and in vivo. Exemplified embodiments have been used for imaging RNA molecules in fixed and live mammalian cells. In particular, the examples herein illustrate that the disclosed aptamers can accurately image the sub-cellular localization of two small non-coding RNAs (5S and U6) in both fixed and live cells. Selected aptamers are shown herein to be as bright or brighter than enhanced GFP when bound to TO1-Biotin.

INVENTION

The invention relates to a RNA aptamer comprising an active core sequence as set forth in:

(SEQ ID NO: 2)
5'- GG@($T_1$/WGW)GG(#$_1$H/WG)WGGN@(#$_2$/-)G($T_2$/H)GNH
(AN@$T_3$/G)-3' with the proviso that the active core sequence is not the sequence as set forth in SEQ ID NO: 1: GAAGGGACG-GUGCGGAGAGGAGA.
wherein, within the active core sequence
 represents no nucleotide (gap);
K represents U or G;
S represents C or G;
R represents A or G;
W represents A or U;
H represents A, C or U;
N represents A, C, G or U; and
@ represents N or no nucleotide;
wherein /, between the brackets ( ) represents an alternative;
and wherein $T_1$ represents any nucleotide, $T_2$ and $T_3$ being defined as follows:
when $T_1$ is A, $T_2$ can be either A, G or U; and
 when $T_1$ is A and $T_2$ is A, then $T_3$ is U;
 when $T_1$ is A and $T_2$ is G, then $T_3$ is U; and
 when $T_1$ is A and $T_2$ is U, then $T_3$ is A or U; or
when $T_1$ is C, $T_2$ can be either G or U; and
 when $T_1$ is C and $T_2$ is G, then $T_3$ is C or G; and
 when $T_1$ is C and $T_2$ is U, then $T_3$ is G; or
When $T_1$ is G, $T_2$ can be either G or C, and $T_3$ is C; or
When $T_1$ is U, $T_2$ can be either A or C; and
 when $T_1$ is U and $T_2$ is A, then $T_3$ is A or U; and
 when $T_1$ is U and $T_2$ is C, then $T_3$ is A;
wherein #$_1$ and #$_2$ represents any nucleotide pair such that
 when #$_1$ is A, then #$_2$ represents A, C, G or U; or
 when #$_1$ is C, then #$_2$ is C; or
 When #$_1$ is G, then #$_2$ is G; or
 when #$_1$ is U, then #$_2$ represents A, G or U.
wherein #$_1$ and #$_2$ represents any nucleotide pair such that
 when #$_1$ is A, then #$_2$ represents A, C, G or U; or
 when #$_1$ is C, then #$_2$ is C; or
 When #$_1$ is G, then #$_2$ is G; or
 when #$_1$ is U, then #$_2$ represents A, G or U.
wherein the aptamer adopts a determined tridimensional conformation which is a fluorophore binding conformation, said aptamer when it adopts the fluorophore binding conformation being liable to interact with a fluorophore; wherein the aptamer further comprises, contiguous with the active core sequence, a 5' leader sequence attached, or operably linked to (by covalent bound, i.e. phosphodiester bound), to the 5' terminus of the active core and a 3' tail sequence attached, or operably linked to (by covalent bridge mentioned below), to the 3' terminus of the active core, wherein the 5' leader sequence and the 3' tail sequence together mediate the juxtaposition of the 5' terminus of the active core and the 3' terminus of the active core when the aptamer is the fluorophore binding conformation.

The invention is based on the identification by the inventors of nucleic acid molecules having a determined structure that adopts a specific conformation (binding conformation)

to interact with fluorophore compounds to form a fluorophore-aptamer complex. When the interaction occurs, the fluorescence of the fluorophore significantly increases compared to the fluorescence of the fluorophore that does not form a complex with the aptamer complex.

Advantageously, the sequence of the aptamer as defined above encompasses the two following sequences

```
                                            (SEQ ID NO: 3)
5'- GG@(T1)GG(#1H)WGGN@ (#2)G(T2)GNH(AN@T3)-3';
and (SEQ ID NO: 4)
5'- GG@(WGW)GG(WG)WGGN@G(H)GNH(G)-3'.
```

The aptamer, in its binding conformation, forms a G-quadruplex and appears like an hairpin.

Advantageously, the invention relates to the aptamer as defined above, wherein said aptamer can interact with a fluorophore, said fluorophore being selected from a group consisting of the following compounds of the following Formula I and Formula II:

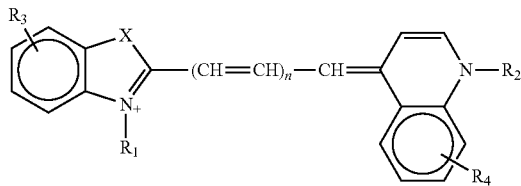

(I)

wherein:
X represents 0, S, Se, or $C(CH_3)_n$;
$R_1$ represents an alkyl having from 1-6 carbons;
$R_2$ represents an alkyl having from 1-6 carbons;
$R_3$ is either a fused benzene, an alkyl having 1-6 carbons, a methoxy or H;
$R_4$ is an alkyl having 1-6 carbons, a methoxy or H; and
n=zero or an integer from 1-6;

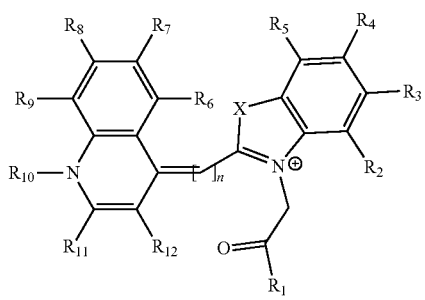

(II)

wherein:
$R_1$ represents any substituent;
$R_2$ through $R_5$ represent H, F, Cl, Br, I, $CH_3$, linear polymers, or extended heterocycles
$R_6$-$R_9$ represent H, F, Cl, Br, I, $CH_3$, linear polymers, or extended heterocycles
$R_{10}$ represents H, F, Cl, Br, I, $CH_3$, linear polymers, or extended heterocycles.
$R_{11}$ through $R_{12}$ represent H, F, Cl, Br, I, $CH_3$, linear polymers, or extended heterocycles
X represents the following atoms O, S and Se; and
n is 1 or 3 or 5.

Advantageously, the RNA aptamer as defined above has a fluorophore binding affinity of at least 0.5 µM when the active core is in a fluorophore binding conformation.

More advantageously, the binding of the fluorophore of formula I or II by the RNA aptamer, as defined above, in the fluorophore binding conformation, increases the fluorescence of the fluorophore of formula I or II, and the fluorophore-aptamer complex has a brightness of at least 5,000 $M^{-1}$ $cm^{-1}$.

Advantageously, the invention relates to the RNA aptamer as defined above, wherein the fluorophore complex has a brightness of at least 6,000, or at least 7,000, or at least 8,000, or at least 9,000, or at least 10,000, or at least 11,000 $cm^1$.

Advantageously, the invention relates to the RNA aptamer as defined above, wherein the core active sequence comprises the following sequence:

```
                                            (SEQ ID NO: 5)
5'-$1GGNT1GG#1HUGGHA#2GT2GNHAN@T3$2-3'
``` wherein:
H represents A, C or U
N represents A, C, G or U
@ represents any nucleotide or no nucleotide
$\#_1$ and $\#_2$ represents any nucleotide pair such that
    when $\#_1$ is A, then $\#_2$ represents A, C, G or U; or
    when $\#_1$ is C, then $\#_2$ is C; or
    When $\#_1$ is G, then $\#_2$ is G; or
    when $\#_1$ is U, then $\#_2$ represents A, G or U.
$\$_1$ and $\$_2$ represent any pair of nucleotides such that
    when $\$_1$ is A, then $\$_2$ is A, G or U; or
    when $\$_1$ is C, then $\$_2$ is A, G or U; or
    when $\$_1$ is G, then $\$_2$ is A, C, G or U; or
    when $\$_1$ is U, then $\$_2$ is A, G.
wherein the 5' and 3' external sequence forms a helix that is substantially base paired.

Advantageously, the invention relates to The RNA aptamer defined above, wherein the core active sequence comprises the following sequence:

```
                                            (SEQ ID NO: 6)
GG@WGWGGWGWGGN@GHGGHG
``` wherein:
W represents A or U;
H represents A, C or U;
N represents A, C, G or U; and
@ represents N or no nucleotide.

Advantageously, the invention relates to the RNA aptamer as defined above, wherein the core active sequence comprises the following sequence:

```
                                            (SEQ ID NO: 7)
GAA(GG)1AA(GG)2NUU(GG)3UAN'G4iUG4iiGUAUAUUC
``` wherein:
N is any nucleotide, N' the anti-watson crick partner to N wherein $(GG)_1$, $(GG)_2$, $(GG)_3$ and $G_{4i}$ and $G_{4ii}$ form a quadruplex structure when the active core is in the fluorophore binding conformation, with the 5' terminus of the active core being juxtaposed to the 3' terminus of the active core.

Advantageously, the invention relates to the RNA aptamer as defined above, wherein the core active sequence comprises the following sequence:

(SEQ ID NO: 8)
[G/C]NR(GG)$_1$[R/D]AG[A/U](GG)$_2$NGN(GG)$_3$A*[A/U/D]GA*

(GG)$_4$[A/C]R[A/D]

wherein:
A* is A or N,
N is any nucleotide
R is a purine,
D denotes the absence of nucleotide,
wherein (GG)$_1$, (GG)$_2$, (GG)$_3$ and (GG)$_4$ form a quadruplex structure when the active core is in the fluorophore binding conformation, with the 5' terminus of the active core being juxtaposed to the 3' terminus of the active core.

More advantageously, the invention relates to the RNA aptamer as defined above, wherein the core active sequences comprises one of the sequences as set forth in SEQ ID NO: 9 to SEQ ID NO: 6829, preferably as set forth in SEQ ID NO: 9 to SEQ ID NO: 6887.

In another advantageous embodiment, the aptamer according to the invention comprises or consists essentially of or consists of one of the sequences as set forth in SEQ ID NO: 6830 to SEQ ID NO: 6875 (Mango III) or as set forth in SEQ ID NO: 6876 to SEQ ID NO: 6887 (Mango II).

Advantageously, the invention relates to the RNA aptamer comprising a core active sequence as defined above, with the proviso that said aptamer active core does not have the core sequence: GNR(GG)$_1$GNN(GG)$_2$NGN(GG)$_3$AGN(GG)$_4$AGA SEQ ID NO 6888, wherein R is a purine, and N is any nucleotide.

Advantageously, the invention relates to the RNA aptamer according to the above definition, wherein the 5' leader sequence and the 3' tail sequence are complementary, so that binding of the 5' leader sequence to the 3' tail sequence mediates the juxtaposition of the 5' terminus of the active core and the 3' terminus of the active core when the aptamer is the fluorophore binding conformation.

More advantageously, the invention relates to the RNA aptamer according to the above definition, wherein the 5' leader sequence and the 3' tail sequence are complementary to a target sequence, the target sequence comprising:
a leader bait sequence that is complementary to the 3' tail sequence of the aptamer; and
a tail bait sequence that is complementary to the 5' leader sequence of the aptamer;
the leader and tail bait sequences being juxtaposed in the target sequence, so that binding of:
binding of the 3' tail sequence to the 5' leader bait sequence; mediates the juxtaposition of the 5' terminus of the active core and the 3' terminus of the active core when the aptamer is in the fluorophore binding conformation.

More advantageously, the invention relates to the RNA aptamer as defined above, wherein the leader and tail bait sequences being contiguous in the target sequence.

More advantageously, the invention relates to the RNA aptamer according to the above definition, wherein juxtaposition of the 5' terminus of the active core and the 3' terminus of the active core when the aptamer is the fluorophore binding conformation brings a phosphate group from the 5' terminus to within 10 Å, or to within 9 Å or to within 8 Å, of a phosphate group from the 3' terminus.

More advantageously, the invention relates to the RNA aptamer according to the above definition, wherein the aptamer has a fluorophore binding affinity of at least 400 nM, 300 nM, 200 nM, 100 nM, 50 nM, 40 nM, 30 nM, 20 nM, 10 nM, 5 nM, 1 nM or 0.5 nM when the core is in a fluorophore binding conformation. More advantageously, the invention relates to the RNA aptamer according to the above definition, wherein the fluorophore-aptamer complex has a brightness of at least 7,000 M$^{-1}$cm$^{-1}$, 8,000 M$^{-1}$cm$^{-1}$, 9,000 M$^{-1}$ cm$^{-1}$, 10,000 M$^{-1}$ cm$^{-1}$, or 43,000 M$^{-1}$cm$^{-1}$.

More advantageously, the invention relates to the RNA aptamer according to the above definition, wherein the fluorophore-aptamer complex has a fluorescent lifetime of at least 1 ns, or at least 2 ns, or at least 3 ns, or at least 4 ns or at least 5 ns, or at least 6 ns, or in the range of 1-6 ns, i.e. 1, or 2, or 3 or 4, or 6 or 6 ns.

More advantageously, the invention relates to the RNA aptamer according to the above definition, wherein the fluorophore-aptamer complex is fluorescent in a formaldehyde solution.

In another advantageous embodiment, the invention relates to the RNA aptamer according to the above definition, wherein the secondary aptamer sequence has affinity for a secondary target moiety.

The invention also relates to an RNA aptamer comprising an active core sequence, wherein the aptamer has a fluorophore binding affinity of at least 0.5 μM when the active core is in a fluorophore binding conformation, wherein the active core has a 5' terminus and a 3' terminus, and wherein the active core sequence from the 5' terminus to the 3' terminus is one of:
Active Core I:

(SEQ ID NO: 8)
[G/C]NR(GG)$_1${RAGU/AG[A/U]/GNN}(GG)$_2$NGN(GG)$_3$A*

[A/U/D]GA*(GG)$_4$[A/C]R[A/D]

wherein within the { } the first two blocks are optionally RRG[A/U] or Active Core II (SEQ ID NO: 7)
GAA(GG)$_1$AA(GG)$_2$AUU(GG)$_3$UAUGU(GG)$_4$UAUAUUC wherein:
A* is A or N,
N is any nucleotide,
R is a purine,
D denotes the absence of a residue,
wherein G$_1$, G$_2$, G$_3$ and G$_4$ form a quadruplex structure when the active core is in the fluorophore binding conformation, with the 5' terminus of the active core being juxtaposed to the 3' terminus of the active core; and,
wherein the fluorophore is a compound of Formula I or Formula II

I

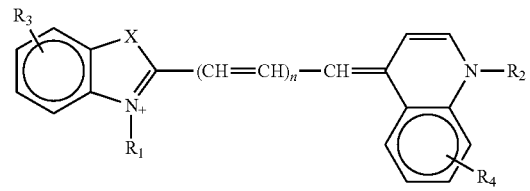

-continued

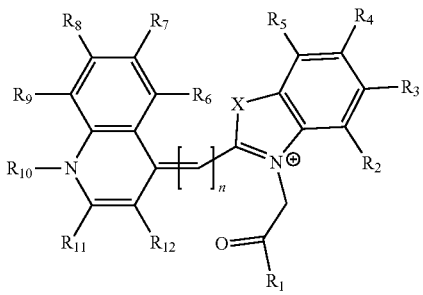

wherein substituents in Formula I are defined as follows:
X=O, S, Se, or C(CH$_3$)$_n$;
=alkyl having from 1-6 carbons;
R$_2$=alkyl having from 1-6 carbons;
R$_3$=fused benzene, alkyl having 1-6 carbons, methoxy or H;
R$_4$=alkyl having 1-6 carbons, methoxy or H; and
n=zero or an integer from 1-6.
wherein substituents in Formula II are defined as follows:

| | |
|---|---|
| R$_1$ | Any substituent |
| R$_2$ through R$_5$ | H, F, Cl, Br, I, CH$_3$, linear polymers, or extended heterocycles |
| R$_6$-R$_9$ | H, F, Cl, Br, I, CH$_3$, linear polymers, or extended heterocycles |
| R$_{10}$ | H, F, Cl, Br, I, CH$_3$, linear polymers, or extended heterocycles. |
| R$_{11}$ through R$_{12}$ | H, F, Cl, Br, I, CH$_3$, linear polymers, or extended heterocycles |
| X atoms | O, S, Se |
| n | 1 or 3 or 5 | wherein binding of the fluorophore by the aptamer in the fluorophore binding conformation increases the fluorescence of the fluorophore, and the fluorophore-aptamer complex has a brightness of at least 12,000 M$^{-1}$cm$^{-1}$;

wherein the aptamer further comprises, contiguous with the active core sequence, a 5' leader sequence attached to the 5' terminus of the active core and a 3' tail sequence attached to the 3' terminus of the active core, wherein the 5' leader sequence and the 3' tail sequence together mediate the juxtaposition of the 5' terminus of the active core and the 3' terminus of the active core when the aptamer is the fluorophore binding conformation.

The invention also relates to an RNA aptamer comprising an active core sequence, wherein the aptamer has a fluorophore binding affinity of at least 0.5 µM when the active core is in a fluorophore binding conformation, wherein the active core has a 5' terminus and a 3' terminus, and wherein the active core sequence from the 5' terminus to the 3' terminus is one of:

Active Core I:

(SEQ ID NO: 8)
[G/C]NR(GG)$_1${RAGU/AG[A/U]/GNN}(GG)$_2$NGN(GG)$_3$A*

[A/U/D]GA*(GG)$_4$[A/C]R[A/D]

wherein within the { } the first two blocks are optionally RRG[A/U] or Active Core II (SEQ ID NO: 7)
GAA(GG)$_1$AA(GG)$_2$AUU(GG)$_3$UAUGU(GG)$_4$UAUAUUC wherein:
A* is A or N,
N is any nucleotide,
R is a purine,
D denotes the absence of a residue,
wherein (GG)$_1$, (GG)$_2$, (GG)$_3$ and (GG)$_4$ form a quadruplex structure when the active core is in the fluorophore binding conformation, with the 5' terminus of the active core being juxtaposed to the 3' terminus of the active core; and,
wherein the fluorophore is a compound of Formula I or Formula II

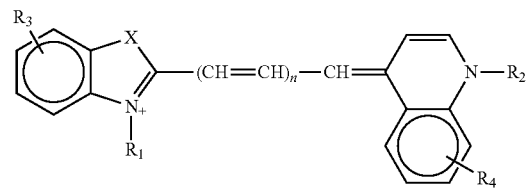

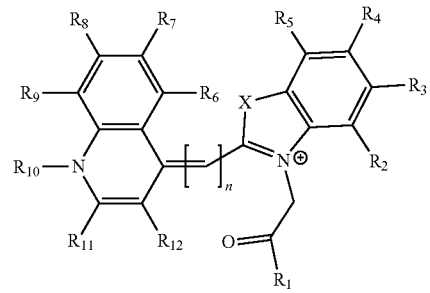

wherein substituents in Formula I are defined as follows:
X=O, S, Se, or C(CH$_3$)$_n$;
R$_1$=alkyl having from 1-6 carbons;
R$_2$=alkyl having from 1-6 carbons;
R$_3$=fused benzene, alkyl having 1-6 carbons, methoxy or H;
R$_4$=alkyl having 1-6 carbons, methoxy or H; and
n=zero or an integer from 1-6.
wherein substituents in Formula II are defined as follows:

| | |
|---|---|
| R$_1$ | Any substituent |
| R$_2$ through R$_5$ | H, F, Cl, Br, I, CH$_3$, linear polymers, or extended heterocycles |
| R$_6$-R$_9$ | H, F, Cl, Br, I, CH$_3$, linear polymers, or extended heterocycles |
| R$_{10}$ | H, F, Cl, Br, I, CH$_3$, linear polymers, or extended heterocycles. |
| R$_{11}$ through R$_{12}$ | H, F, Cl, Br, I, CH$_3$, linear polymers, or extended heterocycles |
| X atoms | O, S, Se |
| n | 1 or 3 or 5 | wherein binding of the fluorophore by the aptamer in the fluorophore binding conformation increases the fluorescence of the fluorophore, and the fluorophore-aptamer complex has a brightness of at least 5,000 M$^{-1}$cm$^{-1}$;

wherein the aptamer further comprises, contiguous with the active core sequence, a 5' leader sequence attached to the 5' terminus of the active core and a 3' tail sequence attached to the 3' terminus of the active core, wherein the 5' leader sequence and the 3' tail sequence together mediate the juxtaposition of the 5' terminus of the active core and the 3' terminus of the active core when the aptamer is the fluorophore binding conformation;

wherein the 5' leader sequence and the 3' tail sequence are complementary to a target sequence, the target (bait) sequence comprising:
  a leader bait sequence that is complementary to the 3' tail sequence of the aptamer; and,
  a tail bait sequence that is complementary to the 5' leader sequence of the aptamer;
the leader and tail bait sequences being juxtaposed in the target sequence, so that binding of:
  the 5' leader sequence to the tail bait sequence; combined with, binding of the 3' tail sequence to the leader bait sequence;
  mediates the juxtaposition of the 5' terminus of the active core and the 3' terminus of the active core when the aptamer is the fluorophore binding conformation.

Advantageously, the invention relates to the RNA aptamer as defined above, wherein the 5' leader bait and 3' tail bait sequences are contiguous in the target sequence.

The invention also relates to a molecular complex comprising, or consisting essentially of:
  an RNA aptamer as defined above; and
  a fluorophore selected from group consisting of the following compounds of the following Formula I and Formula II.

More advantageously, the invention relates to the molecular complex as defined above, wherein the fluorophore is chosen from the group consisting of the following compounds, where X=O, S or Se, and n=1, 3, or 5:

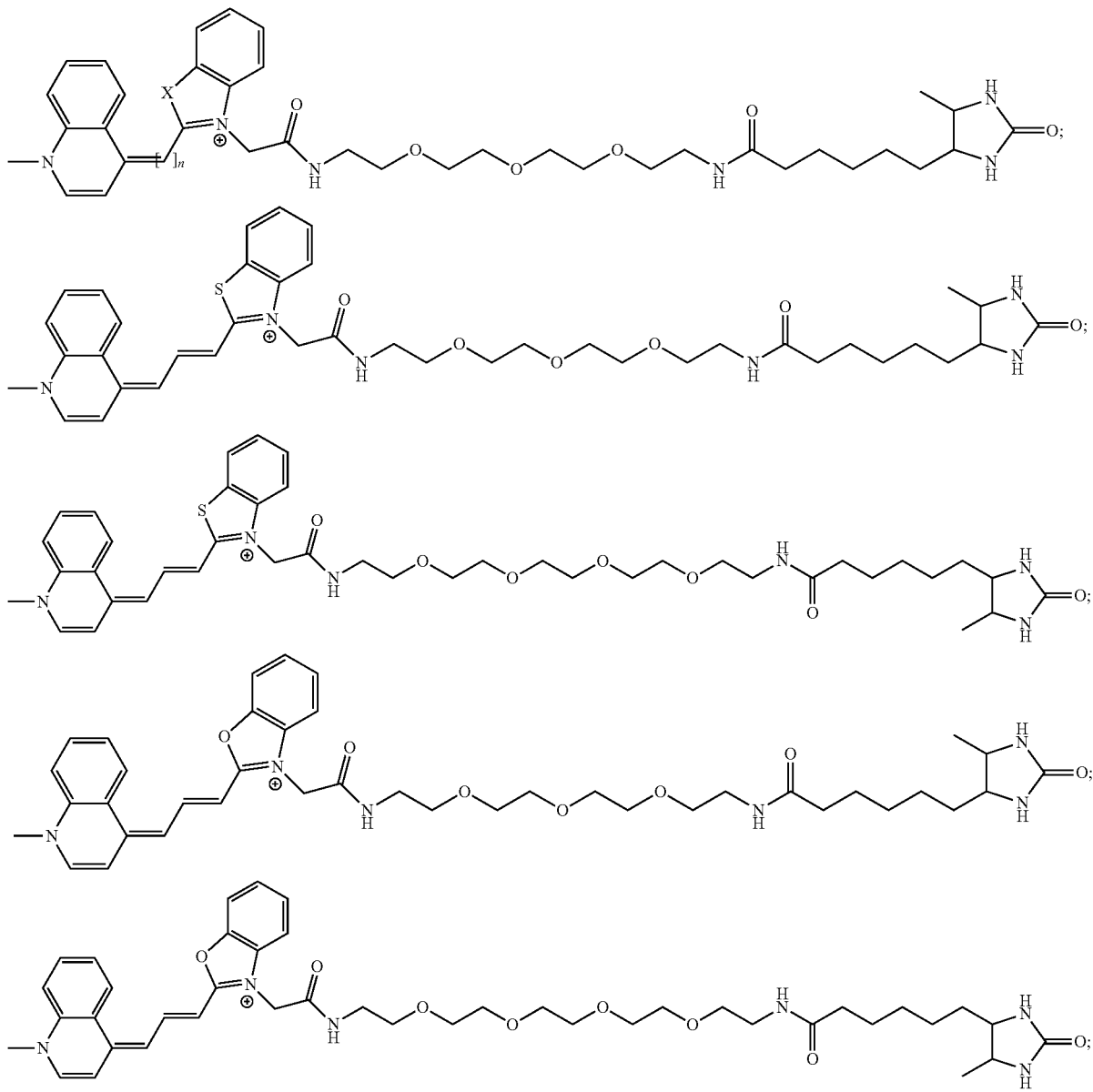

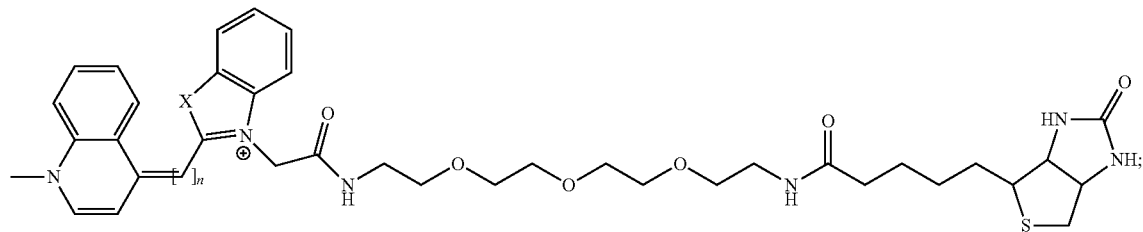
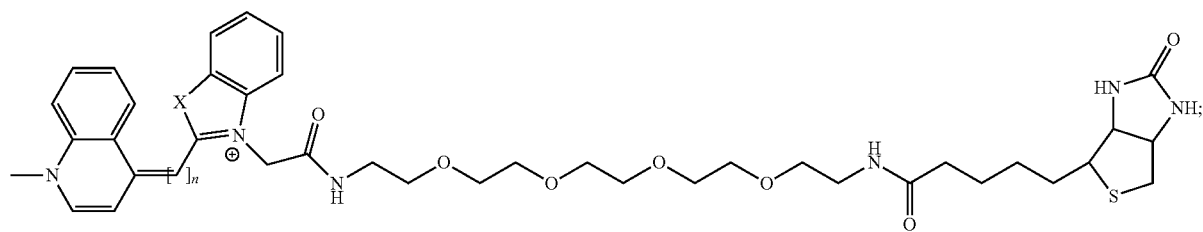
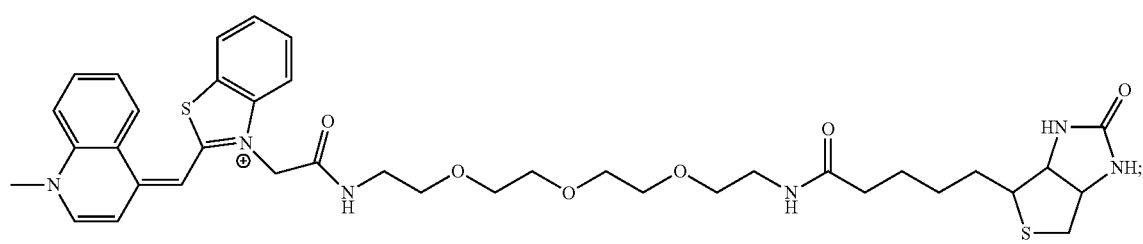
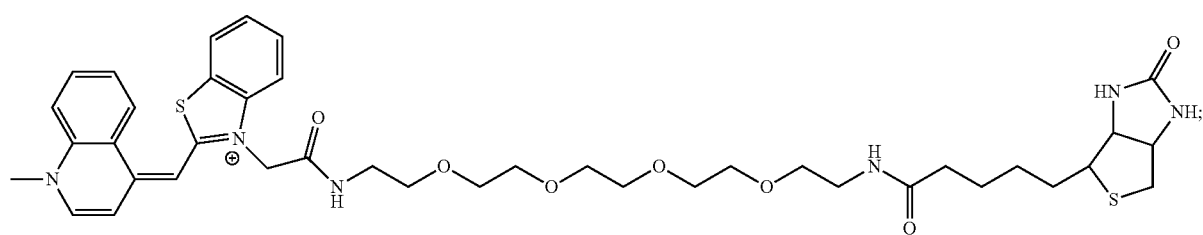
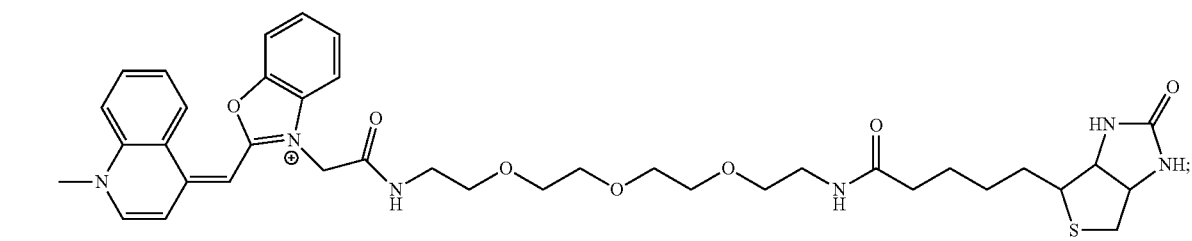
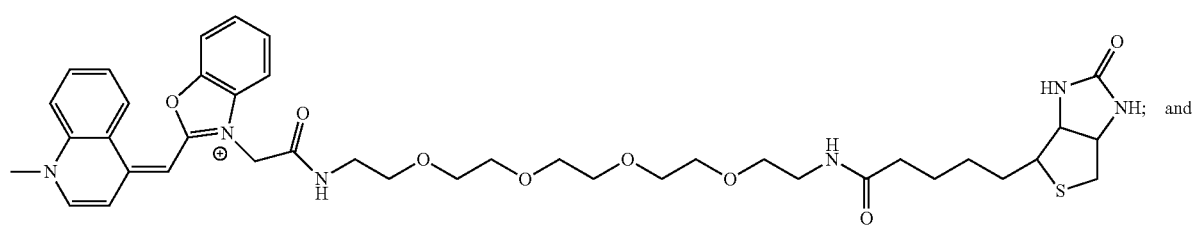

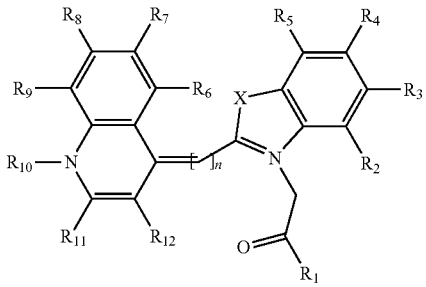

wherein $R_1$ is,

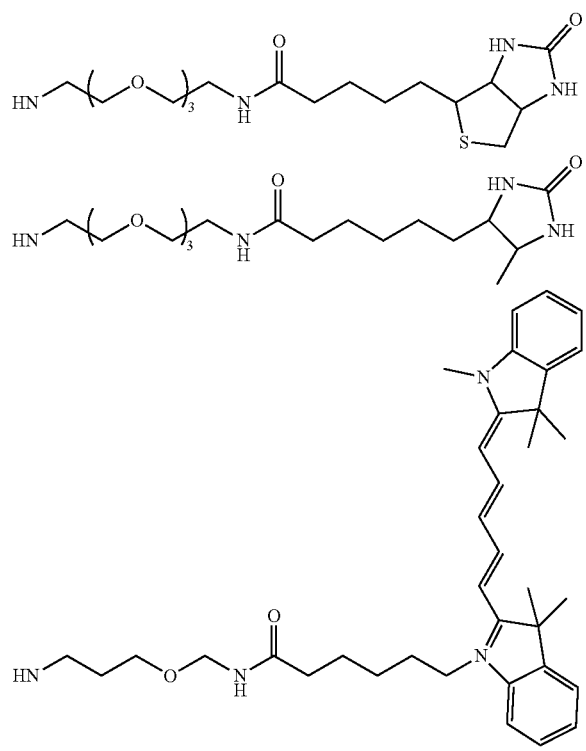

The invention will be better explained in the following figures and examples.

BRIEF DESCRIPTION OF THE DRAWINGS

FIG. 6|Resistance or selectivity of TO1-Biotin binding variants in presence of competitors after each round of screening. (a) NMM resistance selection: Resistance of TO1-Biotin/RNA complexes to NMM. The fluorescence of the complex between TO1-Biotin and the RNAs from the libraries obtained after each round of screening was determined by mixing 2 μM RNA and 100 nM TO1-Biotin in the absence or in the presence of 3 μM NMM. The Resistance to NMM was calculated by normalizing the aptamer/TO1-Biotin fluorescence in the presence of NMM by the aptamer/TO1-Biotin fluorescence in the absence of NMM. (b) TO3-Biotin resistance selection: Resistance of TO1-Biotin/RNA complexes to TO3-Biotin. The fluorescence of the complex between TO1-Biotin and the RNAs from the libraries obtained after each round of screening was determined by mixing 300 nM RNA and 100 nM TO1-Biotin, in the absence or in the presence of 1.6 μM TO3-Biotin. The resistance to TO3-Biotin was calculated by normalizing the aptamer/TO1-Biotin fluorescence in the presence of TO3-Biotin by the aptamer/TO1-Biotin fluorescence in the absence of TO3-Biotin. (c) Selectivity of the libraries obtained after the different rounds of screening in the presence of TO3-Biotin. The green fluorescence of the TO1-Biotin/RNA complex was normalized to the red fluorescence of the TO3-Biotin/RNA complex to calculate the selectivity index. The blue bar indicates the concentration of competitor used during the screening step. Data was obtained at 25° C., the values are the mean of three independent experiments and error bars correspond to ±1 standard error.

FIG. 7|Analysis of the clones obtained at the end of the screening process performed in the presence of NMM. (a) Brightness of the complexes formed between TO1-Biotin and individual variants isolated from the screenings in the presence of NMM. Aptamer-coding genes were PCR amplified, in vitro transcribed in the presence of TO1-Biotin and the fluorescence was monitored at 37° C. The maximal fluorescence was normalized to that of Mango I. (b) Resistance of TO1-Biotin/RNA complex to NMM. TO1-Biotin fluorescence was monitored as in (a) in the absence or in the presence of 3 μM NMM. (c) Sequence analysis of the clones of interest. The sequences of the clones of interest (indicated by an asterisk in a and b) were aligned with Clustal X. The green boxes indicate Mango III (R5-NMM-20) and Mango IV (R5-NMM-5).

FIG. 9|Mutations and truncations of Mangos-II, III and IV. (a) Mango II constructs. (b) Mango IV constructs. (c) Mango III constructs. $F_E$ is relative to the full-length construct, which was normalized to one. Constructs with binding affinities higher than the end point of titration are labeled 'u.d.' (undeterminable). The closing stem regions are highlighted in purple. Guanine residues protected from DMS cleavage in the named Mango constructs of the study (FIG. 2d) are highlighted in yellow.

TABLE 1

| Hill coefficients of RNA Mango/TO1-Biotin complexes | | | | |
|---|---|---|---|---|
| | Hill Coefficients | | $K_D$ (mM) | |
| | $K^+$ | $Na^+$ | $K^+$ | $Na^+$ |
| Mango-I | 1.2 ± 0.1 | N/A | 48 ± 5 | N/D |
| Mango-II | 1.4 ± 0.2 | 0.8 ± 0.1 | 39 ± 10 | 170 ± 110 |
| Mango-III | 1.0 ± 0.8* | 0.5 ± 0.5 | 0.4 ± 0.1 | 0.8 ± 0.3 |
| Mango-IV | 1.5 ± 0.2* | N/A | 64 ± 24 | N/D |

Errors are the standard deviation of three independent measurements.
*Hill coefficients with an asterisk are estimated based on initial rise of fluorescence data.

Figure 11:
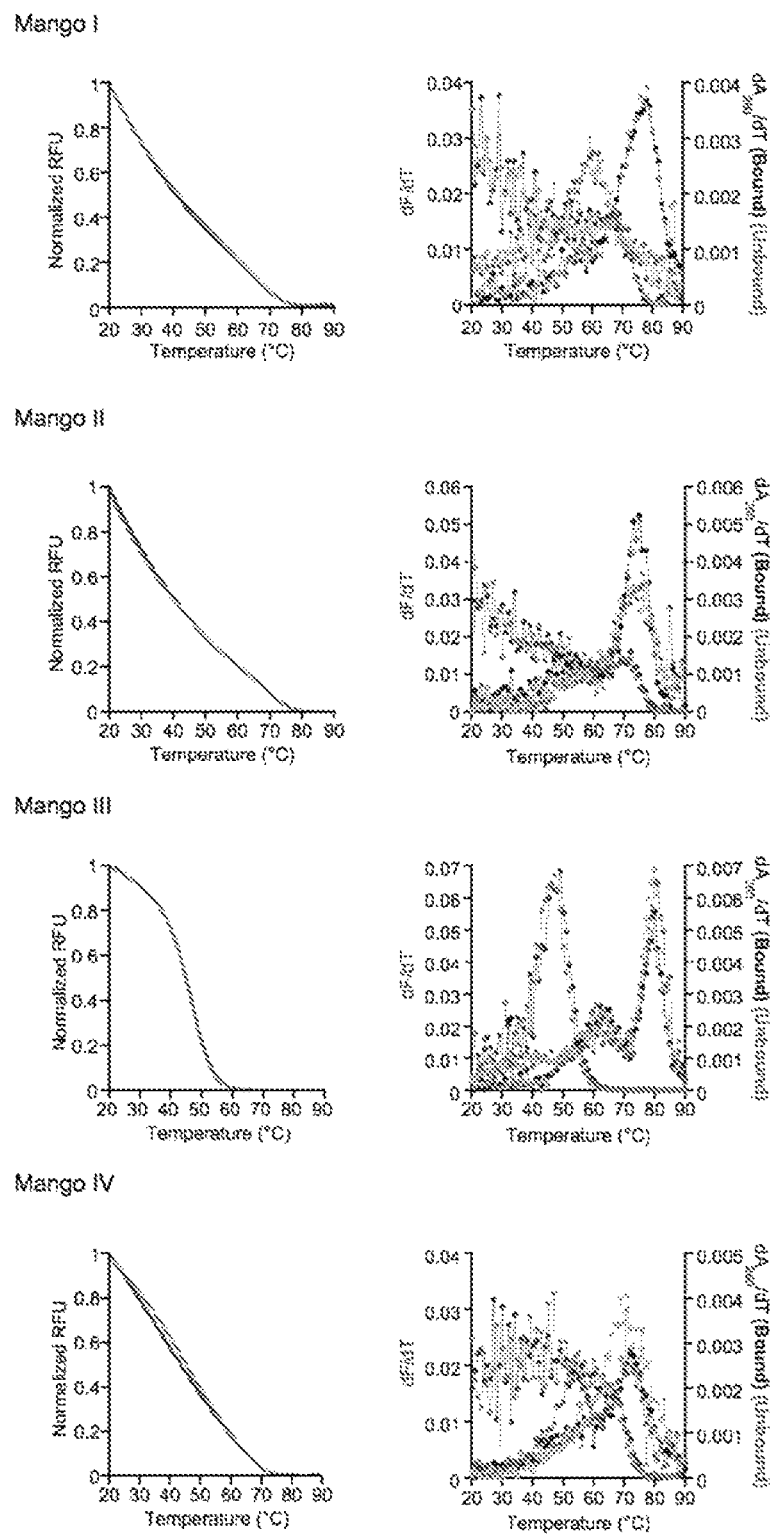

FIG. 11|Temperature-dependent fluorescent and UV absorbance spectroscopy of new Mango variants. Line plots of temperature-dependent spectroscopy for Mango I (data obtained from previous work)[1], Mango II, Mango III, and Mango IV. Left panels: 1 μM RNA was incubated with 5 μM TO1-Biotin and subjected to temperature ramps while monitoring fluorescence (red shades). Right panels: $A_{260}$ for this sample with 5 μM TO1-Biotin (green shades) and without TO1-Biotin (blue shades) were collected and the simple derivative plotted together with the derivative of the fluorescence data. Starting at 90° C., temperature was ramped down at a rate of 1° C./min to 20° C. (darker shade) and returned to 90° C. at a rate of 1° C./min (lighter shade).

Figure 12:
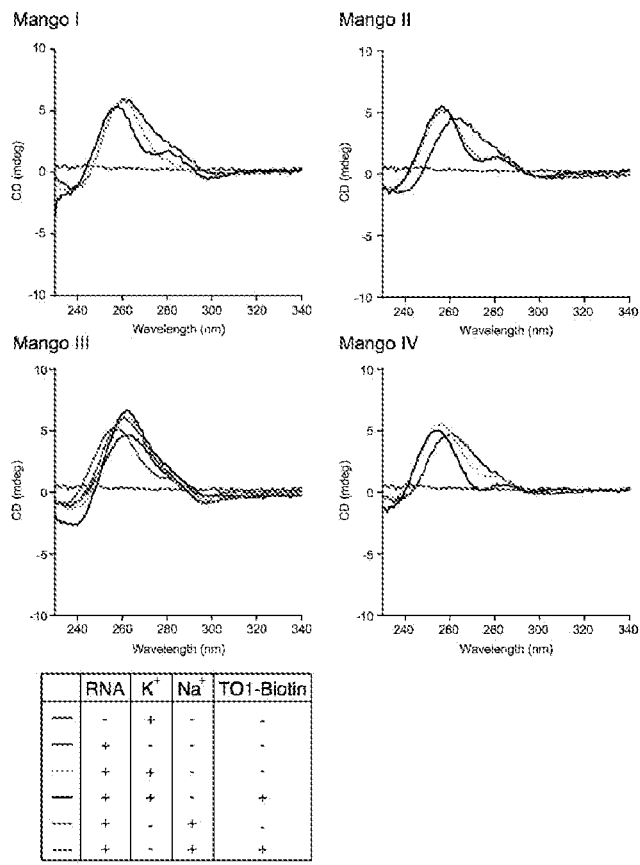

FIG. 12|Circular dichroism spectra. Circular dichroism spectra of Mango I, II, III, and IV. 5 μM RNA was measured in 10 mM Tris pH 7.5 buffer either alone, with 140 mM monovalent salt, and/or with 7 μM TO1-Biotin as indicated by the legend. Data is a line plot to guide the eye.

Figure 13:
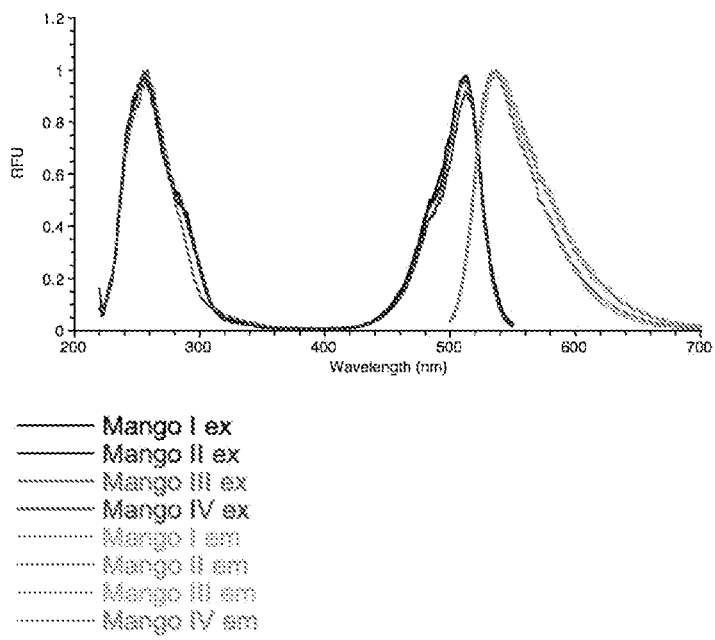

FIG. 13|Photophysics: excitation/emission. (a) Excitation (dark curve) and emission (light curve) spectra of each Mango. All Mangos have $\Delta_{ex}$ max=510 nm and $\Delta_{em}$ max=535 nm. Color-coding is as follows: Black—Mango I, Blue—Mango II, Green—Mango III, Red—Mango IV.

Figure 14:
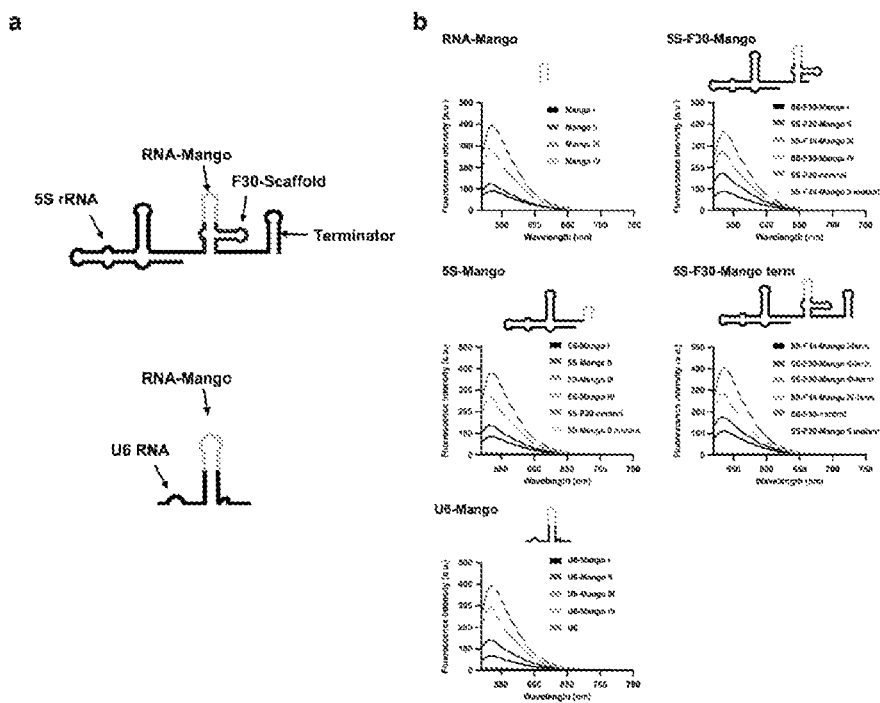

FIG. 14|RNA scaffold diagrams. Diagrams of the 5S-Mango and U6-Mango constructs synthesized (sequences in Table 2) and their fluorescence emission as a function of wavelength after excitation at 505 nm, compared to unmodified Mango I-IV.

TABLE 2

Constructs used in in vivo experiments

| Construct | Sequence | SEQ ID NO: |
|---|---|---|
| 5S-30-Control | GTCTACGGCC ATACCACCCT GAACGCGCCC GATCTCGTCT GATCTCGGAA GCTAAGCAGG GTCGGGCCTG GTTAGTACTT GGATGGGAGA CCGCCTGGGA ATACCGGGTG CTGTAGGCGT CGACTTGCCA TGTGTATGTG GGGAAACCCA CATACTCTGA TGATCCTTCG GGATCATTCA TGGCAATCTA GA | 6889 |
| 5S-F30-Mango II mutant | GTCTACGGCC ATACCACCCT GAACGCGCCC GATCTCGTCT GATCTCGGAA GCTAAGCAGG GTCGGGCCTG GTTAGTACTT GGATGGGAGA CCGCCTGGGA ATACCGGGTG CTGTAGGCGT CGACTTGCCA TGTGTATGTG GGTACGAATT AGATTAGATT AAGATTAGAG TACCCACATA CTCTGATGAT CCTTCGGGAT CATTCATGGC AATCTAGA | 6890 |
| 5S-F30-Mango I | GTCTACGGCC ATACCACCCT GAACGCGCCC GATCTCGTCT GATCTCGGAA GCTAAGCAGG GTCGGGCCTG GTTAGTACTT GGATGGGAGA CCGCCTGGGA ATACCGGGTG CTGTAGGCGT CGACTTGCCA TGTGTATGTG GGTACGAAGG GACGGTGCGG AGAGGAGAGT ACCCACATAC TCTGATGATC CTTCGGGATC ATTCATGGCA ATCTAGA | 6891 |
| 5S-F30-Mango II | GTCTACGGCC ATACCACCCT GAACGCGCCC GATCTCGTCT GATCTCGGAA GCTAAGCAGG GTCGGGCCTG GTTAGTACTT GGATGGGAGA CCGCCTGGGA ATACCGGGTG CTGTAGGCGT CGACTTGCCA TGTGTATGTG GGTACGAAGG AGAGGAGAGG AAGAGGAGAG TACCCACATA CTCTGATGAT CCTTCGGGAT CATTCATGGC AATCTAGA | 6892 |
| 5S-F30-Mango III | GTCTACGGCC ATACCACCCT GAACGCGCCC GATCTCGTCT GATCTCGGAA GCTAAGCAGG GTCGGGCCTG GTTAGTACTT GGATGGGAGA CCGCCTGGGA ATACCGGGTG CTGTAGGCGT CGACTTGCCA TGTGTATGTG GGTACGAAGG AAGGATTGGT ATGTGGTATA TTCGTACCCA CATACTCTGA TGATCCTTCG GGATCATTCA TGGCAATCTA GA | 6893 |
| 5S-F30-Mango IV | GTCTACGGCC ATACCACCCT GAACGCGCCC GATCTCGTCT GATCTCGGAA GCTAAGCAGG GTCGGGCCTG GTTAGTACTT GGATGGGAGA CCGCCTGGGA ATACCGGGTG CTGTAGGCGT CGACTTGCCA TGTGTATGTG GGTACCGAGG GAGTGGTGAG GATGAGGCGA GTACCCACAT ACTCTGATGA TCCTTCGGGA TCATTCATGG CAATCTAGA | 6894 |
| 5S Δ78-98-F30-Mango IV | GTCTACGGCC ATACCACCCT GAACGCGCCC GATCTCGTCT GATCTCGGAA GCTAAGCAGG GTCGGGCCTG GTTAGTAGAA AGAATACCGG GTGCTGTAGG CGTCGACTTG CCATGTGTAT GTGGGTACCG AGGGAGTGGT GAGGATGAGG CGAGTACCCA CATACTCTGA TGATCCTTCG GGATCATTCA TGGCAA | 6895 |
| U6-Mango IV | GTGCTCGCTT CGGCAGCACA TATACTAAAA TTGGAACGAT ACAGAGAAGA TTAGCATGGC CCCTACCGAG GGAGTGGTGA GGATGAGGCG AGTAGGATGA CACGCAAATT CGTGAAGCGT TCCATATTTT T | 6896 |
| 5' SalI F30 primer | GGCGTCGACT TGCCATGTGT ATGTGGGTAC | 6899 |
| 3' XbaI F30 primer | CGCTCTAGAT TGCCATGAAT GATCCCGAAG G | 6897 |
| 5' T7 promoter 5S primer | GCCGGATCCT AATACGACTC ACTATAGTCT ACGGCCATAC CACCC | 6898 |

Figure 15:
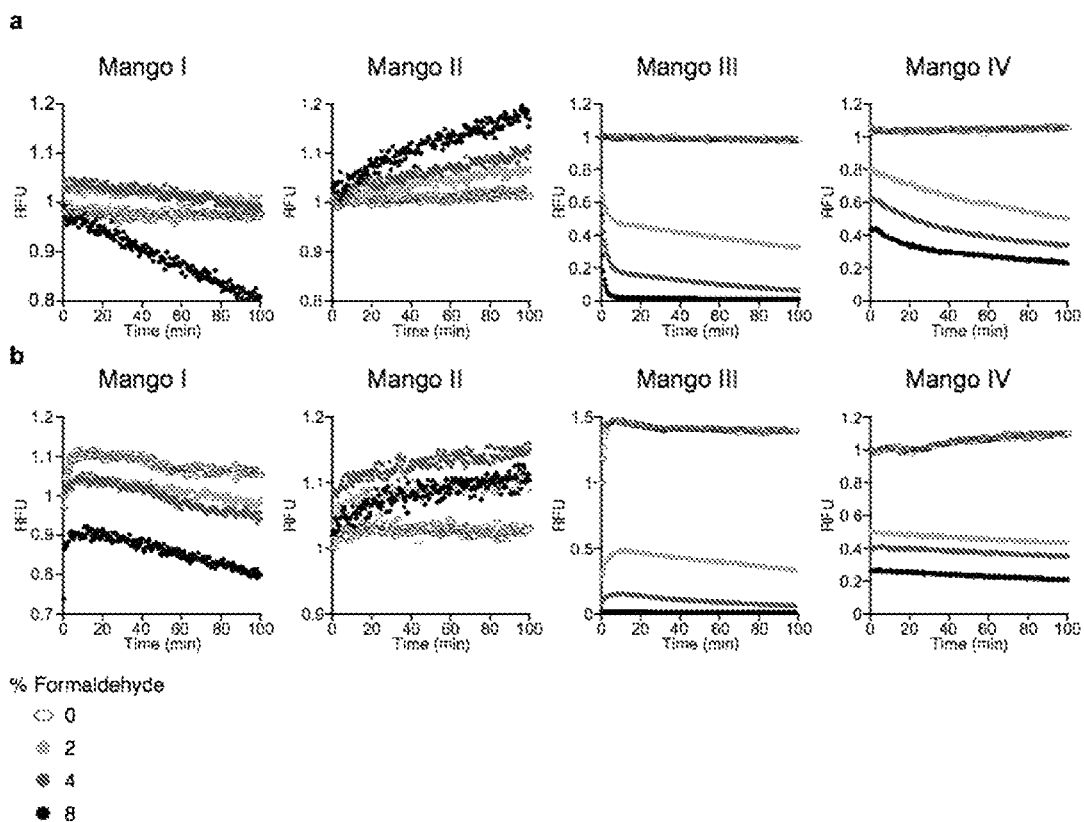

FIG. 15|Effect of formaldehyde on Mango fluorescence. Fluorescence of 50 nM RNA Mango I, II, III, and IV with 100 nM TO1-Biotin are measured at 30 second intervals at 25° C. In (a) RNA is first incubated with TO1-Biotin for one hour before addition of corresponding formaldehyde amounts and fluorescence is measured for another 100 minutes. In (b) RNA is incubated with the corresponding amounts of formaldehyde first for one hour, then TO1-Biotin is added. Data for each panel is normalized to RFU at the 0% formaldehyde, 0 min point.

Figure 16:
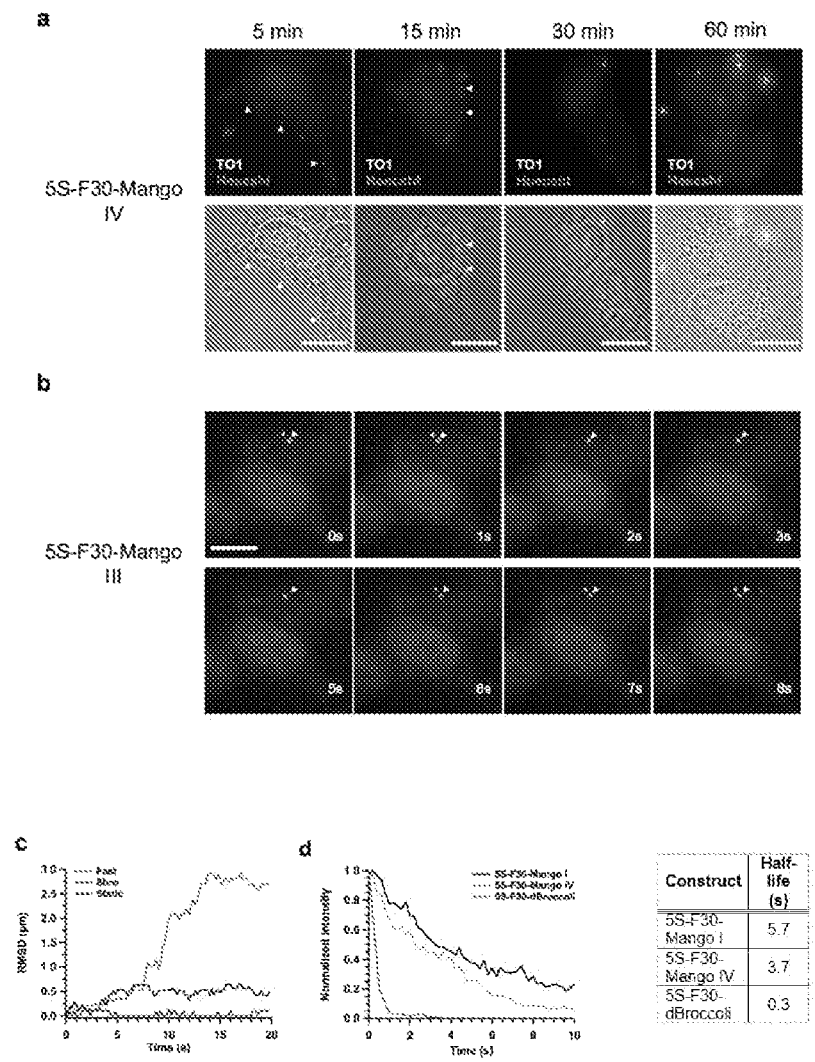

FIG. 16|Formation of 5S-Mango foci and their dynamics in live cells. (a) 5S-Mango IV imaged post cell fixation at 5, 15, 30 and 60 mins after transfection using Lipofectamine based CRISPRMAX transfection reagent. (b) Live-cell imaging of 5S-Mango IV 60 mins post transfection and the RNA was pre-incubated with TO1-Biotin prior to transfection. (c) Root mean-squared displacement (RMSD) of three observed foci with different diffusive behaviors, fast (Green), slow (Blue) and static (Red) shown in Video 3. Scale bars are 10 μm and arrows indicate foci of interest. (d) Normalized photobleaching traces of 5S-F30-Mango I and IV compared to 5S-F30-dBroccoli under constant illumination with an exposure time of 200 ms. Photobleaching half-lives are stated in the table adjacent and were calculated from an exponential fit of each curve.

Figure 17:
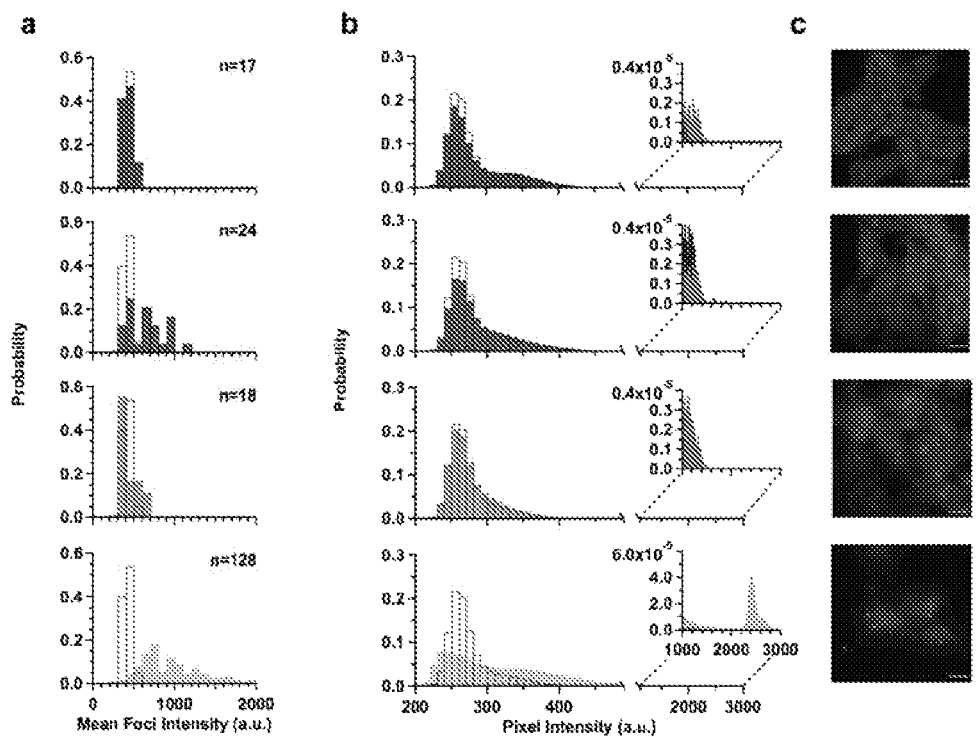

FIG. 17|Intensity Distributions of 5S-Mango I-IV. (a) Mean intensity distributions for 5S-F30-Mango I (Black), II (Blue), III (Green) and IV (Orange) foci compared with the 5S-F30-Control foci distribution (Red). Foci were determined using a diameter threshold 3×3 pixels in the ICY spot detector plugin. Number of foci for the mango tagged datasets shown as n. (b) Total pixel intensity distributions for 5S-Mango I-IV foci compared with the total 5S-F30-Control pixel intensities. Inset depicts the low frequency of high intensity pixels observed for each construct. (c) Representative maximum projections of fixed cells transfected with 5S-F30-Mango I-IV (top to bottom). Scale bars are 10 µm, stained with 1 µg/ml Hoechst 33258 (Blue) and 200 nM TO1-Biotin (Yellow).

Figure 18:
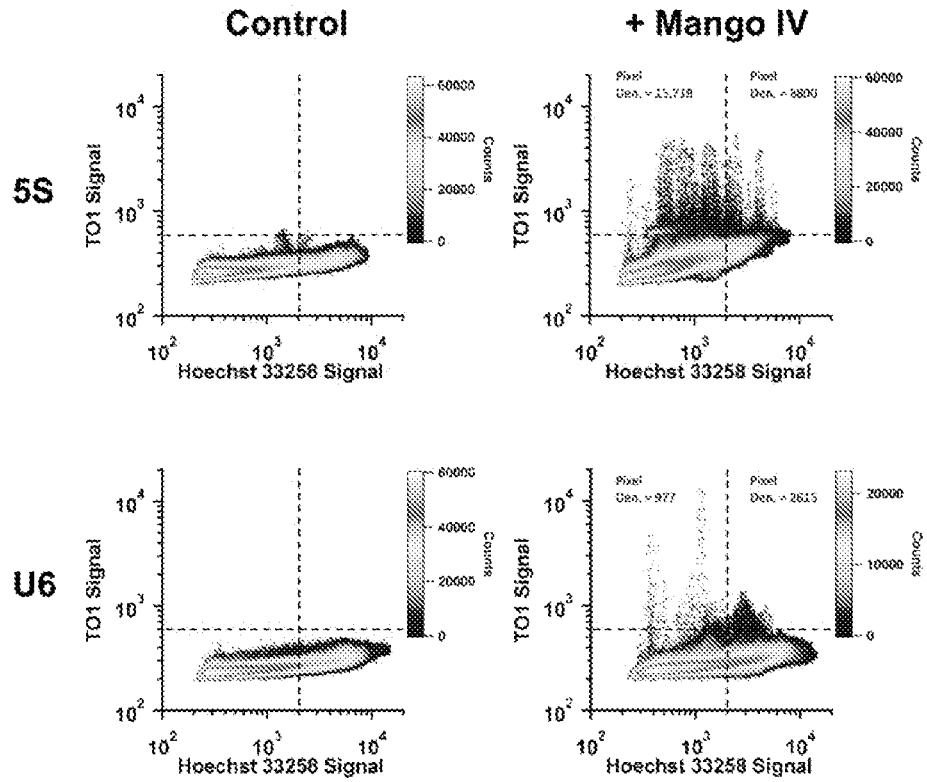

FIG. 18|2D nuclear co-localization plots. Pixel by pixel intensity plots of the TO1-Biotin signal (200 nM) vs Hoechst 33258 signal (1 µg/ml) for both 5S-Mango IV and U6-Mango IV compare to their respective controls in fixed cells. For the Mango specific signal a threshold was set above the 5S-F30-Control background of 600 a.u. Whereas the threshold of the nuclear boundary is observed to be ~2000 a.u. based on Hoechst 33258 staining. The upper quadrants highlight the number of pixels contain within and therefore depict pixels observed outside (upper left) or inside the nucleus (upper right). Each plot contained five maximum projection images with dimensions 1280×1280. The number of cells for 5S-F30-Control, 5S-F30-Mango IV,U6-Control and U6-Mango IV were 57, 114, 131 and 183 respectively.

Figure 19:
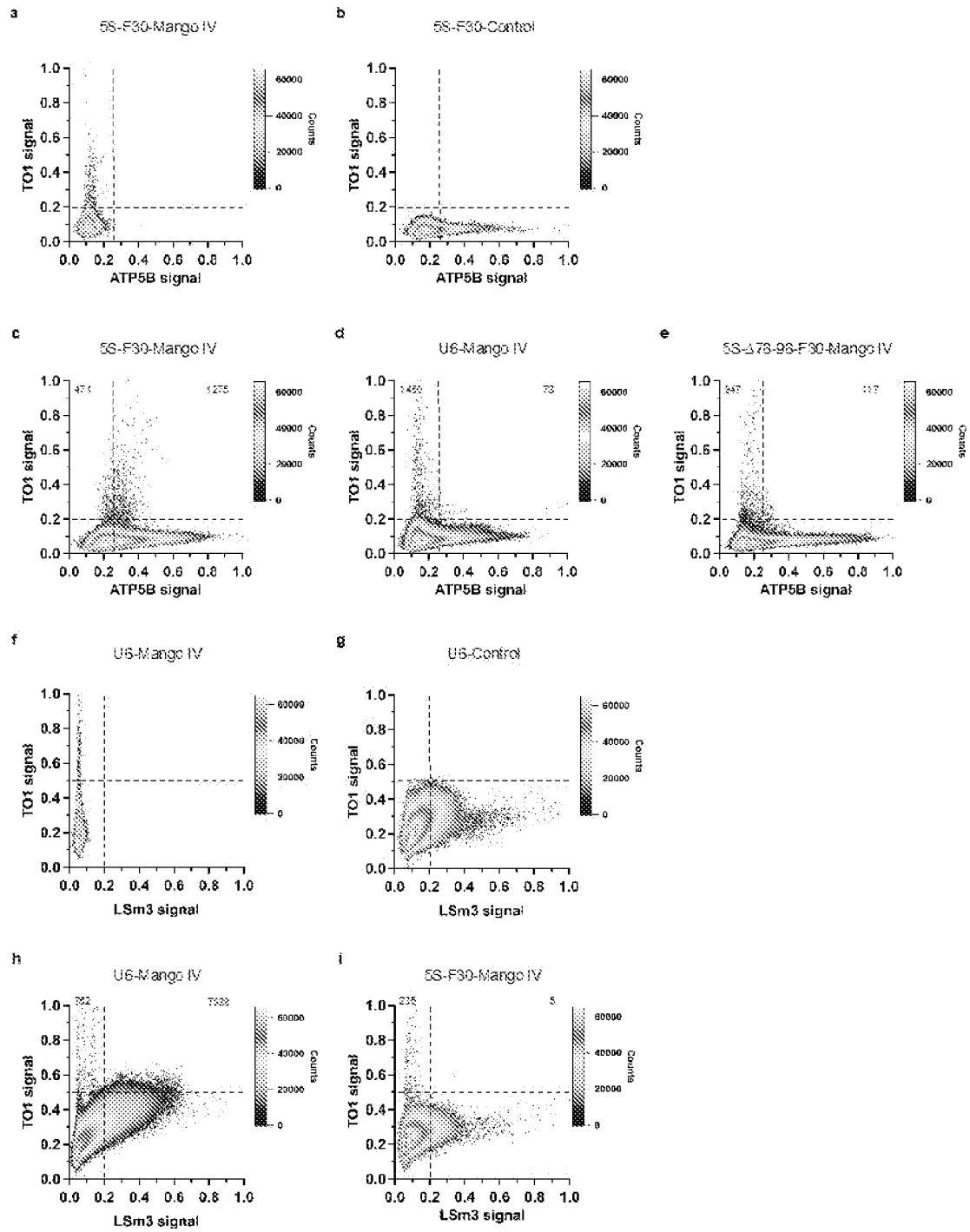

FIG. 19|2D immunostaining co-localization plots. Normalized pixel by pixel intensity plots of the TO1-Biotin signal vs immunostaining signal for both Mitochondria (ATP5B, a-e) and snRNPs (LSm3, f-i). Background intensity values were determined either with a Mango IV tagged construct in the absence of immunostaining or a control construct in the presence of both TO1-Biotin and the appropriate immunostain (a, b, f and g). All plots were normalized by subtracting the background signal in each channel and then normalizing to the highest significant pixel intensity from each of the channels. (c-e) Show the co-localisation patterns of Mango tagged 5S, U6 and 5S Δ78-98 with Mitochondria. (h and i) Show co-localisation patterns of Mango tagged U6 and 5S with snRNPs. The upper quadrants highlight the number of pixels contained within and therefore depict the co-localised (upper right) and distinct (upper left) Mango signal. Each plot contains multiple slices taken from ~five images with dimensions 1280×1280 to accurately determine co-localizing pixels. The number of cells for plots a, b, c, d and e were 66, 26, 178, 217 and 156 respectively. The number of cells for plots f, g, h and i were 34, 108, 165, and 89 respectively.

FIG. 20|Bipartite aptamer systems. This schematic illustration shows the Mango core as a loop, flanked by regions that are complementary to a target RNA of interest.

FIG. 21|Initial screening to find optimal "switch" and the "trigger" constructs for RNA Mango I based bipartite detection system. Looped line is the core Mango I G-quadruplex "GGG AC GGUG C GGAG A GGAG (SEQ ID NO: 1)"; sequences of Mango bait and RNA targets are set out.

FIG. 22|Bipartite mango probes for β-actin mRNA. (A) Model for β-actin mRNA transport, mRNA synthesized in the nucleus binds to Zipcode binding protein (ZBP1) which then associates with other proteins to bind to actin. The RNP then translocates to the leading edge of lamellipodia. (B). Fluorescence response of Mango I constructs that target β-actin mRNA. The Bipartite switch (50 nM) was added (at 10 min) to (100 nM) TO1-B. After 60 mins, the complementary in vitro transcribed 'trigger' RNA (100 nM) was added. (C) shows the sequence of the probe and the target sequences used.

FIG. 23|Bipartite construct with Mango II and 4 bp inhibitory stem. (A and B) Schematic representation of Mango II construct without inhibitory stem (MII) and with inhibitory stem (MII +4i). (C) Fluorescence response of the biparite constructs. The Bipartite switch (50 nM) was added (at 10 min) to (100 nM) TO1-B. At 70 mins, the complementary in vitro transcribed 'trigger' RNA (100 nM) was added. Right—Table showing the contrast of bipartite constructs with and without inhibitory stem.

FIG. 24|Effect of inhibitory stem length on contrast and rate of fluorescence emergence. (A) The number associated with the MII annotation refers to the number of interfering nucleotides. The Bipartite switch (50 nM) was added (at 20 min) to (100 nM) TO1-B. After 80 mins, the complementary in vitro transcribed 'trigger' RNA (100 nM) was added. (B) Sequences of the constructs used in the panel (A). In bold are potentially base pairing nucleotides that destabilize the G-quadruplex in the absence of trigger (target RNA).

FIG. 25|Schematic illustration of a generalized RNA Mango-based bipartite construct targeted to an RNA of interest.

FIG. 26|Mango IV based bipartite constructs alignment.

FIG. 27|Mango IV based bipartite construct measured contrast levels.

FIG. 28|Sequences of Mango switch probe used. Probe sequence shown 5' to 3' followed immediately by the complementary target shown 3' to 5'. Mango I core sequence shown in purple, Mango II core sequence shown in blue.

Figure 29:
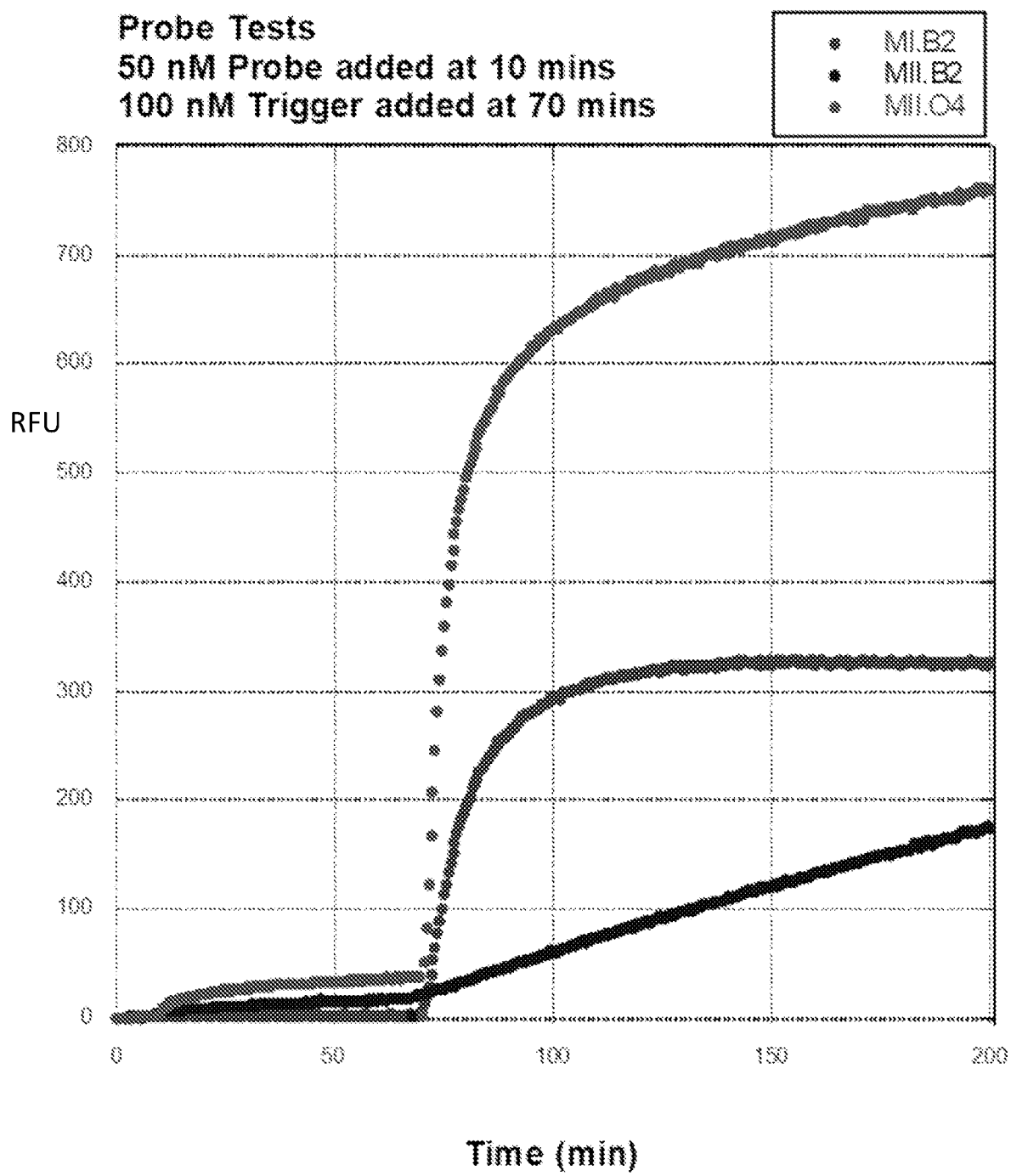

FIG. 29|Time course of in vivo Mango I & II switch probes. 140 mM potassium chloride, 1 mM magnesium chloride, 10 mM sodium phosphate buffer (pH 7.2), and 100 nM TO1-biotin was incubated at 25° C. for 5 min before the addition of probe to a final of 50 nM. After 60 min incubation, a short complementary trigger strand was added to a final of 100 nM. Fluorescence excitation at 510 nm and emission read at 535 nm.

Figure 30:
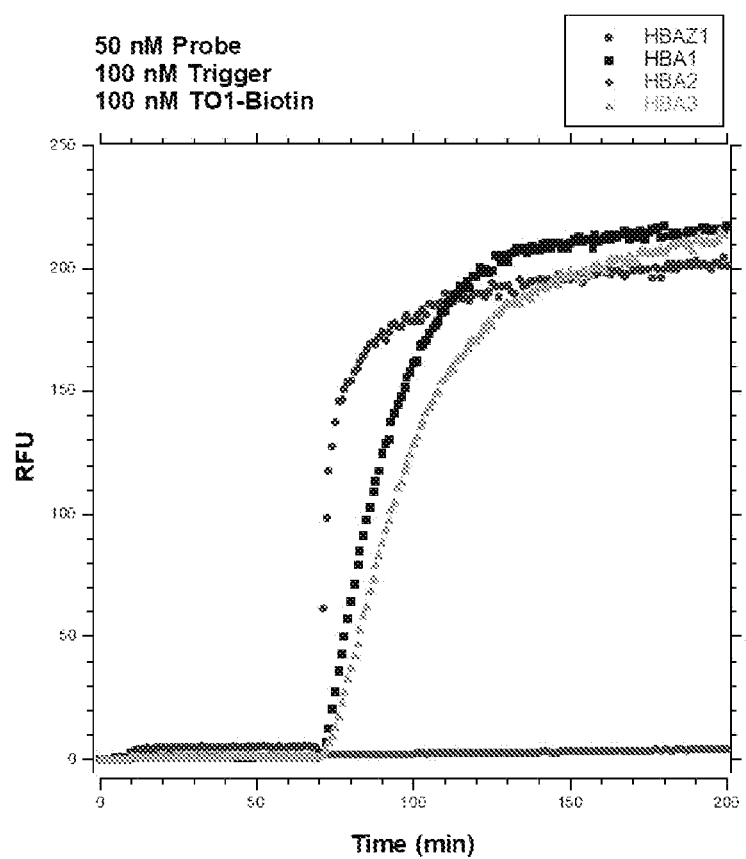

FIG. 30|Time course of in vivo Mango switch probes. 140 mM potassium chloride, 1 mM magnesium chloride, 10 mM sodium phosphate buffer (pH 7.2), and 100 nM TO1-biotin was incubated at 25° C. for 5 min before the addition of probe to a final of 50 nM. After 60 min incubation, a short complementary trigger strand was added to a final of 100 nM. Fluorescence excitation at 510 nm and emission read at 535 nm. Before trigger corresponds to t=69 min, after trigger t=200 min, C=after trigger/before trigger.

Figure 31:
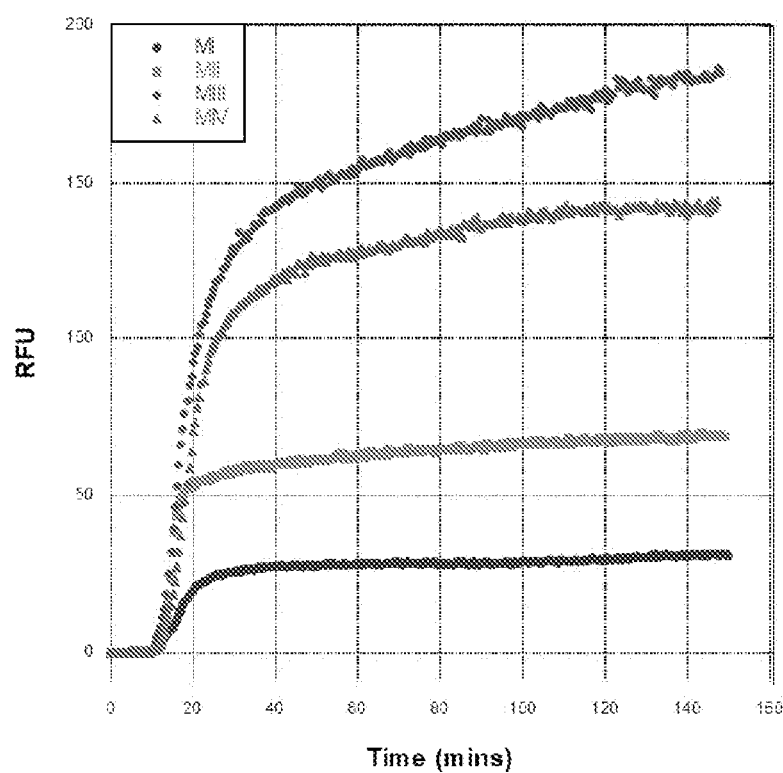

FIG. 31|T7 transcription of all unimolecular templates. Assay performed in 40 mM Tris pH 7.9, 2.5 mM spermidine, 26 mM MgCl$_2$, 0.01% triton X-100, 140 mM KCl, 0.5 µM DNA template, 200 nM TO1-Biotin, 10 mM DTT, 0.5 µM T7 promoter compliment strand, 0.3 U/600 µL pyrophosphatase (Invitrogen), 8 mM GTP, 5 mM CTP, 2 mM UTP, 5 mM ATP. At t=10, 30 µL/600 µL reaction diluted T7 enzyme was added.

Figure 32:
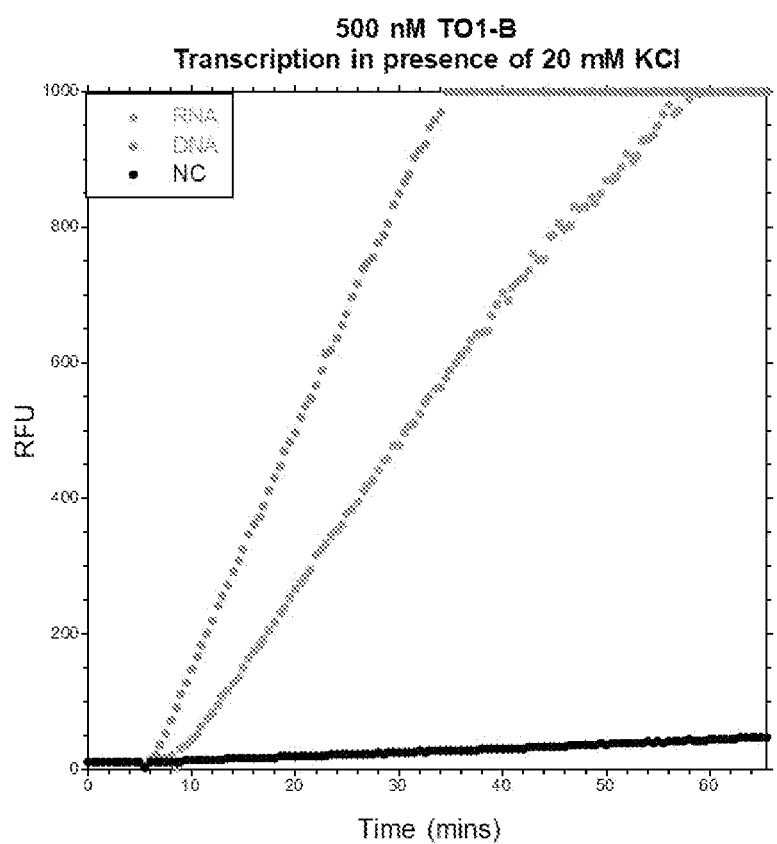

FIG. 32|Rolling circle transcription of Mango III. T7 RNA polymerase added to supplemented mixture at 5 min 30 sec. Fluorescence excitation at 510 nm and emission at 535 nm. Orange: RNA target with oligo ligated with SplintR Ligase (NEB), Blue: DNA target with oligo ligated with T4 DNA Ligase (NEB).

Figure 33:
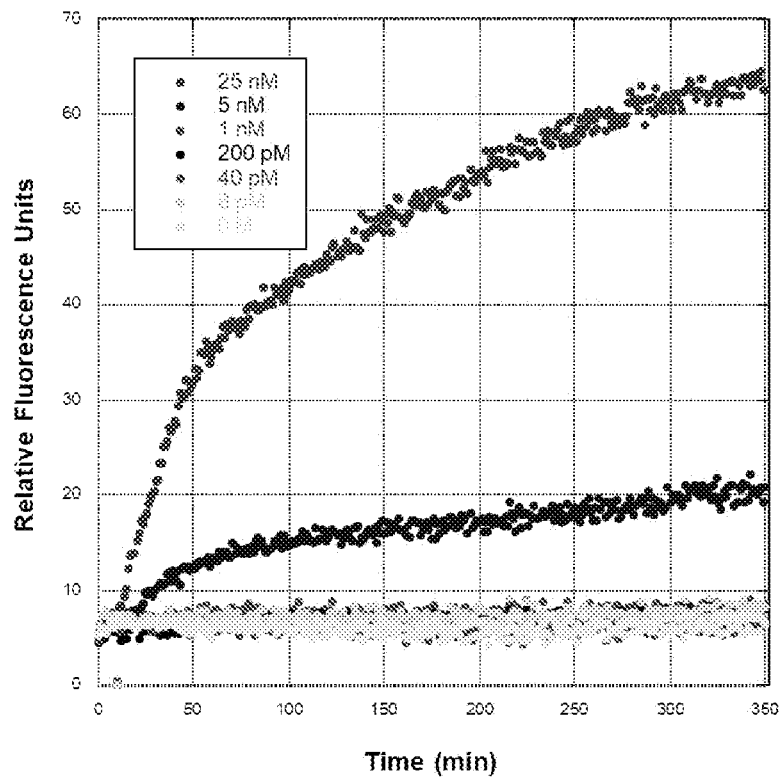

FIG. 33|Rolling circle transcription of Mango III. Circular template (represented in FIG. 34), was titrated and room temperature T7 transcription was initiated in the presence of excess of TO1-Biotin fluorophore.

Figure 34:
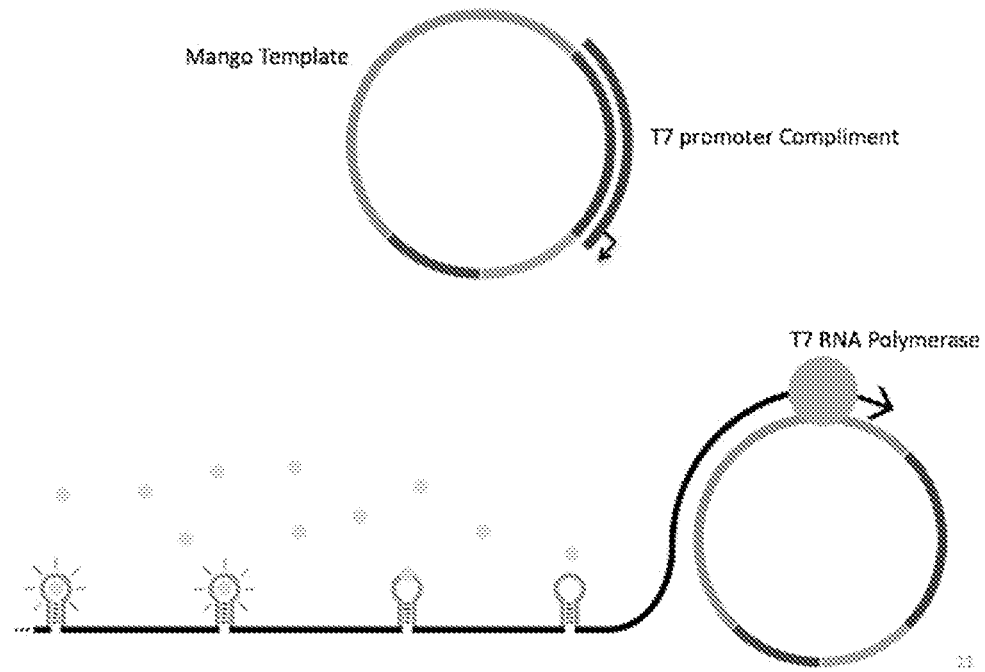

FIG. 34|Rolling circle transcription of Mango III. Circular construct represented here was used in FIG. 33. Purple: T7 binding site, red and orange template hybridization arms (ligation site between them). Blue Mango sequence. T7 transcription of this DNA template results in multiple Mango repeats that once formed are able to bind TO1-Biotin (yellow hexagons) and fluoresce.

Figure 35:
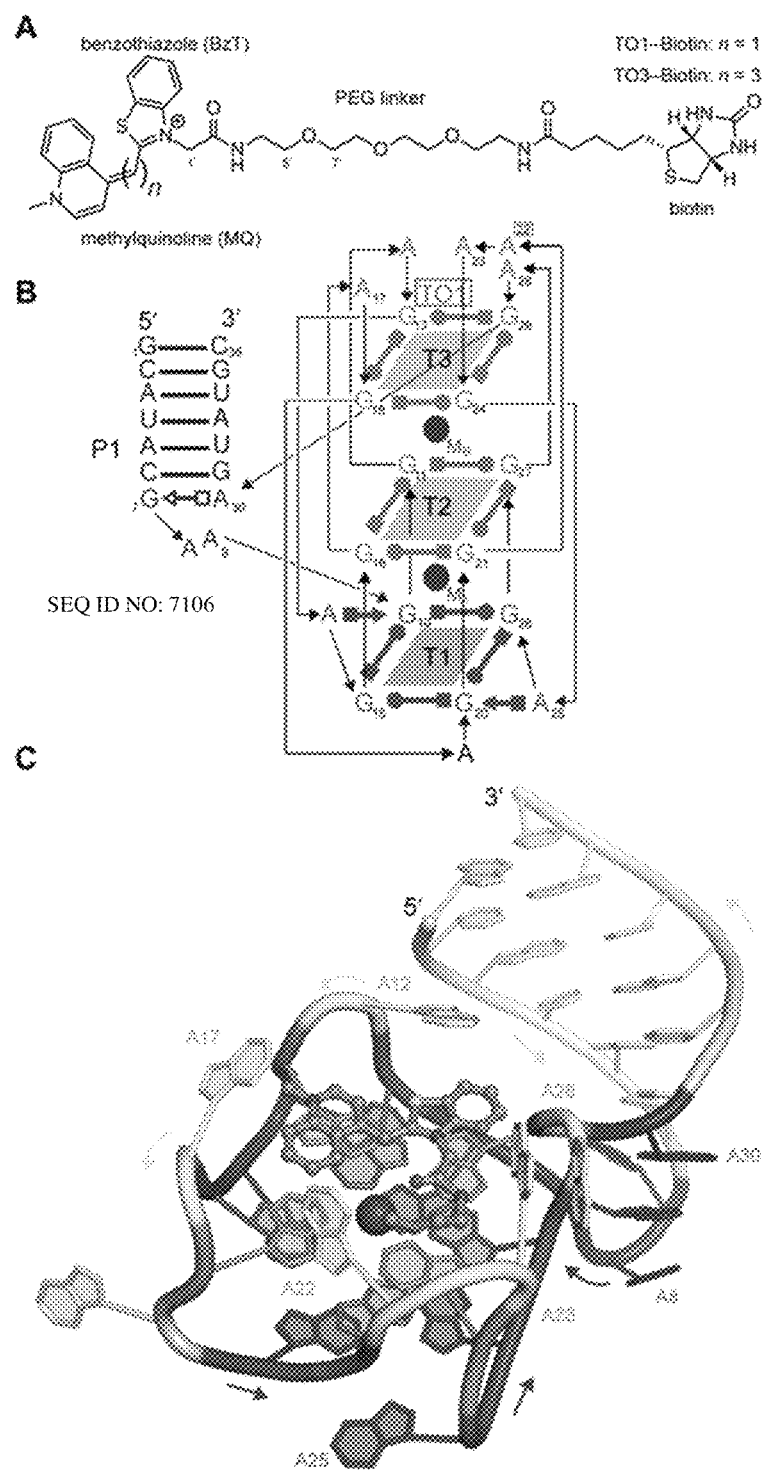

FIG. 35|Structure of Mango-II in complex with TO1-Biotin. (A) Chemical structures of TO1-Biotin and TO3-Biotin. The latter contains two additional methine carbons. (B) Secondary structure of the Mango-II-TO1-Biotin complex. Thin lines with arrows denote connectivity. Base pairs are represented with Leontis-Westhof symbols.[11] Location of fluorophore and two potassium ions (TO1, $M_A$, and $M_B$) is indicated. This color scheme is used throughout the manuscript except where noted. (C) Cartoon representation of the Mango-II-TO1-Biotin complex. Arrows adjacent to the cartoon denote chain direction.

Figure 36:
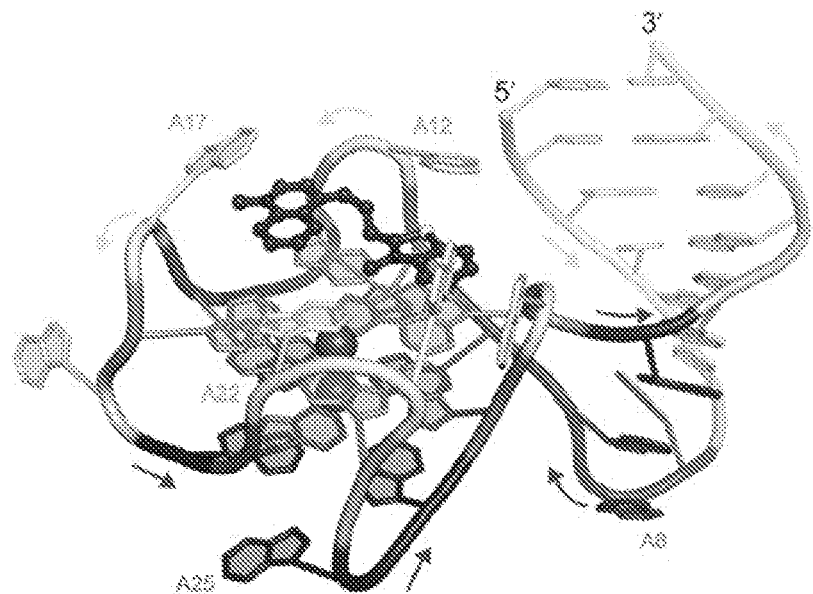

FIG. 36|Structure of the Mango-II-TO3-Biotin complex. Cartoon representation of chain A of the Mango-II-TO3-Biotin complex. Color scheme is the same as FIG. 1C with the exception of TO3-Biotin colored as red sticks FIG. 37|Analytical ultracentrifugation of Mango-II-TO1-Biotin complex.

Figure 38:
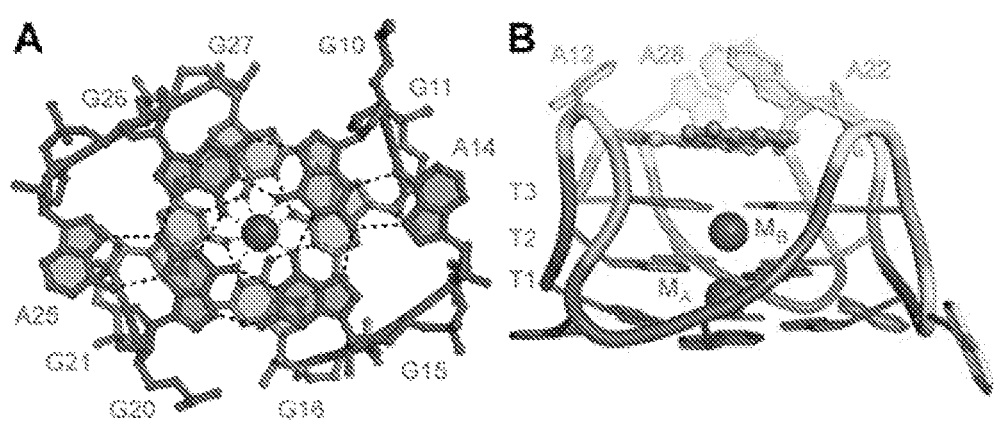

FIG. 38|The Mango-II G-quadruplex. (A) Augmented Tier 1 (T1, purple) and Tier 2 G-quartets (T2, blue) of the Mango-II-TO1-Biotin complex. T1 is augmented into a hexad. (B) Side view.

Figure 39:
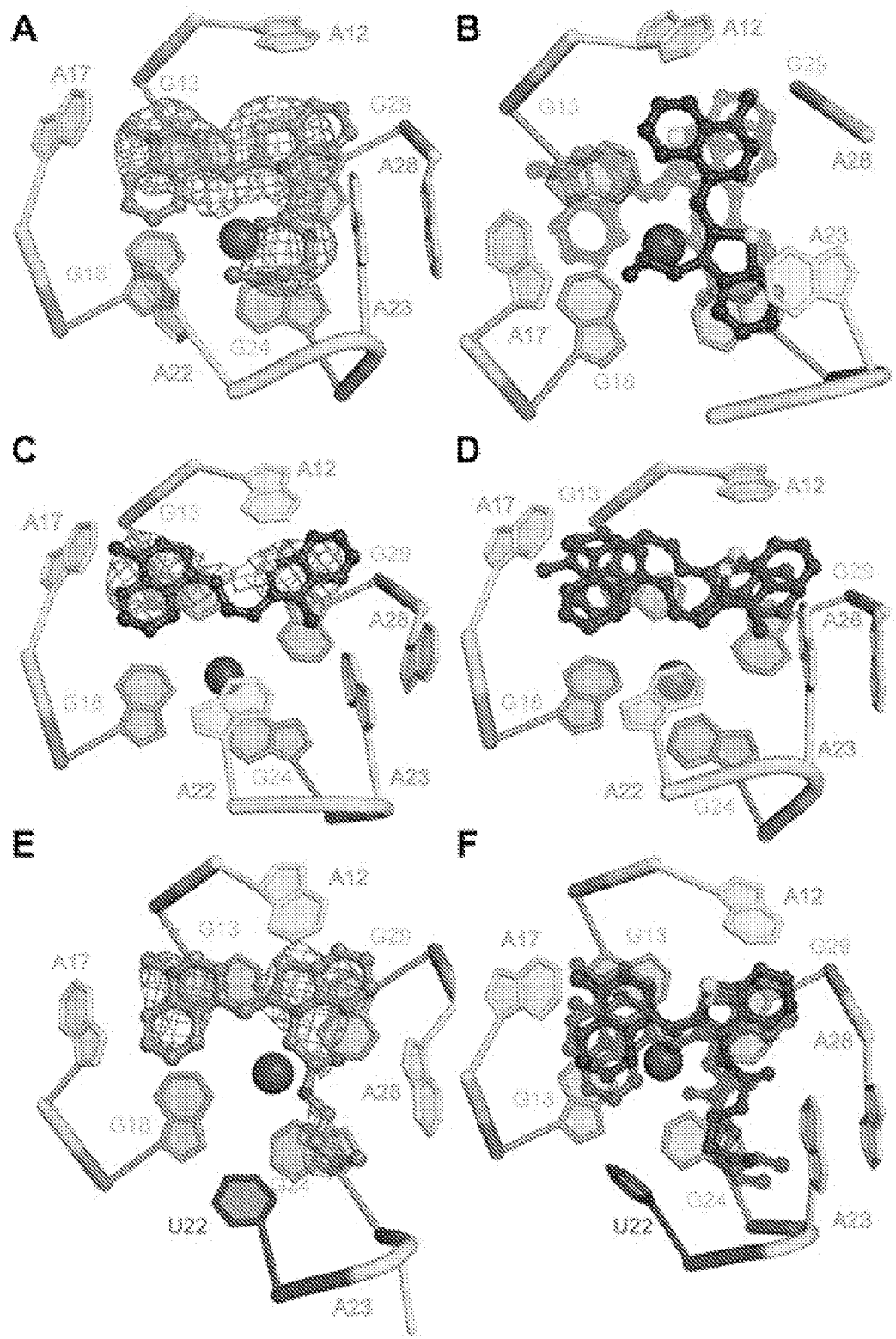

FIG. 39|Plasticity of the Mango-II ligand binding pocket. (A) Cartoon representation of the ligand binding pocket of chain A of the Mango-II-TO1-Biotin complex structure, with fluorophore electron density (2|Fo|−|Fc| prior to building the ligand, contoured at 1.2 σ, blue mesh) shown in mesh. (B) Overlay of the fluorophores from the three complexes in the asymmetric unit aligned on chain C. TO1-Biotin from chains A, B, and C are shown in transparent red, transparent purple and blue, respectively. In chain C, A22 and A28 are disordered. (C) Fluorophore electron density (2|Fo|−|Fc|) prior to building the ligand, contoured at 1.2 σ, blue mesh) for chain A of the Mango-II-TO3-Biotin complex structure. (D) Overlay of the ligands in chain A (purple) and chain B (red). The chain A RNA is shown. (E) Cartoon representation of the ligand binding pocket of chain B of the Mango-II (A22U)-TO1-Biotin complex Fluorophore electron density (2|Fo|−|Fc| prior to building the ligand, contoured at 1.2 σ) blue mesh. (F) Overlay of the ligands in chains A, B and C (purple, blue and red, respectively). Chain A RNA shown.

Figure 40:
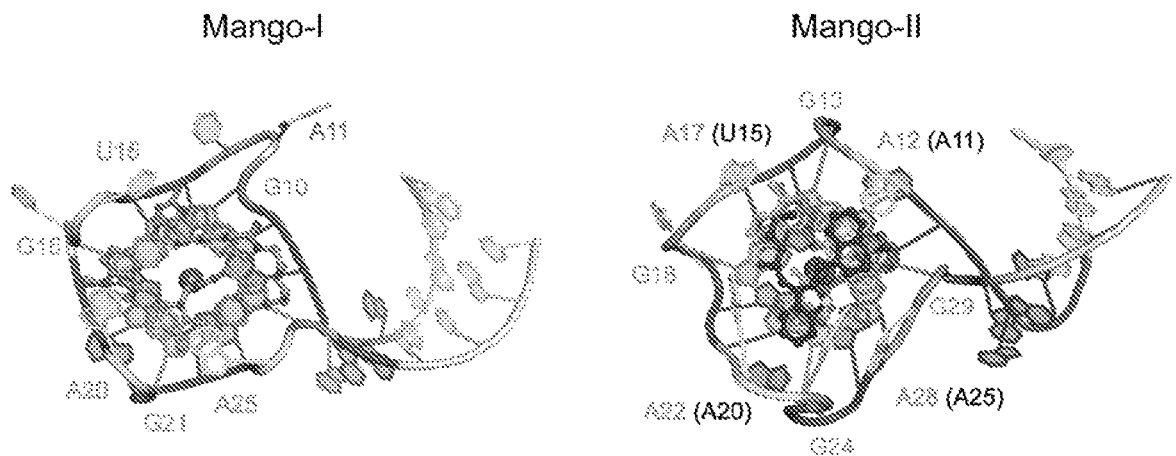

FIG. 40|Structural comparison of the Mango-I-TO1-Biotin complex and the Mango-II-TO1-Biotin complex. Side by side comparison of Mango-I-TO1-Biotin (left) and Mango-II-TO1-Biotin (right) showing distinct, unequivalent conformations of the TO1-Biotin ligand in each structure.

Figure 41:
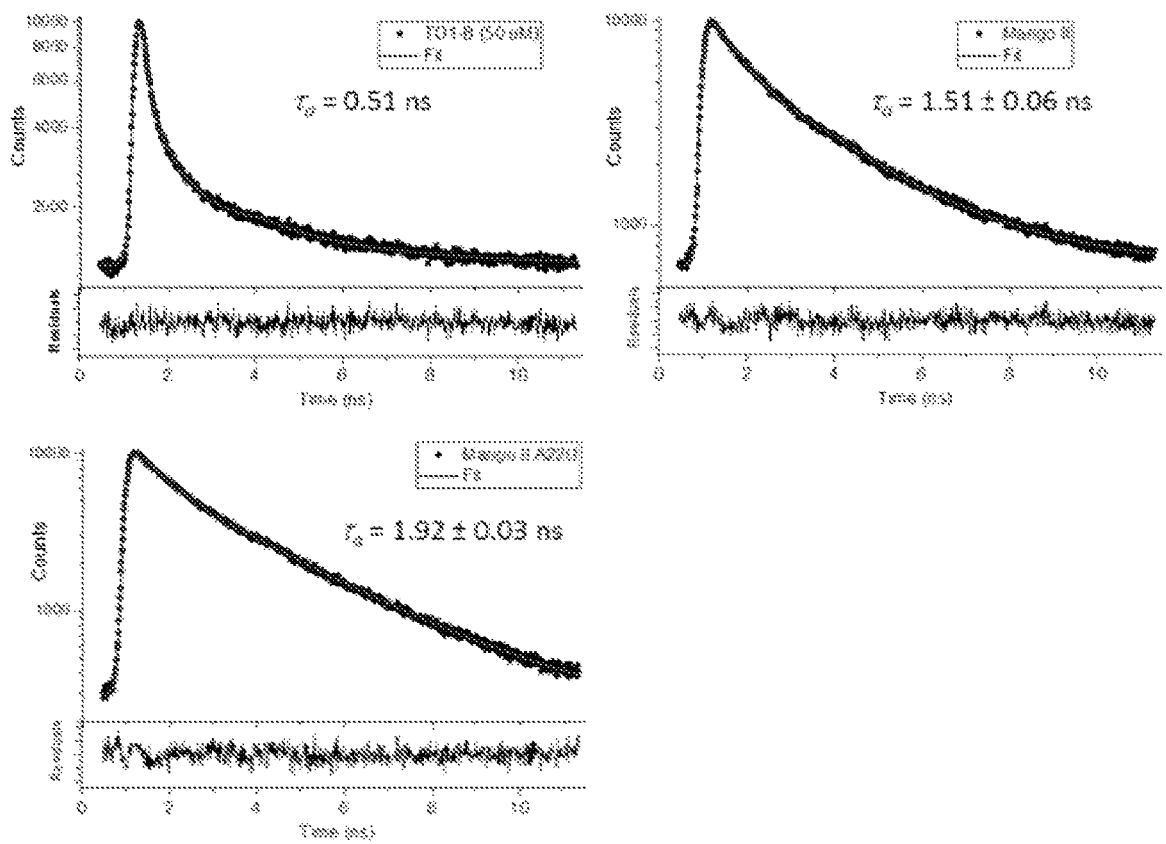

FIG. 41|Fluorescence lifetime traces of TO1-Biotin, Mango-II wt and A22U with TO1-Biotin. Comparison of the lifetime decay obtained from TO1-B free in solution (left panel), and when bound to Mango II wt (central panel), or Mango II A22U (right panel). In each panel the data are presented as filled circles, the red line shows the fit to the data, reconvoluted with the IRF, and underneath the data the residuals from the fit are shown. On each panel, the intensity-weighted average lifetime is reported. For details about the individual lifetime components and their amplitudes.

Figure 42:
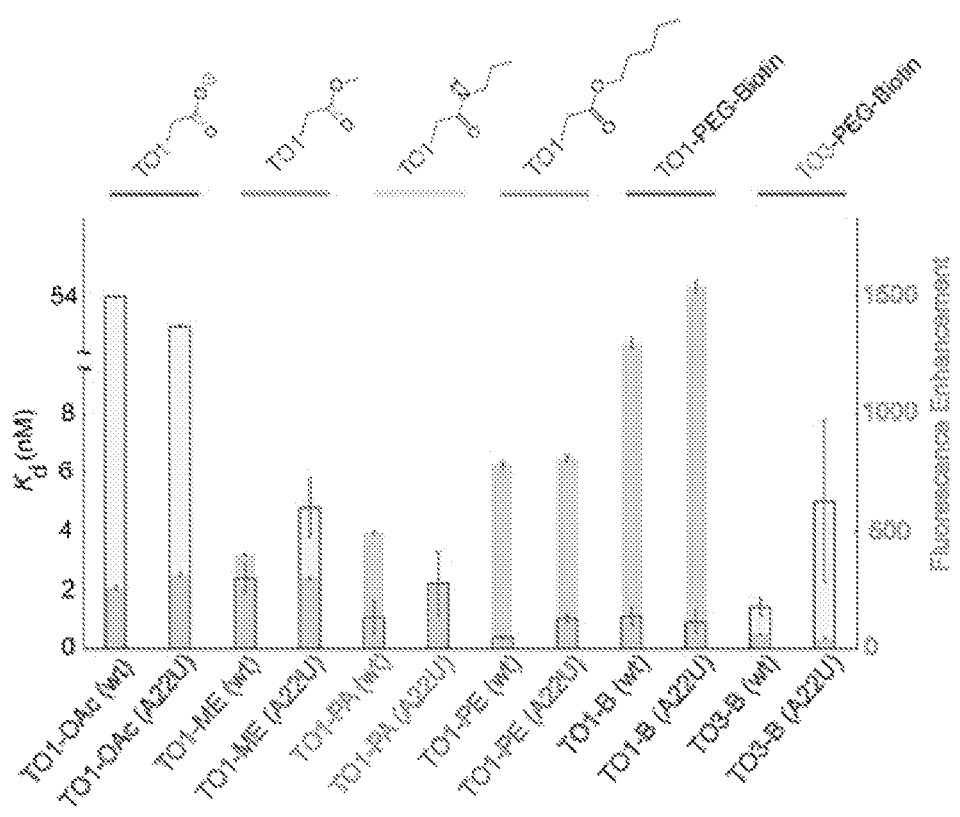

FIG. 42|Mango-II binding and fluorescence enhancement of thiazole orange derivatives. Dissociation constants, Kd, and fluorescence enhancement, (gray and green bars, respectively) for various TO1-Biotin derivatives. Length of the linker between TO1 and biotin increases from left to right.

Figure 43:
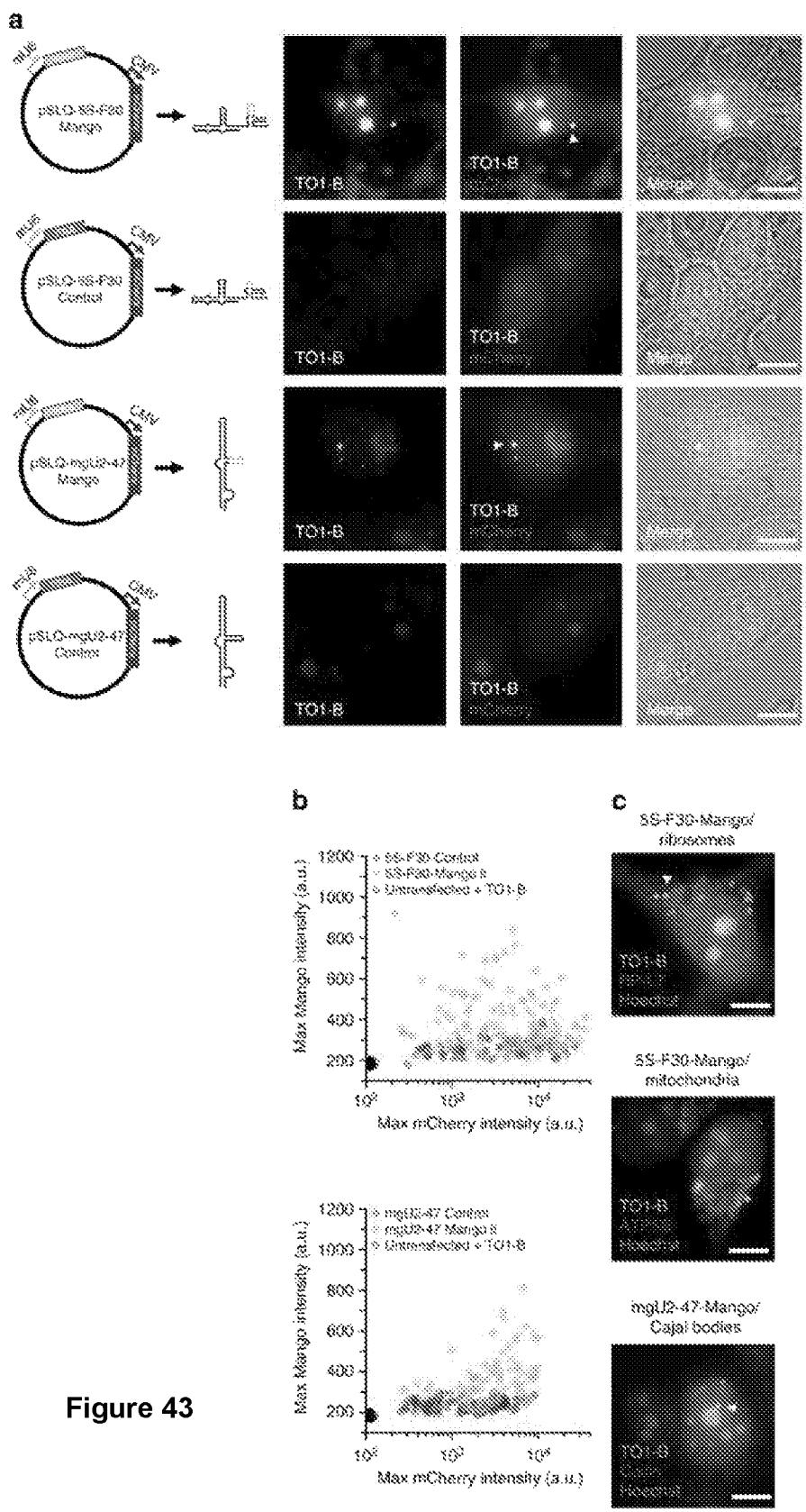

FIG. 43|Fluorogenic RNA Mango aptamers for imaging small non-coding RNAs in mammalian cells. Cellular imaging of genetically encoded Mango II-tagged RNAs. a) Diagram of plasmid constructs with the 5S rRNAs and mgU2-47 scaRNAs under the control of a murine U6 promoter (Pol III) and co-expression of a mCherry reporter gene (CMV promoter). Shown adjacent are images of individual slices of fixed cells either expressing Mango II-tagged RNAs (top) or control RNAs (bottom) with the TO1-B (200 nM) signal in yellow, mCherry in red and brightfield image in greyscale. Arrows depict significant cellular and nuclear foci. Scale bar=10 μm. b) 2D maximum intensity plots of individual nucleoli and Mango II specific foci for both the TO1-B signal (y axis) and mCherry signal (x axis—log 10 scale). The number of cells for 5S-F30-Control, 5S-F30-Mango II, untransfected cells+TO1-B, mgU2-47 Control and mgU2-47 Mango II were 89, 167, 98, 130 and 117 respectively. c) Maximum projections of cytoplasmic 5S-F30-Mango IV foci and nuclear mgU2-47 foci from plasmid expression in conjunction with immunostained ribosomes (RP-L7), mitochondria (ATP5B) and Cajal bodies (Coilin). Arrows depict significantly co-localized foci, scale bar=10 μm FIG. 44|Crystal contacts of the Mango-III-TO1-Biotin Complex FIG. 45|Analytical Ultracentrifugation of the Mango-III-TO1-Biotin FIG. 46|Structure of the Mango-III-TO1-Biotin complex. a, Chemical structure of TO1-Biotin and TO3-Biotin. b, Secondary structure. Thin lines with arrowheads denote connectivity. Leontis-Westhof symbols denote base pairs. c, Cartoon representation of the three-dimensional structure of the complex colored as in (b). Arrows indicate 5' to 3' chain direction, and purple spheres represent $K^+$. d, Sequence alignment of Mango-I and Mango-III aptamer RNA cores colored as in (b). Lines depict base pairing, except for the G-Quadruplex (black lines). Co-varying nucleotide shaded gray.

Figure 47:
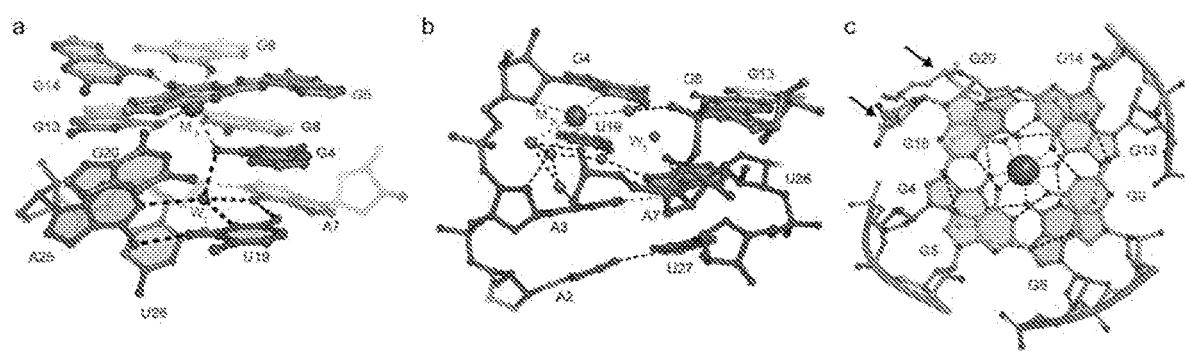

FIG. 47|Structure of the duplex-triplex-quadruplex junction. a, Base positions of T1, T2 and T3 as well as co-solvent interactions in the Mango-III core. U31, A30 and G25 are buckled and stacking on each other. A central water molecule ($W_1$) is represented with a red sphere and the central $K^+$ ion ($M_A$) is represented by a purple sphere. (b) Hydrated metal ion network (purple and red spheres) with hydrogen bonding interactions between P1 (red), T1 (purple) and T2

(marine) represented by black dashed lines. Inner-sphere metal ion coordination is represented by orange dashed lines. (c) Ball-and-stick representation of the T2 and T3 tiers and the central potassium ion $M_4$. Black and orange dashed lines represent hydrogen-bonding and inner-sphere cation coordination, respectively.

Figure 48:
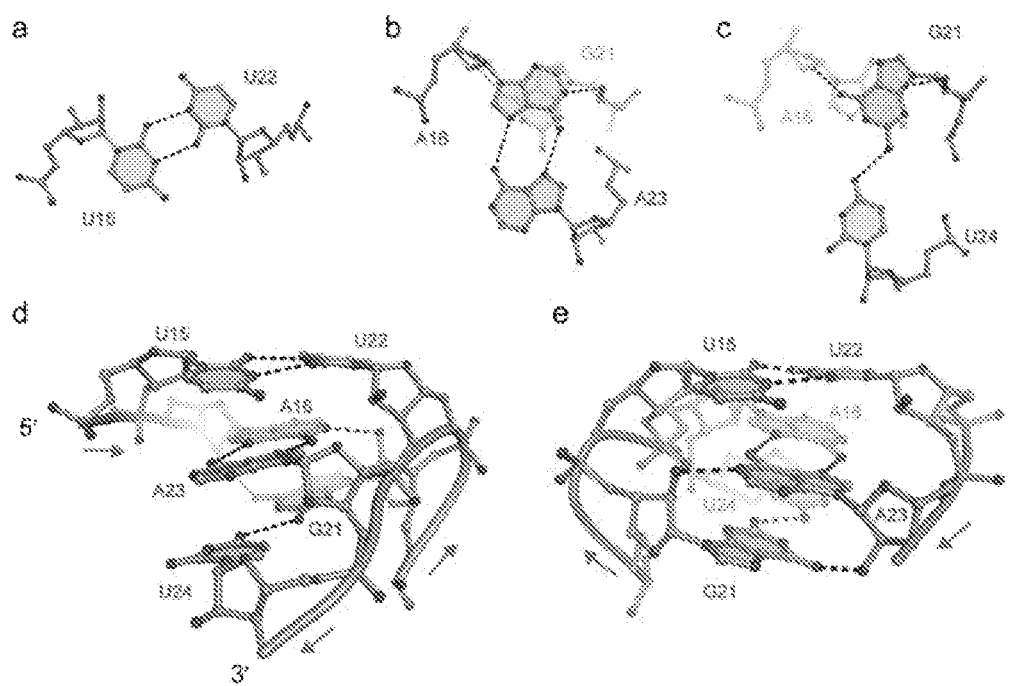

FIG. 48|Structure of the non-canonical P2 helix a, U15-U22 trans Watson-Crick base pair. b, A16•A23 trans Hoogsteen base pair. Dashed lines, hydrogen bonds. c, G21•U24 cis single-hydrogen bond base pair. G21 is shown to highlight cross-strand stacking. A16 is shown to highlight cross-strand stacking. d, View of P2 from the direction of the G21-U24 strand. Arrows denote 5'- to 3' chain direction. e, 180° rotation along a vertical axis.

Figure 49:
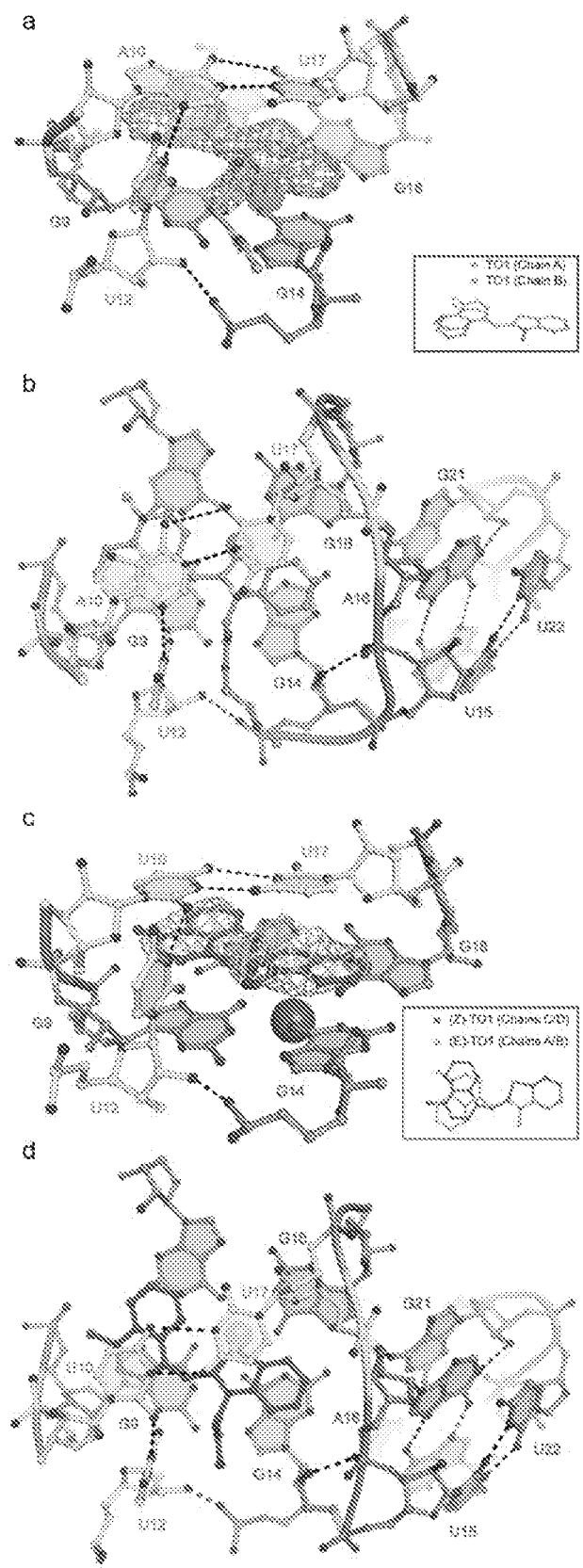

FIG. 49|Fluorophore binding by Mango-III. (a) Ball-and-stick representation of the ligand binding pocket superimposed on the $2|F_o|-|F_c|$ electron density map calculated before addition of ligand to the crystallographic model (grey mesh, 1.5σ contour). The native anomalous difference Fourier synthesis is shown as a solid green surface at 4σ contour. Inset shows the structural alignment of the TO1-Biotin fluorophores from each chain in the Mango-III(wt)-TO1-Biotin complex. (b) Top view of the Mango-III-TO1-Biotin binding-pocket and P2 (orange ball-and-stick). (c) Ball-and-stick representation of the ligand binding pocket of Mango-III(A15U)-TO1-Biotin complex superimposed on the $2|F_o|-|F_c|$ electron density map calculated before addition of ligand to the crystallographic model (grey mesh, 1.2σ contour). Inset shows the structural alignment of two TO1-Biotin fluorophores from each chains A and C of the Mango-III(A15U)-TO1-Biotin structure. (d) Top view of the Mango-III(A15U)-TO1-Biotin binding-pocket and P2 (orange ball-and-stick).

Figures 50, 51:
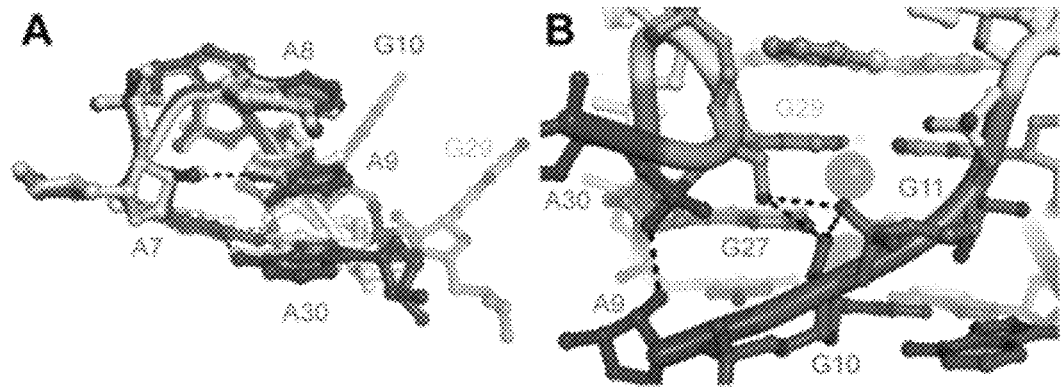

FIG. 50|Structure guided re-selection of 'Super-Mango-III'.

FIG. 51|Structure of the Mango-II helix junction. (A) Tetraloop like junction of Mango-II superimposed with a canonical GAAA tetraloop (PDB 4FNJ)*, RMSD 0.30 Å. (B) Adjacent region to the tetraloop junction showing stabilizing hydrogen bonding interactions.

FIG. 52|$\#_1$ and $\#_2$ Mutations and effect on binding and MIII construct brightness.

FIG. 53|Brightness response of MI, MII, MIII mutants and MIV to a fluorophore series. Single fluorescence point reads done in triplicate. 500 nM RNa was incubated with 10 nM fluorophore at room temperature for ~1 h to allow folding of the RNA aptamers in 1×WB (140 mM KCl, 1 mM $MgCl_2$, 10 mM $NaH_2PO_4$, pH 7.2.

DETAILED DESCRIPTION

Microfluidic Isolation of Mango Aptamers

Figure 1:
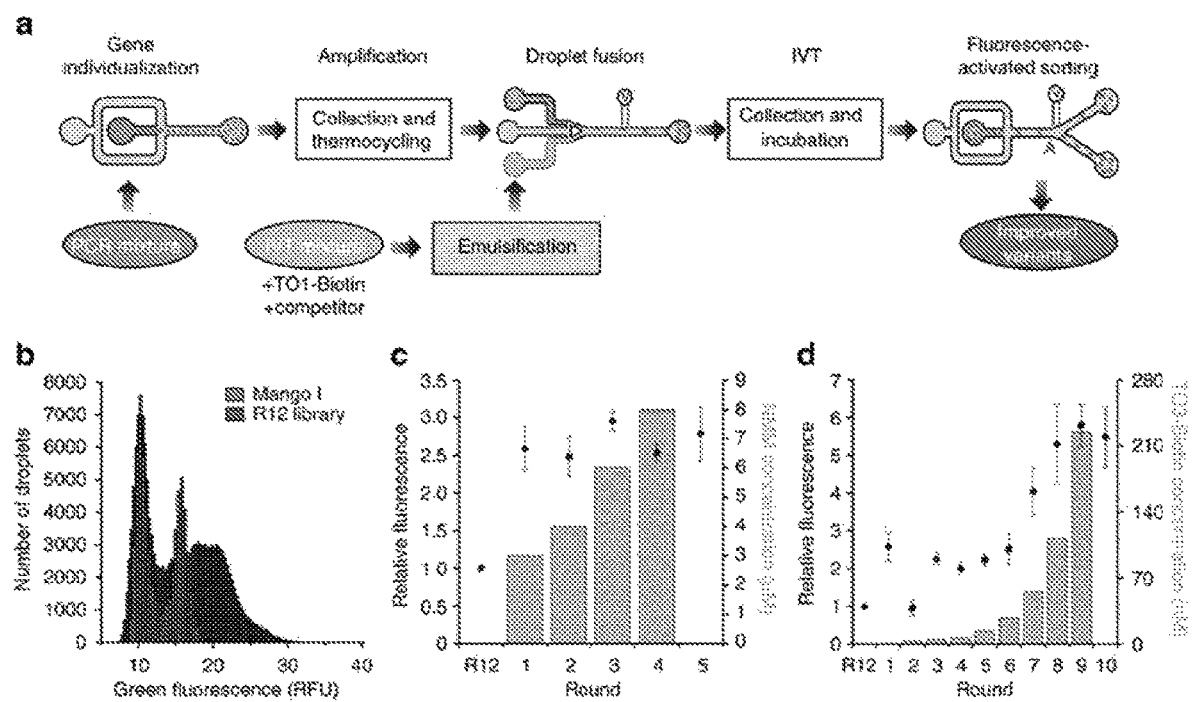
FIG. 1|Selection of TO1-Biotin binding variants using droplet-based microfluidics fluorescence screening in the presence of competitors. (a) Experimental workflow for microfluidic-assisted fluorescence screening. Ovals and boxes represent on- and off-chip steps, respectively. Three microfluidic devices were used for gene individualization in 2.5 pL droplets containing PCR mixture; after thermocycling, fusing each PCR droplet with a droplet containing an in vitro transcription (IVT) mixture supplemented with TO1-Biotin and competitor (NMM or TO3-Biotin); and, after incubation, the fluorescence profile of each droplet was analysed and sorted accordingly. (b) Fluorescence profile of droplets containing Mango I or the initial R12 library (~200,000 variants, Supplementary Table 1). Droplets containing no DNA yield a population of empty (initially) was found to have a fluorescence of 10 RFUs. (c) Improvement in fluorescence enhancement of aptamer libraries during the screening process in the presence of increasing amounts of NMM. The fluorescence (black dots) of the RNA libraries in complex with TO1-Biotin was determined by mixing 2 μM RNA and 100 nM TO1-Biotin in the absence of NMM. These values were normalized to that of the starting library (R12). (d) Enhancement in fluorescence resulting from selection with TO3-Biotin competitor. The fluorescence (black circles) was determined after each round by mixing 300 nM RNA and 100 nM TO1-Biotin in the absence of TO3-Biotin. The values were normalized to that of the starting library (R12). The blue bars represent the concentration of competitor used in each round of selection. For each sort, the gated populations can be found in FIG. 5.

As illustrated in FIG. 1, TO1-Biotin binding variants were selected using droplet-based microfluidics fluorescence screening in the presence of competitors. The fluorescence profile of droplets containing Mango-I of an initial library (~200,000 variants, designated R12) is shown in Table 3.

TABLE 3

Metrics of the fluorescence profiling of Mango and R12

| Round | Temperature (° C.) | TO-1 (nM) | λ value | Fusion efficiency (%) | Number of analyzed droplets | Number of analyzed variants |
|---|---|---|---|---|---|---|
| R12-library | 25 | 100 | 1.25 | 95 | 168,441 | 200,023 |
| Mango | 25 | 100 | 0.54 | 95 | 63,200 | 1 |

The microfluidic-assisted in vitro compartmentalisation (pIVC, FIG. 1a), shows that a significant fraction of molecules in the R12 library are brighter than Mango I (FIG. 1b).

Figure 4:
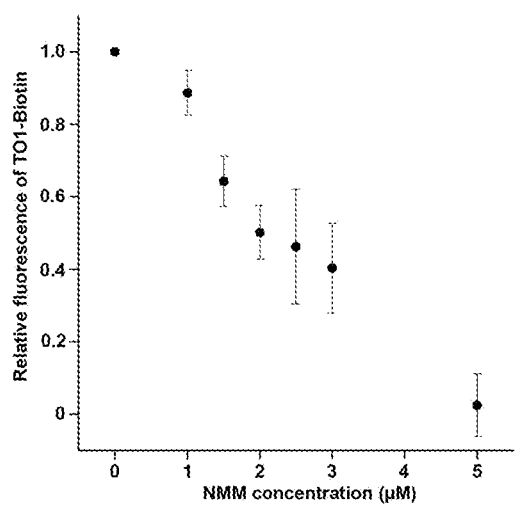
FIG. 4|Effect of N-methyl mesoporphyrin IX (NMM) concentration on TO1-biotin/Mango I fluorescence. RNA aptamer at 1 μM was incubated with 100 nM of TO1-Biotin and a concentration of NMM ranging from 0 to 5 μM·Green fluorescence was recorded (ex: 492 nm/em: 516 nm) in a real-time thermocycler (Mx 3005P, Agilent). Values are normalized to that of the 0 μM NMM point and are the mean of two independent experiments and error bars correspond to ±1 standard error.
Figure 5:
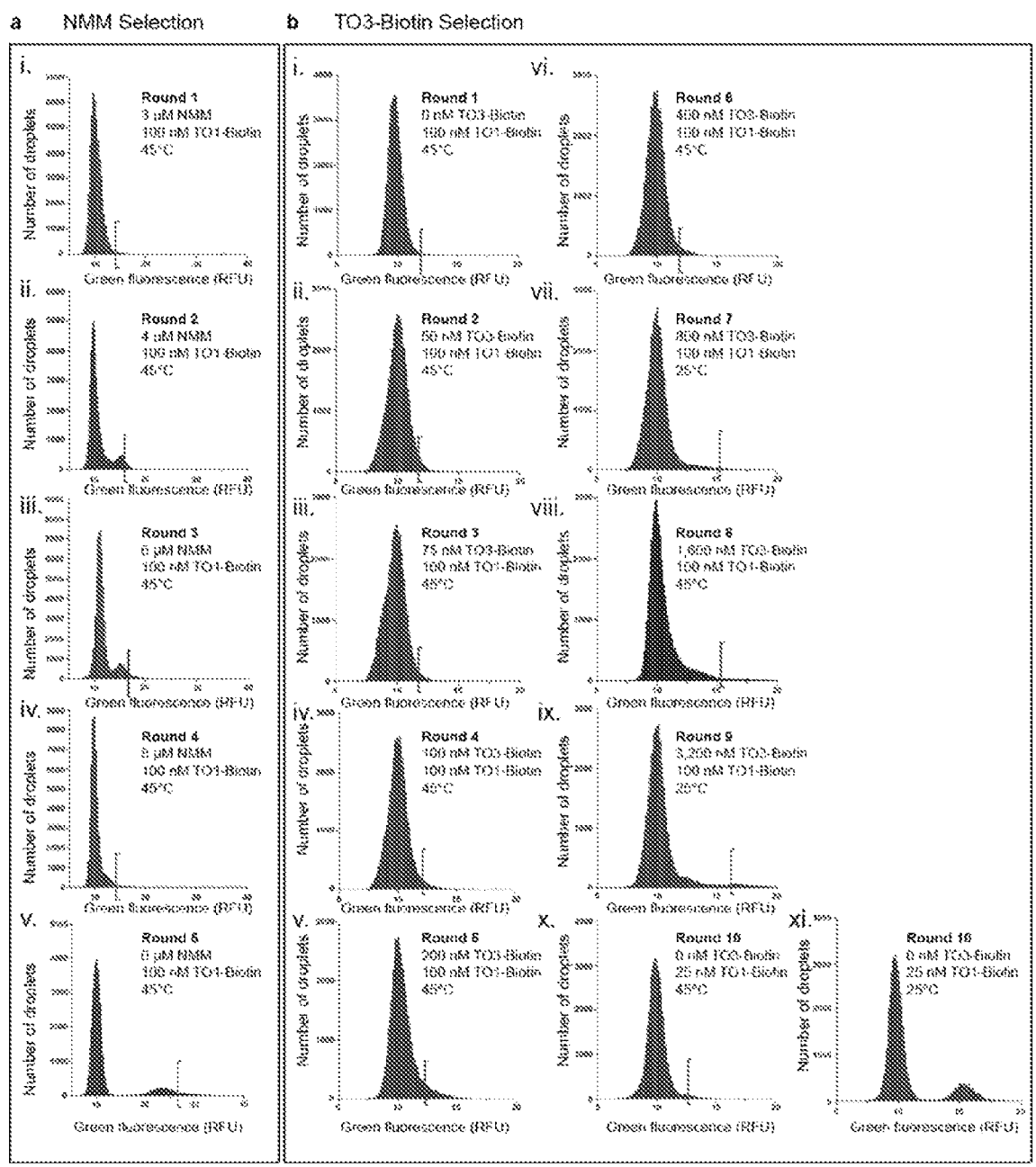
FIG. 5|Green fluorescence profile of the screenings performed in the presence of NMM and TO3-Biotin. (a) NMM. (b) TO3-Biotin. The green fluorescence of 50,000 droplets was used to build each profile. Red bars indicate the limit over which droplets were gated and sorted as positive. The selection conditions (TO1-Biotin and NMM/TO3-Biotin concentrations as well as the temperature of the analysis device) are indicated. In TO3-Biotin screening, b.xi corresponds to the same experiment as b.x but the fluorescence was recorded at 25° C.

A potential limitation of μIVC is the requirement of high TO1-Biotin concentrations (~100 nM), that would greatly exceed the Mango-I $K_D$ (~3 nM), and that could prevent the selection of high affinity aptamers. To mitigate this, we supplemented the in vitro transcription (IVT) mixture with TO1 competitors NMM (N-methyl mesoporphyrin IX) and TO3-Biotin, which are both known to interact with G-quadruplexes. The NMM supplemented IVT mixture significantly reduces TO1-Biotin/Mango-I fluorescence (FIG. 4). The NMM concentration was progressively increased during the first four screening rounds, therefore, any brightness increase at each round presumably resulted from the selection of brighter aptamers in the library which retaining high affinity and selectivity for TO1-Biotin (FIG. 1c). The RNA stability of the complex with TO1-Biotin was further challenged by sorting the droplets at 45° C. The relative fluorescence of the library increased 2.5-fold in the first round (~3 million variants analysed, Table 4), but it did not increase further over the later rounds (FIG. 1c, FIG. 5). However, the ability of NMM to compete against TO1-Biotin binding decreased progressively with each round (FIG. 6), indicating that the aptamers in the later rounds have higher affinity for TO1-Biotin.

TABLE 4

Metrics of screenings in presence of NMM

| Round | Temperature (° C.) | NMM (μM) | λ value | Fusion efficiency (%) | Number of analyzed droplets | Number of analyzed variants | Number of sorted droplets |
|---|---|---|---|---|---|---|---|
| 1 | 45 | 3 | 1.25 | 90 | 2,716,500 | 3,056,062 | 25,834 |
| 2 | 45 | 4 | 0.2 | 85 | 1,011,000 | 171,870 | 21,754 |
| 3 | 45 | 6 | 0.22 | 87 | 1,511,250 | 289,253 | 3,719 |

TABLE 4-continued

Metrics of screenings in presence of NMM

| Round | Temperature (° C.) | NMM (μM) | λ value | Fusion efficiency (%) | Number of analyzed droplets | Number of analyzed variants | Number of sorted droplets |
|---|---|---|---|---|---|---|---|
| 4 | 45 | 8 | 0.14 | 75 | 986,875 | 103,621 | 5,309 |
| 5 | 45 | 0 | 0.15 | 90 | 491,625 | 66,369 | 1,689 |

The last screening round shows that, in the absence of NMM, the fluorogenic properties of the enriched library remained unchanged (FIG. 1c). From the final enriched library, we cloned and sequenced 32 pool RNAs, and analysed their fluorogenic capacity (FIG. 7a, b). While the brightest clone was R5-NMM-20, six of the thirteen brightest aptamers exhibited an almost identical sequence to clone R5-NMM-5 (FIG. 7c).

In a second set of screenings, we increased the selection stringency by using the Mango-I specific competitor TO3-Biotin, which differs from TO1-Biotin by only two carbons in the methine bridge. To further increase the selection pressure for TO1-Biotin binding, we also decreased the RNA concentration in the droplets to 0.3 μM (from 8 μM with NMM). TO3-Biotin competitor was introduced in the second round of screening to ensure that positive droplets were not missed in the first round (FIG. 5b). In subsequent rounds, TO3-Biotin concentration was gradually increased (FIG. 1d and FIG. 6b and Table 4).

observed in the last rounds of selection. Accordingly, reverting the C66U mutation decreases the fluorescence of the aptamer/TO1-Biotin complex by ~44%. Finally, among the remaining clusters identified in the early rounds, cluster D, represented by R2-1, was found to have particularly high binding affinity.

Aptamer Structure and Function

Figure 2A:
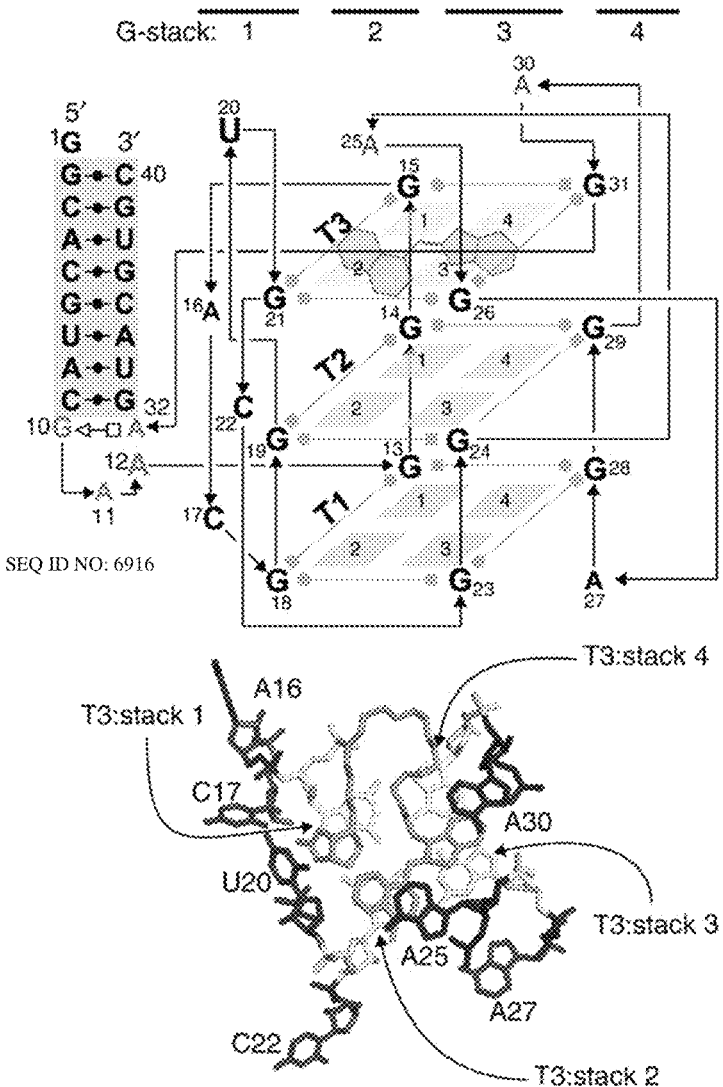
FIG. 2|RNA Mango I, II, III and IV core sequences and their properties. (a) Color coded alignment of RNA Mango I, II, III and IV. G residues in yellow are protected from DMS cleavage (data from panel d) when folded in the presence of fluorophore. Quadruplex stacks and their associated propeller sequences are numbered 1 through 4. The GAAA isolation motif of Mango I, together with two adenines essential for binding, are shown in green and red respectively. Purple shading represents a flanking stem region common for all four Mango aptamers. Schematic: A tertiary structure schematic of Mango I, showing tier 1, 2 and 3 of its quadruplex structure (T1, T2 and T3) and color-coded as in (a). TO1-Biotin is shown in green. Bottom: Top view of the Mango I core (PBD ID: 5V3F), showing the T3 tier of the quadruplex and relevant propeller residues, color coding matches the schematic and panel a. (b) Fluorescence binding curves for each Mango aptamer determined by titrating RNA aptamer concentration while holding TO1-Biotin fluorophore constant at 10 nM. $K_D$ values are shown next to each titration. (c) Same as for panel b but using 20 nM TO3-Biotin. Data for panels b and c have been normalized such that Mango I has a maximum fluorescence of 1. Error bars are standard deviation of three replicates. (d) DMS chemical protection patterns for the four Mango aptamers. 3' end-labelled RNA (terminal $^{32}$pCp shown as a black asterisk) was subjected to DMS chemical modification followed by reduction by $NaBH_4$ and aniline cleavage as described in the methods. RNA sequences are displayed to the right of each set of lanes with stem portions represented as purple blocks. Legend: T1—denatured T1 ladder; OH—partial alkaline hydrolysis ladder; (−) DMS—denatured reaction with dd$H_2$O added in place of DMS; 80° C. DMS—denatured DMS ladder; remaining lanes are native DMS reactions with addition of potassium to 140 mM final (+KCl), addition of sodium to 140 mM final (+NaCl), with or without 500 nM TO1-Biotin (+TO1-Biotin). Red asterisk indicates a notably unprotected G. Red daggers in Mango II and Mango IV indicate nucleotides that favor looping out of the core before returning with a G that participates in completing the first G stack (in contrast to Mango I that prefers three Gs in a row for a stack).
Figures 2B, 2C, 2D:
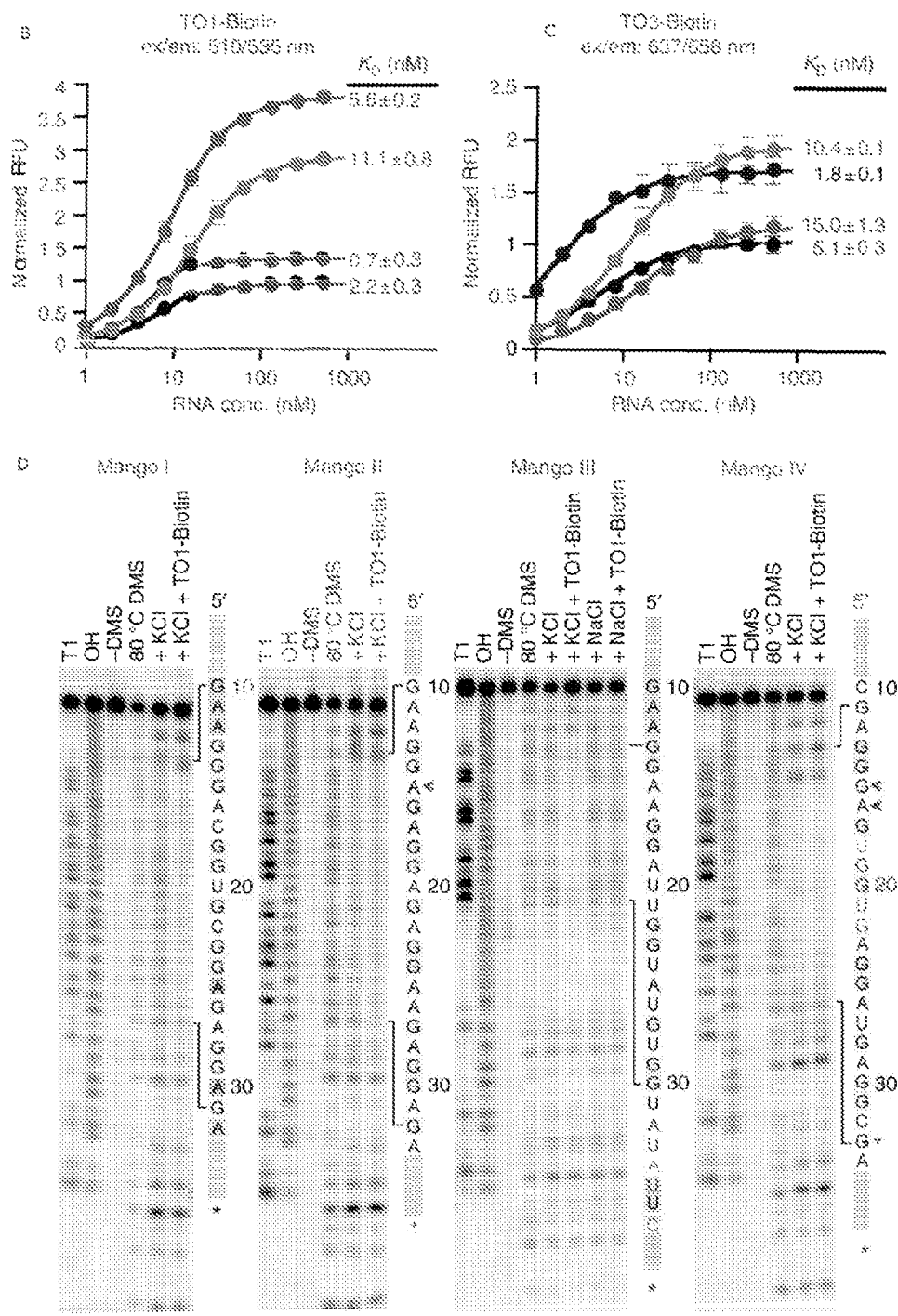
Figure 8:
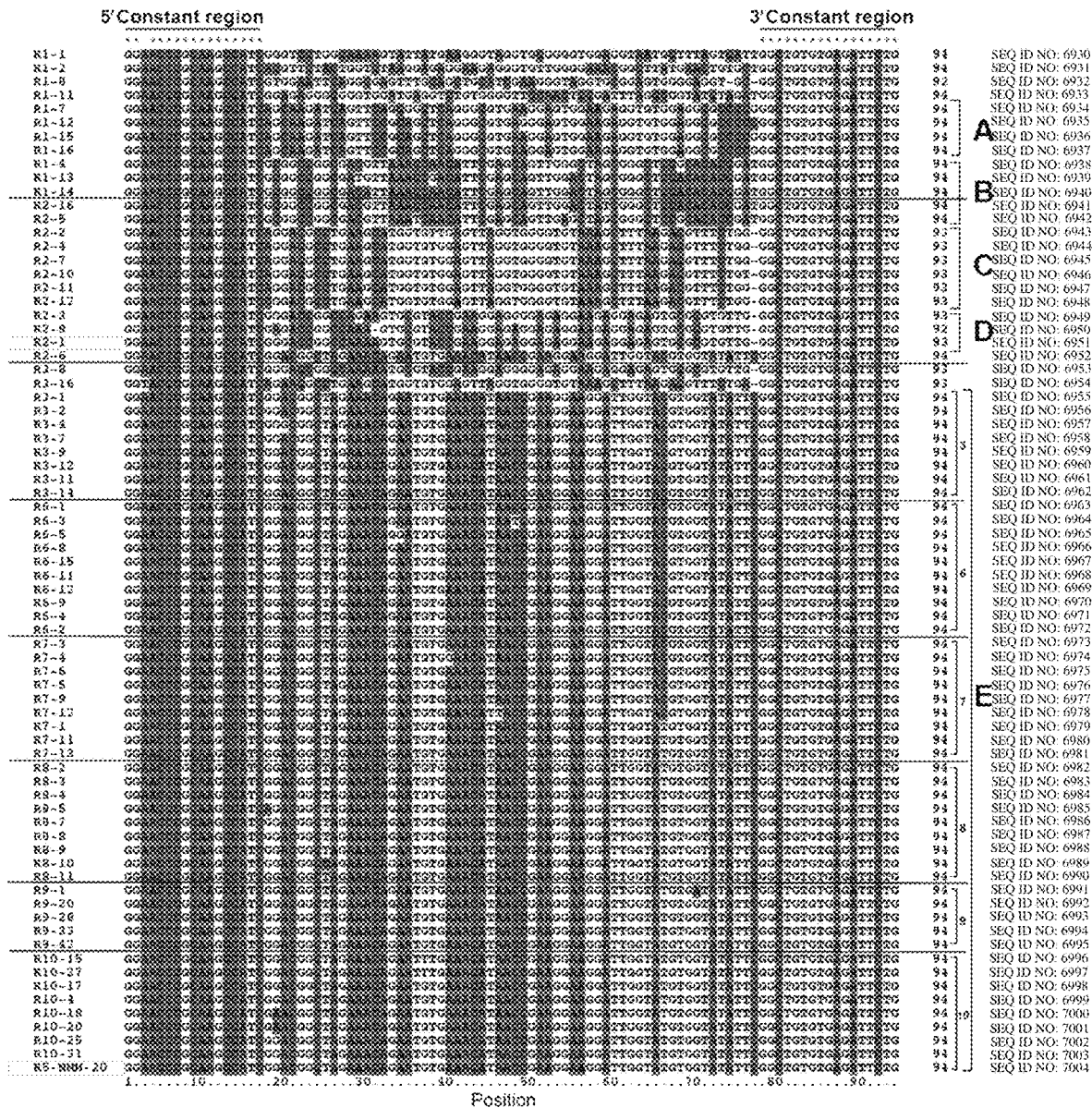
FIG. 8|Sequence analysis of the variants isolated across the rounds of screening performed in the presence of TO3-Biotin. The first green box indicates Mango II (R2-1). For comparison, the sequence of Mango III (R5-NMM-20) was also added and boxed in green. The families of sequences clustering together are labelled (A to E).

Based on the parental sequence isolates R2-1, R5-NMM-20 and R5-NMM-5 (FIGS. 6, 7 & 8), we engineered the minimal reference constructs Mango-II, Mango-III and Mango-IV (FIG. 2a), respectively, by truncation and sequence manipulation while maintaining the binding and fluorescent properties of the parental constructs (FIG. 9). Mango-II, III and IV were found to be 1.5-, 4- and 3-fold brighter than Mango-I, respectively (FIG. 2b). Mango-II binds TO1-Biotin with subnanomolar affinity, while Mango-III and IV had slightly weaker affinities than Mango-I (FIG. 2b). These constructs also demonstrated improved fluorescence response when bound to TO3-Biotin relative to

TABLE 5

Metrics of screenings in the presence of TO-3

| Round | Temperature (° C.) | T0-3 (nM) | T0-1 (nM) | λ value | Fusion efficiency (%) | Number of analyzed droplets | Number of analyzed variants | Number of sorted droplets |
|---|---|---|---|---|---|---|---|---|
| 1 | 45 | 0 | 100 | 1.25 | 95 | 2,328,630 | 2,765,248 | 4,607 |
| 2 | 45 | 50 | 100 | 0.2 | 80 | 1,106,750 | 177,080 | 8,328 |
| 3 | 45 | 75 | 100 | 0.15 | 94 | 1,019,990 | 143,818 | 6,446 |
| 4 | 45 | 100 | 100 | 0.2 | 95 | 1,002,500 | 190,475 | 11,478 |
| 5 | 45 | 200 | 100 | 0.17 | 90 | 1,044,500 | 159,808 | 12,205 |
| 6 | 45 | 400 | 100 | 0.25 | 85 | 1,015,880 | 215,874 | 8,779 |
| 7 | 25 | 800 | 100 | 0.2 | 79 | 1,087,500 | 195,750 | 8,463 |
| 8 | 45 | 1,600 | 100 | 0.26 | 88 | 768,250 | 175,775 | 4,729 |
| 9 | 25 | 3,200 | 100 | 0.28 | 75 | 547,250 | 114,922 | 5,868 |
| 10 | 45 | 0 | 25 | 0.15 | 70 | 499,500 | 52,447 | 4,004 |

In round 1, the relative fluorescence of the population increased, but it decreased upon addition of competitor (Round 2, FIG. 1d). In subsequent rounds, the relative fluorescence increased progressively until the TO3-Biotin concentration exceeded TO1-Biotin by 32-fold (3.2 μM and 100 nM, respectively). The final round shows that the enriched library maintains its florescent properties in the absence of competitor. RNA molecules from each of the final rounds were cloned and sequenced. Further characterization of the different libraries indicates that aptamers were first selected for their capacity to discriminate TO1-Biotin from TO3-Biotin (FIGS. 6b and c). Surprisingly, we found that, starting from round 3, the libraries were dominated by a single cluster of sequences (cluster E, FIG. 8) that was attributed to the TO3-resistant aptamers discussed above. In the last four rounds, this sequence was progressively replaced by the point mutant C66U; best represented by the aptamer R10-15. The progressive domination by R10-15 was likely at the origin of the fluorescence improvement Mango-I while exhibiting nanomolar binding affinities to this strongly red shifted fluorophore (FIG. 2c). Notably, the brightness of the Mango-III and Mango-IV TO1-Biotin bound complexes are 43,000 $M^{-1}cm^{-1}$ and 32,000 $M^{-1}cm^{-1}$, respectively, making Mango-III 1.3 times brighter than enhanced GFP (EGFP) a common benchmark for the characterization of improved fluorescent proteins.

Mango-II has a distinct flurophore binding mode from that of Mango-I. Crystallography shows that Mango-I consists of a three-tiered G-quadruplex core that binds TO1-Biotin by sandwiching it between the T3 layer of the G-quadruplex and A25 and A30 (FIG. 2a). This fluorophore binding core is isolated from an arbitrary RNA duplex (FIG. 2a, purple residues) by a novel GAAA tetraloop like adapter (FIG. 2a, blue residues). Like Mango-I, the Mango-II and IV aptamers function in the presence of a closing stem (FIGS. 2 & 9). DMS probing, which correctly confirmed the three-tiered quadruplex structure of Mango-I, indicated that Mango-II also contains a three-tiered quadruplex structure (FIG. 2d). In distinct contrast to Mango-I this aptamer appears to have looped out its A15 and has an adenine dinucleotide in its third propeller loop. This single A25 adenine found in these region of Mango-I is stacked on top of the methylquinone heterocycle of the TO1-Biotin implicating an important functional role in this sequence change in Mango-II. Indeed either of these changes either individually or together were shown to play an important role in the improved affinity and brightness of Mango-II (FIG. 9b).

Mango-IV, while superficially similar to both Mango-I and Mango-II based on primary sequence (FIG. 2a), surprisingly lacked N-7 protection at residue G15. This residue in Mango-I plays an important role in forming strand 1 of the T3 quadruplex tier and is fully DMS protected in Mango-I (FIG. 2a,d). Further, Mango-IV lacked DMS protection of residue G33, which in Mango-I plays an instrumental role in forming the T3 G-quartet and that is DMS protected in Mango-II. In addition the GAAA linker motif of Mango-I, that is apparently also present in Mango-II was not found in Mango-IV, with CGA being found before the first quadruplex tier of Mango-IV. Replacing the CGA of the Mango-IV sequence with GAA resulted in a four-fold decrease in binding affinity, suggesting a new role for this sequence element. This data supported by additional point mutational analysis (FIG. 9) indicates that the detailed folds of both Mango-II and Mango-IV are not only considerably different from each other but also Mango-I in the T3 region of the Mango-I fold (FIG. 2a).

The folding of the presently disclosed constructs was characterized further by examining their salt dependence, thermal melting properties, and CD spectra. Both Mango-II and IV have Hill coefficients and affinities for potassium similar to Mango-I (FIG. 10), and while Mango-I and Mango-II did not fluoresce appreciably in the presence of sodium ions, Mango-IV showed a limited fluorescence response. Most notably these aptamers in the presence of potassium were significantly resistant to high levels of $Mg^{2+}$ (256 mM) whereas Mango-I fluorescence was strongly inhibited at such concentrations indicating that Mango-II and Mango-IV were substantially more stably folded than Mango-I. Consistent with this, the DMS protection patterns of these aptamers (FIG. 2d) were largely invariant in the presence or absence of TO1-Biotin. In addition, Mango-II and Mango-IV have $A_{260}$ thermal melts that change little in the presence or absence of TO1-Biotin (FIG. 11). This is in distinct contrast to the thermal melt of Mango-I, which changes significantly upon presence or absence of TO1-Biotin. Consistent with the formation of a G-quadruplex structure in Mango-I, II, and IV the ligand bound CD spectra for each aptamer were quite similar (FIG. 12).

Figure 10:
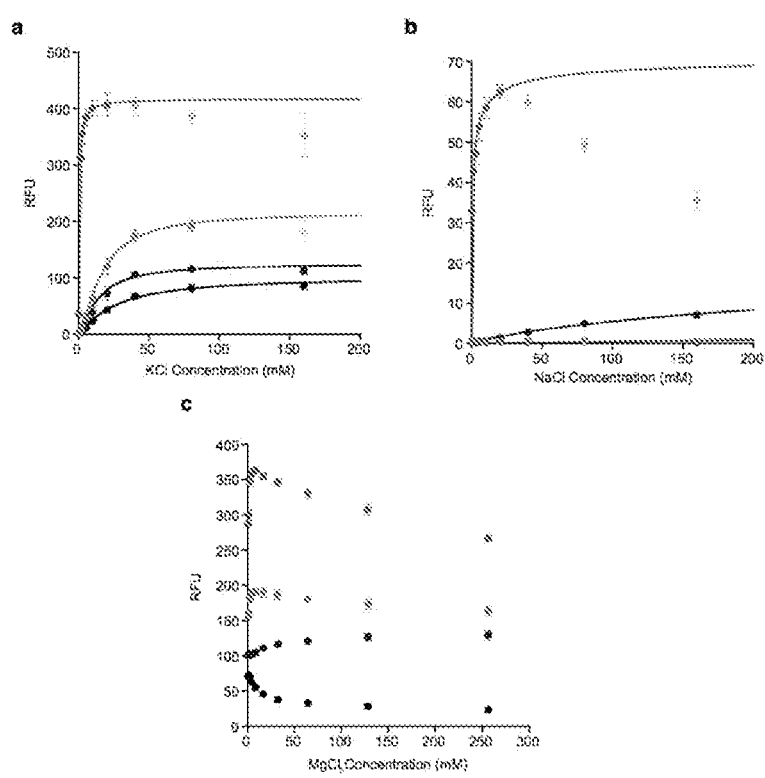
FIG. 10|Salt dependence of new Mango variants. Dependence of fluorescence of each Mango for (a) $K^+$, (b) $Na^+$ in place of $K^+$, and (c) $Mg^{2+}$ ions in a buffer containing 140 mM $K^+$. Each salt was titrated holding 25 nM RNA and 50 nM TO1-Biotin constant. 10 mM Tris buffer (pH 7.2) was used in place of phosphate of the WB buffer to avoid monovalent counter ions. Color-coding is as follows: Black—Mango I, Blue—Mango II, Green—Mango III, Orange—Mango IV. When possible, data is fitted to the Hill equation and Hill coefficients are listed in Table 1. Hill coefficients are fitted to dark points. Points in lighter shade have been excluded from the fit. Error bars are standard deviations of three replicates.

Mango-III, the brightest of the three exemplified aptamers was considerably different from the other three Mangos. Unable to form a three tiered G-quadruplex even in principle due to the presence of only nine guanines in its core, these guanines where, nevertheless found to be well protected from DMS (FIG. 2d) and a variety of evidence in addition to DMS probing indicates that they form a distinctly different two tiered quadruplex core in Mango-III. Mango-III contains much longer A/U rich propeller regions than any of the other Mangos exemplified herein (FIG. 2a) and has a fluorescence response to potassium and sodium that had a dramatically higher affinity (~two order of magnitude), while being only modestly inhibited by high levels of magnesium (FIG. 10). Its sigmodial fluorescent melting curve strongly resembles the melting of RNA Spinach and not the more linear melting curves observed for Mango-I, II and IV (FIG. 11). Similarly the CD spectra of the bound Mango-III complex is distinctly different in the 270-300 nm region from the other Mango constructs, indicative of a G-quadruplex structure distinct from that found in Mango-I (FIG. 12). Mango-III lacked an excitation shoulder found to be in common for all the other Mango constructs in the 270-300 nm region (FIG. 13), this and other differences in the excitation and emission spectra indicate that Mango-III has a motif significantly different from the other Mango aptamers exemplified herein.

Cellular Imaging of Mango Tagged RNAs

To demonstrate the efficacy of the exemplified aptamers in cellular imaging, we tagged the well characterized human 5S ribosomal RNA with each Mango variant by incorporating them into an F30 folding scaffold (FIG. 14a, Table 5) previously shown to improve cellular fluorescence. Each Mango tagged 5S RNA, with or without the folding scaffold or terminator hairpin, exhibited comparable fluorescence intensities in vitro (FIG. 14b). No appreciable fluorescence was observed with Mango mutants or in the absence of Mango RNA or TO1-Biotin fluorophore.

Figures 3A, 3B, 3C:
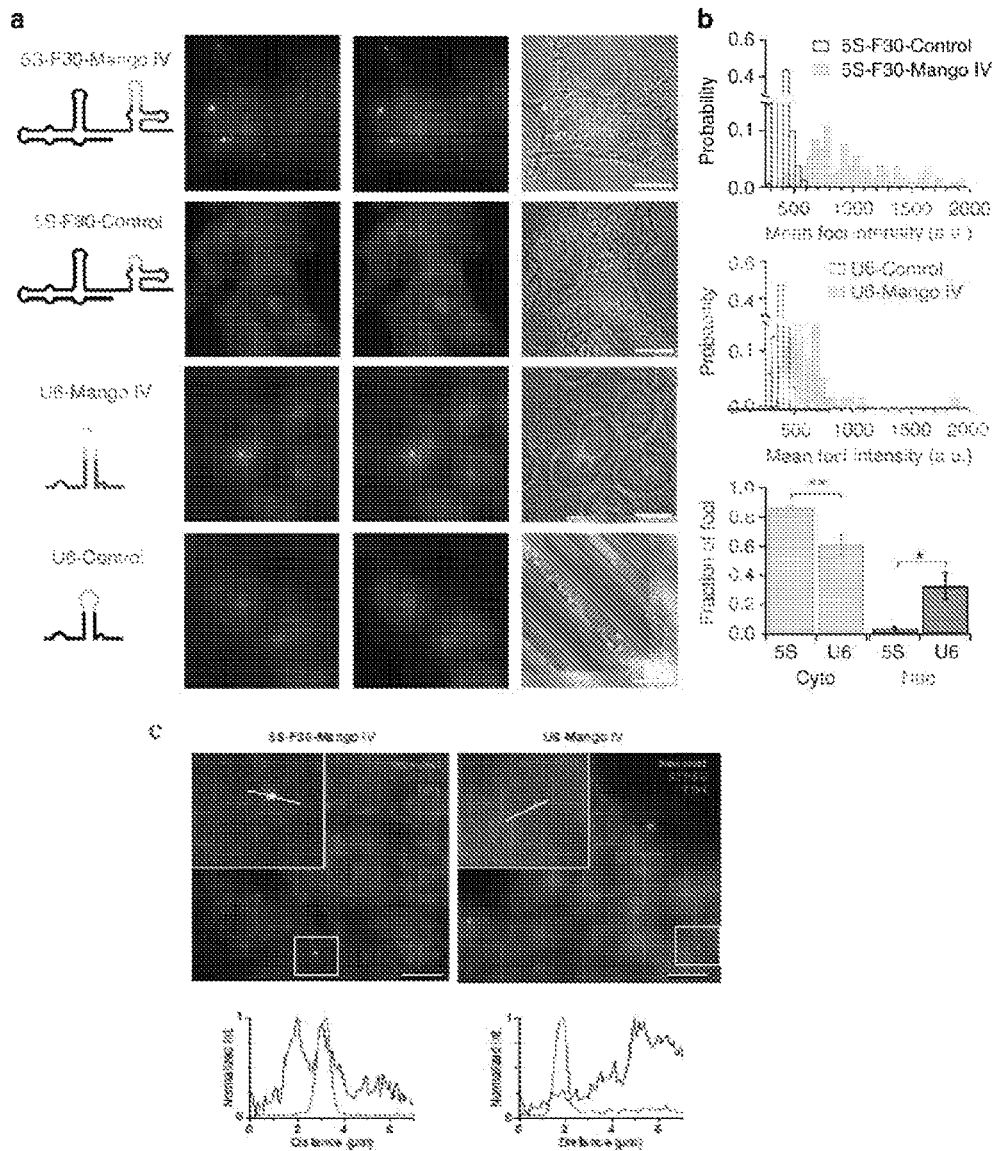
FIG. 3|Cellular imaging of Mango IV tagged RNAs. (a) Maximum projections of fixed cells containing Mango IV tagged 5S and U6 RNAs stained with 200 nM TO1-biotin (Yellow) and 1 mg/ml Hoechst 33258 (Blue). (b) Mean intensity distributions of 5S-Mango IV and U6-Mango IV Foci (Yellow) compared to controls (Black). Fraction of foci observed in the cytoplasm and nucleus for 5S and U6-Mango IV RNAs (bottom panel, * denotes p<0.05 and ** means p<0.01). (c) Cytoplasmic 5S-Mango IV foci localize with immunostained mitochondria (ATP5B), whereas cytoplasmic U6-Mango foci do not. Normalized fluorescence intensities as a function of distance along the inset white lines (bottom panels). (d) Localization of 5S-Mango IV and U6-Mango IV relative to immunostained Ribosomes (RP-S6), Mitochondria (ATP-5B) and snRNPs (LSm3). (e) Localization of 5S-Mango IV and U6-Mango IV foci relative to immunostained P-Bodies (GW182), Endosomes (EEA-1) and Stress Granules (TIA-1). Scale bars are 10 μM. All images are maximum projections except in c, which show a single focal plane.

To image the tagged RNA, we transfected in vitro transcribed 5S-F30-Mango RNAs into HEK293T cells, fixed the cells on ice with formaldehyde and stained with TO1-Biotin. This protocol being based on the surprising finding that in vitro, Mango-I, II and IV fluorophore-aptamer complexes were substantially resistant to formaldehyde at room temperature (FIG. 15). Up to ~10 bright RNA Mango foci could be readily detected per cell with a fluorescence microscope, but not in control transfections (FIG. 3a). A time course of this process (FIG. 16a) shows the initial delivery of lipofectamine particles to the cell membrane (5 min after transfection), followed by dispersal of the RNA in the cytoplasm (15-30 min) and foci formation (30-60 min). Contrary to 5S-F30-Mango-I, II and III, transfections with 5S-F30-Mango-IV RNA consistently exhibit visible foci (FIGS. 16 & 17), indicating that Mango-IV folds correctly both in the presence and absence of TO1-Biotin, unlike the others (FIG. 11). The mean intensity of the 5S-F30-Mango-IV foci is two to three-fold higher than the 5S-F30-Control background (FIG. 3b and FIG. 17). The majority of 5S-F30-Mango IV foci (~85%) are cytoplasmic, a small fraction (~5%) are clearly nuclear, and the remaining foci appeared on the nuclear boundary.

Figures 3D, 3E:
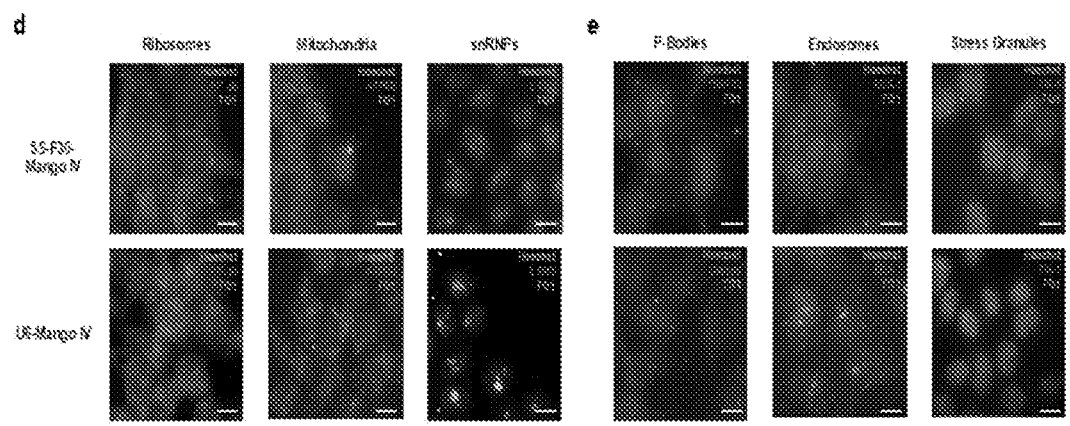

To illustrate the sub-cellular localization of the 5S-F30-Mango IV foci, we combined Mango imaging with immunostaining, which is made feasible by the ability of Mango-IV to withstand formaldehyde fixation. It has been shown that 5S rRNA is imported into mitochondria to facilitate the translation of mitochondrial proteins. Cytoplasmic 5S-Mango IV foci clearly overlap with immunostained mitochondria (FIG. 3c). Cytoplasmic 5S-Mango IV foci also overlap with antibody staining against the Ribosomal Protein S6 (RP-S6, FIG. 3d). Conversely, we do not observe overlap with other sub-cellular compartments, such as P-bodies, Endosomes or Stress Granules, where the transfected RNA could be processed for degradation (FIG. 3e).

To confirm that the observed foci are specific, we tagged and transfected an RNA that localizes to a different cellular compartment. The U6 snRNA (small nuclear RNA) is expected to associate with snRNP (Ribonuclear Protein) complexes in the nucleus. We tagged U6 snRNA by incorporating Mango-IV directly into an internal stem loop (FIG. 14). The resulting construct exhibits comparable fluorescence intensity to Mango IV alone in vitro (FIG. 14). Direct transfection of U6-Mango-IV snRNA yields fluorescent foci comparable to 5S-F30-Mango-IV (FIG. 3a), albeit with lower intensity (FIG. 3b). The fraction of nuclear foci increased ~9-fold, while cytoplasmic foci decrease significantly (p<0.01, FIG. 3b). As opposed to 5S-F30-Mango-IV, cytoplasmic U6-Mango-IV foci did not overlap with mitochondria (FIG. 3c) or ribosomes (FIG. 3d), whereas nuclear U6-Mango-IV foci overlap with snRNP protein Lsm3 (FIG. 3d), as expected. Similar to 5S-F30-Mango-IV, U6-Mango-IV foci do not overlap with other sub-cellular compartments, such as P-bodies, Endosomes or Stress Granules (FIG. 3e). Interestingly, we observe a diffuse signal above background in the nucleolus, which may correspond to freely diffusing U6-Mango IV molecules (FIG. 3a,d and FIG. 18).

Taken together, these fixed cell data show that Mango-IV, and other aptamers disclosed herein, can be used to label and image small cellular RNAs via direct transfection of in vitro transcribed RNAs, without affecting their expected sub-cellular localization. Finally, to illustrate that Mango-tagged RNA molecules can be imaged in live cells, we took advantage of the aptamer's high affinity for TO1-Biotin, and transfected in vitro transcribed 5S-F30-Mango-IV RNA pre-incubated with TO1-Biotin. After transfection the cells exhibit bright foci similar to those observed in FIG. 3a, with lower background fluorescence than observed in fixed cells (FIG. 16b). The foci can be readily tracked revealing three distinct diffusive behaviors: fast, slow and static (FIG. 16b). No such foci were observed in experiments with the 5S-F30-Control. Overall, these results demonstrate that fluorogenic Mango RNA aptamers are a versatile tool to image small cellular RNAs in fixed and live cells.

To estimate the number of fluorescent 5S-F30-Mango IV molecules in each foci, we performed photobleaching-assisted microscopy on fixed cells. A maximum likelihood estimate analysis of the photobleaching trajectories[27,28], revealed between 4 and 17 photobleaching steps per foci. In addition, the photobleaching step distribution reveals two peaks corresponding to either one or two molecules. The number of observed steps correlates linearly with the initial foci intensity below 2,000 intensity units. Altogether, these results indicate that each foci contains at least 4 to 17 fluorescent molecules, consistent with the observed range of experimental intensities, and raises the interesting possibility of imaging single molecules in live cells.

Finally, to test whether the new Mangos have the ability to function as genetically encoded tags expressed in cells, we constructed plasmids that express the 5S rRNA under the control of a RNA pol III promoter in conjunction with a mCherry reporter gene to identify successfully transfected cells (FIG. 43a). Upon fixation, we observed that cells expressing the pSLQ-5S-F30-Mango II and IV constructs exhibit an increased fluorescent signal in nucleolar compartments as well as forming distinct cytoplasmic foci when compared with the pSLQ-5S-F30-Control construct (FIG. 43a). The analysis of the peak Mango and mCherry intensities for multiple cells expressing the pSLQ-5S-F30-Mango II plasmid shows a population of cells with a high Mango specific signal, not seen in cells expressing the pSLQ-5S-F30-Control plasmid (FIG. 5b). Interestingly, we observe that cells exhibiting lower mCherry intensities can also show higher Mango signal, consistent with RNA transcription preceding mCherry translation. In agreement with this, reducing plasmid expression time, from 24 to 12 h, increased the number of observed cytoplasmic foci. Under the same conditions of fixation and staining, signal was not observed in untransfected cells or in cells expressing the 5S-F30-Broccoli construct. The robust cytoplasmic signal observed after 12 h of pSLQ-5S-Mango IV expression enabled us to combine Mango imaging with immunofluorescence (FIG. 43c). As expected, the observed Mango foci co-localize significantly with Ribosomal Protein L7. However, no significant co-localization was observed with the mitochondrial stain ATP5B. The absence of co-mitochondrial localization, in this case, is likely due to the fact that most nucleolar expressed 5S rRNA will assemble into ribosomes in the nucleus, whereas 5S rRNA molecules transfected directly in the cytoplasm will not, and are more readily available for mitochondrial import. The observed cytoplasmic foci did not co-localize with immunostaining for stress granules, P-bodies or endosomes.

To confirm that the observed 5S rRNA foci are specific, we expressed a Mango II tagged small Cajal-body specific RNA (mgU2-47) that mediates the 2'-O-methylation of the U2 snRNA[29]. Upon expression, the Mango tagged mgU2-47 RNA formed well defined nuclear foci that were absent in the mgU2-47 Control RNA (FIGS. 43a and b). The nuclear foci also co-localized with immunostained Cajal-bodies (FIG. 43c). Taken together these results demonstrate the ability of Mango tags to function as efficient genetically encoded reporters of RNA sub-cellular location.

The photobleaching properties of Mango I and Mango IV were superior to RNA Spinach with bleaching half-lives 10 times longer on average under identical illumination conditions (FIG. 16 d&e).

Bipartite Aptamer Systems

In the X-Ray crystal structure of Mango I, the 'GAA^A' tetraloop motif, with 'GAA' on the 5' end of the G quadruplex core (represented by ^) and the remaining 'A' on the 3' end of the core, separates two phosphates juxtaposed at the end of the core by 8 Å. We recognized that this 8 Å separation is important for fluorescence enhancement with select embodiments of RNA Mangos, with the G quadruplex in configuration for ligand binding. We have recreated this conformation in what are designated herein as bipartite embodiments, involving the complementary base pairing of portions of the Mango aptamers to an RNA target. In embodiments of this kind, the Mango aptamer acts as a switch, with fluorescence being switched on by binding to the target, which may accordingly be called a 'trigger'. This is schematically illustrated in FIG. 20.

FIG. 20 shows various Mango I switches and triggers initially tested, illustrating that in these select embodiments Mango switches with two A residues in the GAA' A' tetraloop motif, an A being on the either side of the G-quadruplex core, gave maximal response to the binding of the trigger RNA. We also illustrate that those triggers which are continuously complementary to the bait regions, without any intervening gap of unpaired bases, to be optimal for fluorescence.

To illustrate a functional bipartite system, we used β-actin mRNA from mouse embryo fibroblasts as a model. β-actin mRNA, because of its Zipcode region binds to Zipcode Binding Protein (ZBP) which then binds to cytoskeleton proteins for transport to the leading edges of lamellipodia in growing fibroblasts (FIG. 22A). We developed RNA Mango constructs that target β-actin mRNA in a target region which has previously been shown not to interfere with the localization. We developed another RNA Mango construct that targets the Zipcode binding region, which when targeted causes delocalization of β-actin m RNA.

To quantitatively compare bipartite constructs, we measured the difference in RFU between bound and unbound Mangos, providing a contrast ratio of bound to unbound fluorescence, reflecting the increase in fluorescence upon binding of the bipartite construct to the target in the presence of the fluorophore. Higher contrast reflects lower background, and thus higher signal to noise ratio. For instance, in the Mango I based bipartite construct targeting β-actin mRNA in the target region 1087-1121, the equilibrium RFU after the addition of TO1-Biotin to the Mango construct is 3 (point a in FIG. 22B), after adding the target it increased to 321 (point b in FIG. 22B), a contrast of ~110. In the same manner the contrast for the Mango construct targeting the zipcode region (2955-2990) of β-actin, is ~80.

The Mango II core sequence was used to prepare alternative bipartite constructs that include an inhibitory stem, a sequence that is part of the aptamer that binds to a portion of the core sequence, thereby inhibiting core formation in the absence of binding to a target. Surprising, as illustrated in FIG. 23, we found that the addition of an inhibitory stem not only decreased fluorescence in the absence of the trigger, but also resulted in increased total fluorescence upon the addition of the trigger.

The length of the inhibitory stem may be adjusted in alternative embodiments. If the stem length is too short, it may not adequately destabilize the G-quadruplex, thus decreasing the contrast. If the stem length is too long, then the inhibited structure, with the stem bound to the core, may become so stable that it inhibits or delays folding of G-quadruplex upon trigger binding. In exemplary embodiments, we illustrate optimization of inhibitory stem length in Mango II constructs. Increasing the inhibitory arm length by increments of one nucleotide revealed that an inhibitory arm containing five nucleotides gave high contrast with minimal decrease in the rate of fluorescence increase (FIG. 24). A Mango bipartite construct, as illustrated in FIG. 25, has three parts:

1) RNA mango core (i)—comprised of aptamer sequence that binds to TO1-B and becomes fluorescent;
2) An inhibitory arm (ii)—comprised of regions complementary to the RNA Mango so that it binds and destabilizes RNA Mango core in the absence of a 'trigger' RNA, decreasing fluorescence in the absence of the RNA of interest;
3) Bait (iiia, iiib and iiic)—comprised of one or more regions, which are complementary to the RNA of interest, sequence depending upon RNA of interest.

An alternative bipartite embodiment was prepared based on a Mango IV core sequence. A variety of constructs were tested (FIG. 26), with a range of results (FIG. 27) found.

A variety of bipartite Mango constructs were exemplified in vivo via transfection into MCF7 cells. In these embodiments, the sequences shown in FIG. 28 were used to probe for beta actin mRNA, with the exception of MII.O4, which acted as a non-hybridizing control. TO1-Biotin was introduced into the media, exemplifying the fact that it is cell permeable. FIG. 29 and FIG. 30 illustrate the time course of fluorescence for these bipartite Mango switch probes.

Unimolecular Mango III Rolling Circle Amplification

Early transcription assays revealed that the mango constructs are capable of displaying fluorescence enhancement in T7 transcription buffer supplemented with potassium to a final of 140 mM (FIG. 31). This illustrates that in select embodiments Mango aptamers may be used for detection of nucleic acids in a two-step fluorescence-based detection system using the Mango aptamers as the reporter. For example, using a conventional rolling circle amplification method as a first step, transcription in step two produces multiple copies of the Mango aptamer, which in turn bind TO1-biotin and progressively enhances fluorescence. Nucleic acid concentration can be discerned by a simple fluorescence reading. In these assays, the Mango III fluorescence emerged rapidly upon the addition of the RNA polymerase (FIG. 32). Sensitivity down to 5 nM was easily demonstrated without optimization and operating all enzymes isothermally at room temperature (FIGS. 33 & 34).

Fluorophores

A variety of flurophores may be used in alternative aspects of the presently disclosed compositions and processes. For example, U.S. Pat. No. 4,883,867 describes fluorometric assays for ribonucleic acids that use dyes having Formula I:

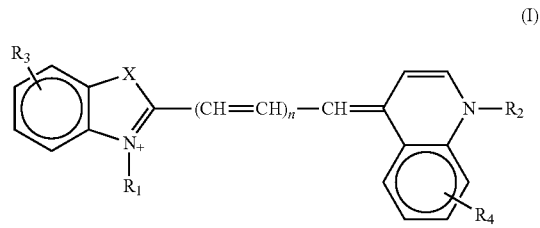

Wherein:
X=O, S, Se, or $C(CH_3)_n$,
=alkyl having from 1-6 carbons;
$R_2$=alkyl having from 1-6 carbons;
$R_3$=fused benzene, alkyl having 1-6 carbons, methoxy or H;
$R_4$=alkyl having 1-6 carbons, methoxy or H; and
n=zero or an integer from 1-6.

Alternative embodiments disclosed therein include compounds wherein:
$R_1$=$CH_3$, $R_2$=$CH_3$, $R_3$=H, $R_4$=H, X=S, and n=1; or,
$R_1$=$CH_3$, $R_2$=$CH_3$, $R_3$=fused benzene, $R_4$=H, X=S, and n=0; or,
$R_1$=$CH_3$, $R_2$=$CH_3$, $R_3$=H, $R_4$=H, X=O, and n=0; or,
X=O, S, Se or $C(CH_3)_2$, $R_1$=alkyl having from 1-6 carbons, $R_2$=alkyl having from 1-6 carbons, $R_3$=fused benzene, alkyl having 1-6 carbons, methoxy or is hydrogen, $R_4$=alkyl having 1-6 carbons, methoxy or H; and n=0 or an integer from 1-6; or,
$R_1$=$CH_3$, $R_2$=$CH_3$, $R_3$=H, $R_4$=H, X=S, and n=1; or,
$R_1$=$CH_3$, $R_2$=$CH_3$, $R_3$=fused benzene, $R_4$=H, X=S, and n=0; or,
$R_1$=$CH_3$, $R_2$=$CH_3$, $R_3$=H, $R_4$=H, X=O, and n=0.

In U.S. Pat. No. 4,883,867, Thiazole Orange (TO1) is identified as the compound of Formula I where $R_1$=$R_2$=$CH_3$; $R_3$=$R_4$=H, X=S and n=0. As such, TO1 is an asymmetric cyanine fluorophore, which contains a benzothiazole ring covalently linked to a quinoline ring via a monomethine bridge. In aqueous solution the fluorophore exhibits very low fluorescence ($\lambda_{ex}$=500 nm, $\lambda_{em}$=525 nm, $\phi$=2×10$^{-4}$) due to rapid nonradiative decay through the torsional motion in the monomethine bridge joining the two heterocycles. Normally, TO1 becomes strongly fluorescent when the monomethine bridge connecting the two heterocycles is rigidified through nonspecific insertion into double-stranded helical nucleic acids giving a fluorescence quantum yield of 0.11. TO1 is characterized by: small size, lack of toxicity, plasma and nuclear membrane permeability, short intracellular half-life, and the accessibility of a broad wavelength range via simply synthesized TO1 analogues.

In the examples disclosed herein, it has been shown that a very wide variety of substituents may be present at $R_1$ in compounds of Formula I, for example comprising one or a combination of, substituted or unsubstituted: alkenyl, halogen (e.g., fluorine, chlorine, bromine, iodine, etc.), hydroxyl, alkoxy (e.g., methoxy, ethoxy, perchloromethoxy, perfluoromethoxy, etc.), alkylcarbonyloxy, alkyloxycarbonyl, arylcarbonyloxy, arylcarbonylamino, alkoxycarbonylamino, al koxycarbonyloxy, aryloxycarbonyloxy, carboxylate, alkylcarbonyl, alkylaminoacarbonyl, arylalkyl aminocarbonyl, alkenylaminocarbonyl, alkylcarbonyl, arylcarbonyl, aminoalkyl, arylalkylcarbonyl, alkenylcarbonyl, alkoxycarbonyl, silyl, aminocarbonyl, alkylthiocarbonyl, phosphate, aralkyl, phosphonato, phosphinato, cyano, amino, acylamino, amido, imino, sulfhydryl, alkylthio, sulfate, arylthio, thiocarboxylate, alkylsulfinyl, sulfonato, sulfamoyl, sulfonamido, nitro, cyano, azido, heterocyclyl, alkylaryl, aryl and heteroaryl substituents. The $R_1$ group of Formula I may accordingly be substituted with any substituent which allows the fluorophore compound to perform its intended function.

In alternative embodiments, fluorophores for use as disclosed herein may include compounds of Formula II:

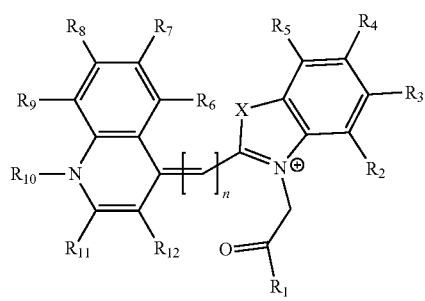

(II)

Wherein:

In selected embodiments, $R_1$ of compounds of Formula I or Formula II may be functionalized. For example, TO1-Acetate may be used as the basis for attaching a biotin tag for in vitro selection and subsequent complex purification. Embodiments have for example been tested and shown to work having biotinylated $R_1$ substituents, with PEG linkers, for TO1 (n=1) and TO3 (n=3), including biotin (with variable length PEG linkers), desthiobiotin (with variable length PEG linkers), and CY5$^{tm}$, wherein $R_1$ is, respectively:

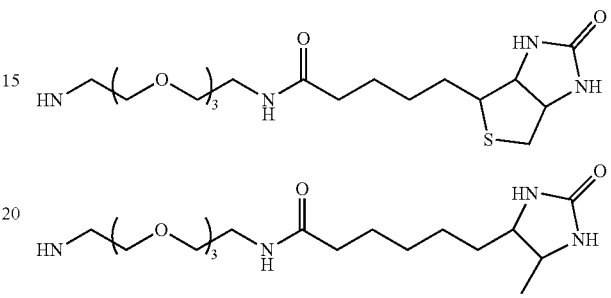

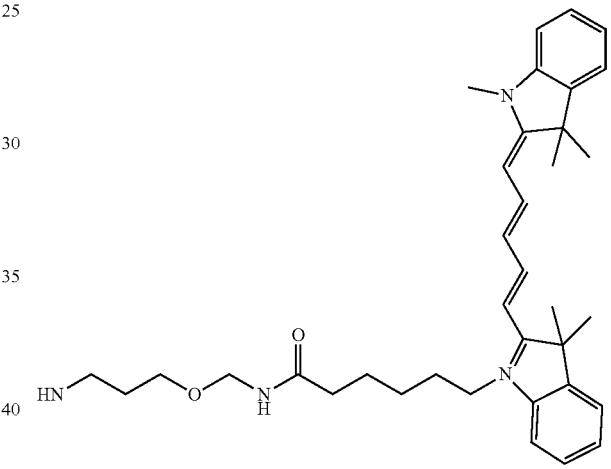

Advantageously, the following other specific compounds are encompassed by the invention:

| R Groups | |
|---|---|
| $R_1$ | Any substituent which allows the fluorophore compound to perform its intended function, eg: biotin, fluorescent dyes, NEB SNAP tags, with or without an amide bond in the linker. |
| $R_2$ through $R_5$ | H, F, Cl, Br, I, $CH_3$, linear polymers, extended heterocycles (i.e. built of adjacent pairs of groups). |
| $R_6$-$R_9$ | H, F, Cl, Br, I, $CH_3$, linear polymers, extended heterocycles (i.e. built of adjacent pairs of groups). |
| $R_{10}$ | H, F, Cl, Br, I, $CH_3$, linear polymers, extended heterocycles. |
| $R_{11}$ through $R_{12}$ | H, F, Cl, Br, I, $CH_3$, linear polymers, extended heterocycles (i.e. built of adjacent pairs of groups). |
| X atoms | O (YO3), S (TO1 & TO3), Se. |
| n (bridging groups) | 1 (TO1) or 3 (TO3), or 5. |

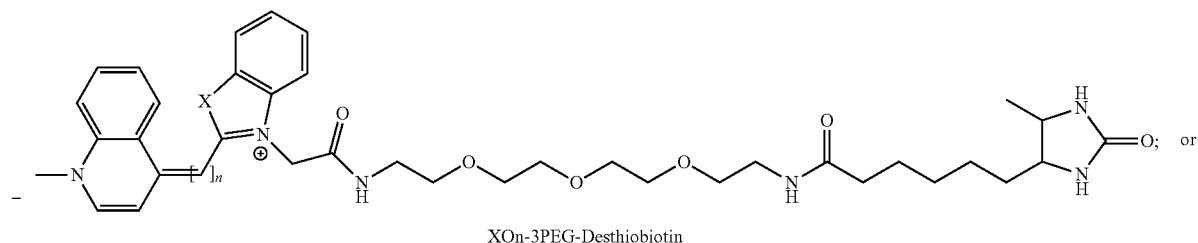
XOn-3PEG-Desthiobiotin
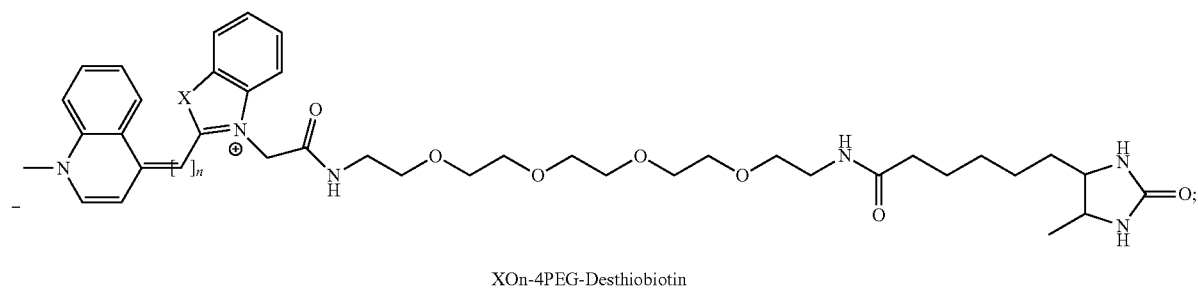
XOn-4PEG-Desthiobiotin
and in particular
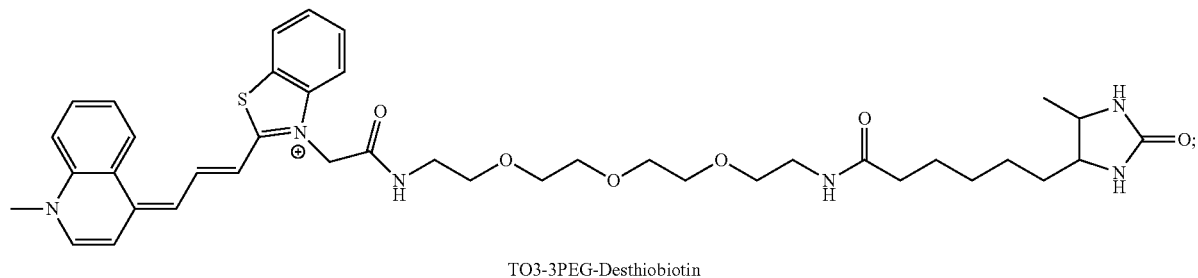
TO3-3PEG-Desthiobiotin
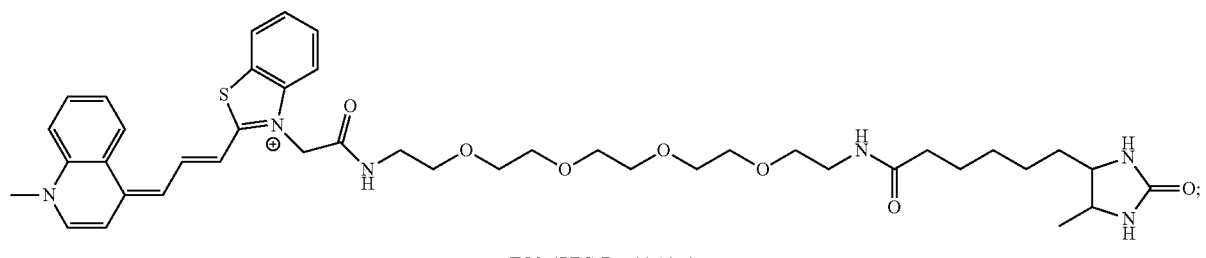
TO3-4PEG-Desthiobiotin
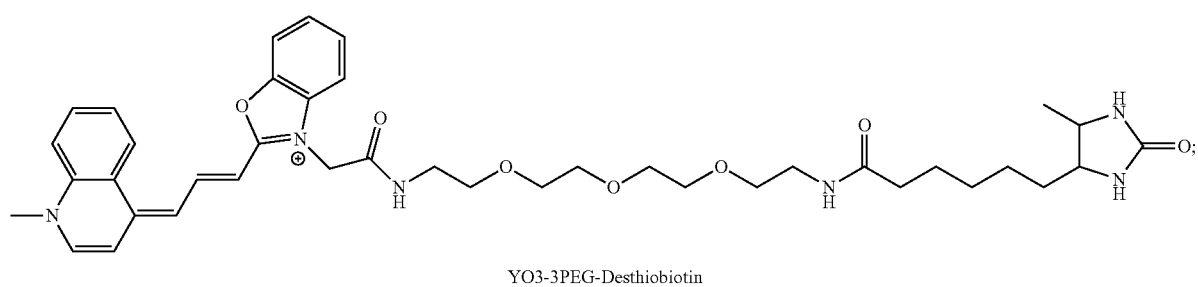
YO3-3PEG-Desthiobiotin -continued
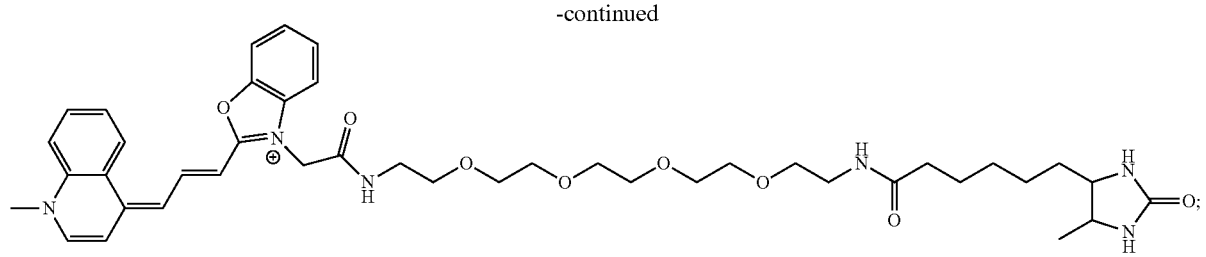
YO3-4PEG-Desthiobiotin
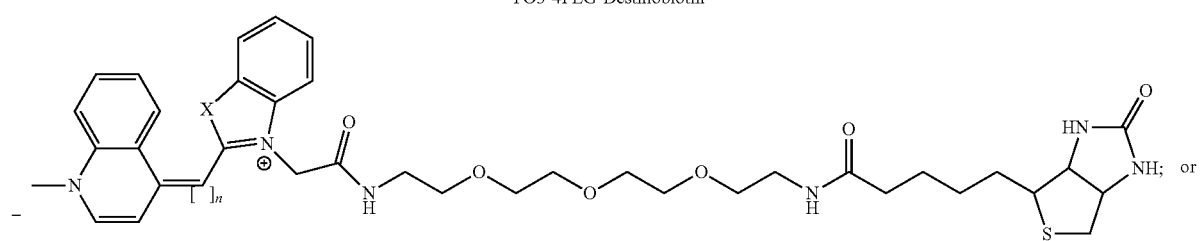
XOn-3PEG-Biotin
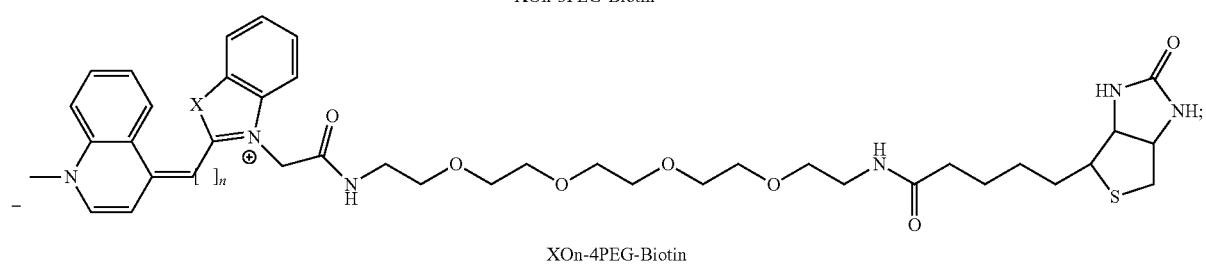
XOn-4PEG-Biotin
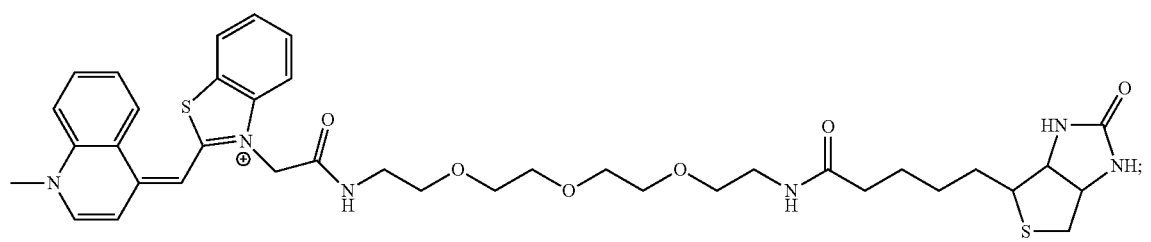
TO1-3PEG-Biotin
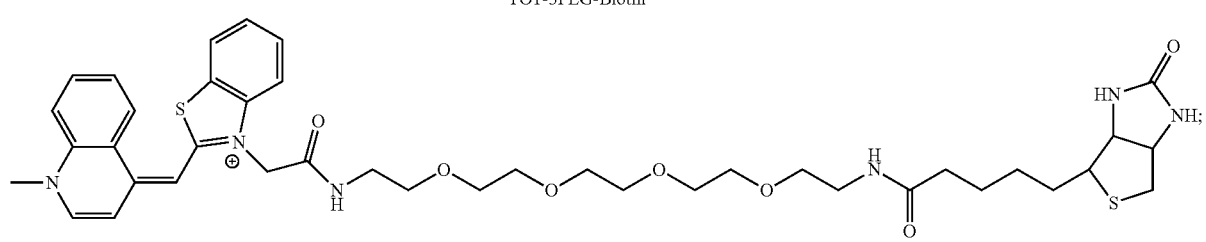
TO1-4PEG-Biotin
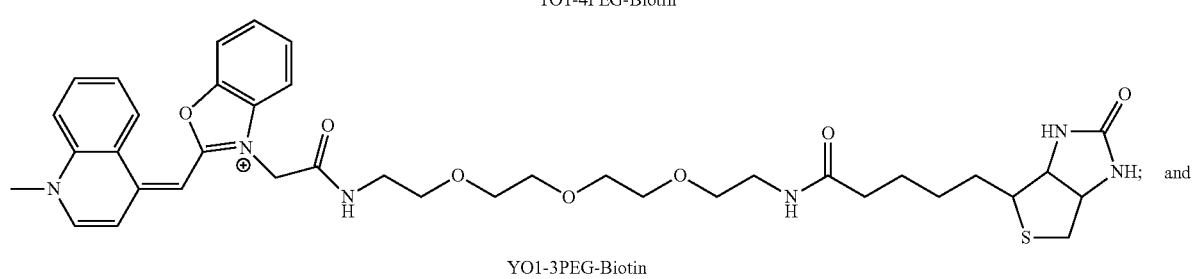
YO1-3PEG-Biotin

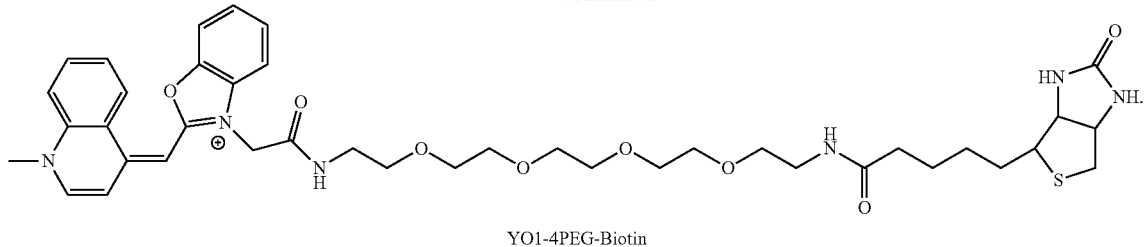

YO1-4PEG-Biotin

Unless explicitly stated otherwise, the terms "alkyl" and "heteroalkyl" each includes any reasonable combination of the following: (1) saturated alkyls as well as unsaturated alkyls (e.g. alkenyls and alkynyls); (2) linear or branched; (3) acyclic, cyclic (aromatic or nonaromatic) or multi-cyclic (fused rings, multiple non-fused rings or a combination thereof); and (4) unsubstituted or substituted. For example, an alkyl or heteroalkyl (i.e. "alkyl/heteroalkyl") may be saturated, branched and cyclic, or unsaturated, branched and cyclic, or linear and unsaturated, or any other reasonable combination according to the skill of the person of skill in the art. Where the size of the alkyl/heteroalkyl is specified as $X_1$-$X_z$, where z is any integer larger than 1 (e.g. 15, 18, 30, 100 or the like), it will be understood that the alkyl/heteroalkyl comprises at least 3 carbons and heteroatoms so as to form a ring. If unspecified, the size of the alkyl/heteroalkyl is what would be considered reasonable to the person of skill in the art. For example, but without limitation, if unspecified, the size of an alkyl may be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 89, 90, 91, 92, 93, 94, 95, 96, 97, 98, 99, 100 or more than 100 carbons in length, subject to the common general knowledge of the person of skill in the art. Further, but without limitation, if unspecified, the size of a heteroalkyl may be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 89, 90, 91, 92, 93, 94, 95, 96, 97, 98, 99, 100 or more than 100 carbons and heteroatoms in length, subject to the common general knowledge of the person of skill in the art.

For convenience, unless otherwise specified the term "alkyl" shall without limitation include "alkylenyl" unless the context of its use clearly excludes alkylenyls, and vice versa. For example, but without limitation, where $R^1$, $R^2$ and $R^3$ in $R^1$-$R^2$—$R^3$ are identified as alkyl groups, it will be understood that $R^2$ is an alkylenyl group and, similarly, $R^1$ and $R^3$ do not include alkylenyl groups.

As used herein, in the context of an alkyl/heteroalkyl group of a compound, the term "linear" may be used as it is normally understood to a person of skill in the art and generally refers to a chemical entity that comprises a skeleton or main chain that does not split off into more than one contiguous chain. Non-limiting examples of linear alkyls include methyl, ethyl, n-propyl, and n-butyl.

As used herein, the term "branched" may be used as it is normally understood to a person of skill in the art and generally refers to a chemical entity that comprises a skeleton or main chain that splits off into more than one contiguous chain. The portions of the skeleton or main chain that split off in more than one direction may be linear, cyclic or any combination thereof. Non-limiting examples of a branched alkyl group include tert-butyl and isopropyl.

As used herein, the term "saturated" when referring to a chemical entity may be used as it is normally understood to a person of skill in the art and generally refers to a chemical entity that comprises only single bonds. Non-limiting examples of a saturated $C_1$-$C_{15}$ alkyl group may include methyl, ethyl, n-propyl, i-propyl, sec-propyl, n-butyl, i-butyl, sec-butyl, t-butyl, n-pentyl, i-pentyl, sec-pentyl, t-pentyl, n-hexyl, i-hexyl, 1,2-dimethylpropyl, 2-ethylpropyl, 1-methyl-2-ethylpropyl, l-ethyl-2-methylpropyl, 1,1,2-trimethylpropyl, 1,1,2-triethylpropyl, 1,1-dimethylbutyl, 2,2-dimethylbutyl, 2-ethylbutyl, 1,3-dimethylbutyl, 2-methylpentyl, 3-methylpentyl, sec-hexyl, t-hexyl, n-heptyl, i-heptyl, sec-heptyl, t-heptyl, n-octyl, i-octyl, sec-octyl, t-octyl, n-nonyl, i-nonyl, sec-nonyl, t-nonyl, n-decyl, i-decyl, sec-decyl and t-decyl. Non-limiting examples of $C_2$-$C_{15}$ alkenyl group may include vinyl, allyl, isopropenyl, l-propene-2-yl, 1-butene-l-yl, 1-butene-2-yl, l-butene-3-yl, 2-butene-l-yl, 2-butene-2-yl, octenyl and decenyl. Non-limiting examples of $C_2$-$C_{15}$ alkynyl group may include ethynyl, propynyl, butynyl, pentynyl, hexynyl, heptynyl, octynyl, nonynyl and decynyl. Without limitation, the above-defined saturated $C_1$-$C_{15}$ alkyls, $C_2$-$C_{15}$ alkenyls and $C_2$-$C_{15}$ alkynyls are all encompassed within the term "$X_1$-$X_{15}$ alkyl", as used herein. Without limitation, the term "$X_1$-$X_{15}$ heteroalkyl" would encompass each of the above-defined saturated $C_1$-$C_{15}$ alkyls, $C_2$-$C_{15}$ alkenyls and $C_2$-$C_{15}$ alkynyls, where one or more of the carbon atoms is independently replaced with a heteroatom. The person of skill in the art would understand that various combinations of different heteroatoms may be used.

Unless explicitly stated otherwise, the terms "aryl" and "heteroaryl" each includes any reasonable combination of the following: (1) cyclic or multi-cyclic (fused rings, multiple non-fused rings or a combination thereof); and (2) aromatic (i.e. unsaturated rings) or nonaromatic (i.e. saturated rings); and (3) unsubstituted or substituted. Non-limiting examples of aryls or heteroaryls (i.e. "aryl/heteroaryl") include: phenyl, naphthyl, thienyl, indolyl, pyridyl and the like. If unspecified, the size of the aryl/heteroaryl is what would be considered reasonable to the person of skill in the art. For example, but without limitation, if unspecified, the size of an aryl may be 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 89, 90, 91, 92, 93, 94, 95, 96, 97, 98, 99, 100 or more than 100 carbons in length, subject to the common general knowledge of the person of skill in the art. Further, but without limitation, if unspecified, the size of a heteroaryl may be 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 89, 90, 91, 92, 93, 94, 95, 96, 97, 98, 99, 100 or more than 100 carbons and heteroatoms in length, subject to the common general knowledge of the person of skill in the art. It is noted that an aryl or heteroaryl may have all or only a portion of its skeleton or main chain bonded in such a way so as to form a 'loop', circle or ring of atoms bonded together. That is, the aryl/heteroaryl may comprise linear or branched chains of carbons/heteroatoms that are not part of a ring or loop.

As used herein, the term "substituted" is used as it would normally be understood to a person of skill in the art and generally refers to a compound or chemical entity that has one chemical group replaced with a different chemical group. Unless otherwise specified, a substituted alkyl may be an alkyl in which one or more hydrogen atom(s) may be/are replaced with one or more atom(s) that may be/are not hydrogen(s). For example, chloromethyl is a non-limiting example of a substituted alkyl, more particularly an example of a substituted methyl. Aminoethyl is another non-limiting example of a substituted alkyl, more particularly an example of a substituted ethyl. Unless otherwise specified, a substituted compound or group (e.g. alkyl, heteroalkyl, aryl, heteroaryl and the like) may be substituted with any chemical group reasonable to the person of skill in the art. For example, but without limitation, a hydrogen bonded to a carbon or heteroatom (e.g. N) may be substituted with halide (e.g. F, I, Br, Cl), amide, oxo, hydroxyl, thiol, phosphate, phosphonate, sulfate, $SO_2H$, $SO_3H$, alkyls, heteroalkyls, aryl, heteroaryl, ketones, carboxaldehyde, carboxylates, carboxamides, nitriles, monohalomethyl, dihalomethyl, trihalomethyl.

As used herein, the term "unsubstituted" is used as it would normally be understood to a person of skill in the art. Non-limiting examples of unsubstituted alkyls include methyl, ethyl, tert-butyl, and pentyl. The expression "optionally substituted" is used interchangeably with the expression "unsubstituted or substituted".

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range, and inclusive of all numbers and fractions subsumed within the respective ranges. The word "comprising" is used herein as an open-ended term, substantially equivalent to the phrase "including, but not limited to", and the word "comprises" has a corresponding meaning. Terms such as "consisting essentially of" and "consists essentially of" allow for elements not explicitly recited, but exclude elements that are found in the prior art or that affect a basic or novel characteristic of the invention. As used herein, the singular forms "a", "an" and "the" include plural referents unless the context clearly dictates otherwise. Thus, for example, reference to "a thing" includes more than one such thing. Citation of references herein is not an admission that such references are prior art to the present invention. Any priority document(s) and all publications, including but not limited to patents and patent applications, cited in this specification are incorporated herein by reference as if each individual publication were specifically and individually indicated to be incorporated by reference herein and as though fully set forth herein. The invention includes all embodiments and variations substantially as hereinbefore described and with reference to the examples and drawings. Nothing herein is intended as a promise of any specific utility for all embodiments.

The term "about" or "approximately" as used herein when referring to a measurable value such as a parameter, an amount, a temporal duration, and the like, is meant to encompass variations of +/−20% or less, preferably +/−10% or less, more preferably +/−5% or less, and still more preferably +/−1% or less of and from the specified value, insofar such variations are appropriate to perform in the disclosed invention. It is to be understood that the value to which the modifier "about" or "approximately" refers is itself also specifically, and preferably, disclosed.

All references cited in the present specification are hereby incorporated by reference in their entirety. In particular, the teachings of all references herein specifically referred to are incorporated by reference, along with all documents cited in documents that are cited herein.

Standard reference works setting forth the general principles of recombinant DNA technology include Molecular Cloning: A Laboratory Manual, 2nd ed., vol. 1-3, ed. Sambrook et al., Cold Spring Harbor Laboratory Press, Cold Spring Harbor, N.Y., 1989; Current Protocols in Molecular Biology, ed. Ausubel et al., Greene Publishing and Wiley-Interscience, New York, 1992 (with periodic updates) ("Ausubel et al. 1992"); the series Methods in Enzymology (Academic Press, Inc.); Innis et al., PCR Protocols: A Guide to Methods and Applications, Academic Press: San Diego, 1990; PCR 2: A Practical Approach (M. J. MacPherson, B. D. Hames and G. R. Taylor eds. (1995); Harlow and Lane, eds. (1988) Antibodies, a Laboratory Manual; and Animal Cell Culture (R. I. Freshney, ed. (1987). General principles of microbiology are set forth, for example, in Davis, B. D. et al., Microbiology, 3rd edition, Harper & Row, publishers, Philadelphia, Pa. (1980).

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the appended claims, any of the claimed embodiments can be used in any combination.

In this description of the invention, reference is made to the accompanying drawings that form a part hereof, and in which are shown by way of illustration only of specific embodiments in which the invention may be practiced. It is to be understood that other embodiments may be utilized and structural or logical changes may be made without departing from the scope of the present invention. The description, therefore, is not to be taken in a limiting sense, and the scope of the present invention is defined by the appended claims.

It is an object of the invention to not encompass within the invention any previously known product, process of making the product, or method of using the product such that Applicants reserve the right and hereby disclose a disclaimer of any previously known product, process, or method. It is further noted that the invention does not encompass any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product.

Preferred statements (features) and embodiments may be combined with any other features or embodiments unless clearly indicated to the contrary. In particular, any feature indicated as being preferred or advantageous may be combined with any other feature or features or statements indicated as being preferred or advantageous.

PROTOCOL EXAMPLES

High Throughput Screening

Digital droplet PCR: DNA libraries were diluted in 200 µg/mL yeast total RNA solution (Ambion) down to ~8 template DNA molecules per picoliter to have $\lambda=0.2$, or ~40 templates DNA molecules per picoliter. 1 µL of this dilution was then introduced in 100 µL of a PCR mixture containing 0.2 µM of Forward primer (5'-CTT AAT TAC GAC TCA CTA TAG GAA CCC GCA AGC CAT C (SEQ ID NO: 6900), 0.2 µM of Reverse primer (5'-CAG AAT CTC ACA CAG CC(SEQ ID NO: 6901)), 0.2 mM of each dNTP, 0.67 mg/mL Dextran-Texas Red 70 kDa (Molecular Probes), 0.1% Pluronic F68, Phire II DNA polymerase (Thermo-Scientific) and the corresponding buffer according to recommended concentrations. The mixture was loaded in a length of PTFE tubing and infused into a droplet generator microfluidic device where it was dispersed into 2.5 pL droplets (production rate of ~12,000 droplets/second) carried by HFE 7500 fluorinated oil (3M) supplemented with 3% of a fluorosurfactant. Droplet production frequency was monitored and used to determine droplet volume by adjusting pumps flow rates (MFCS, Fluigent). Emulsions were collected in 0.2 µL tubes, and subjected to an initial denaturation step of 2 min at 95° C. followed by 30 PCR cycles of: 30 sec at 95° C., 30 sec at 55° C., 1 min 30 at 72° C.

Droplet fusion: PCR droplets were then injected into a fusion device at a rate of ~1,500 droplets/second, spaced by a stream of HFE 7500 fluorinated oil supplemented with 2% fluorosurfactant. Each PCR droplet was synchronized with a 16 µL in vitro transcription (IVT) droplet containing 2.2 mM of each NTP (Larova), 24 mM $MgCl_2$, 44 mM Tris-HCl pH 8.0, 50 mM KCl, 5 mM DTT, 1 mM Spermidine, 35 µg/mL of Dextran-Texas Red 70 kDa (Molecular Probes), 0.1% Pluronic F68, 20 µg/mL T7 RNA polymerase (purified in the laboratory), 100 nM TO1-Biotin (Dolgosheina et al., 2014), 1 µg inorganic pyrophosphatase (Roche) supplemented with the desired concentration of NMM. For the screenings performed in the presence of TO3-Biotin (Dolgosheina et al., 2014), the T7 RNA polymerase (New England Biolabs) concentration was reduced to 70 U per reaction. The IVT mixture was loaded in a length of PTFE tubing that was kept on ice during all the experiment. IVT droplets were produced using a stream of HFE 7500 fluorinated oil supplemented with 2% (w/w) of fluorinated surfactant. Flow-rates (MFCS, Fluigent) were adjusted to generate 16 pL IVT droplets and maximize the synchronization of one PCR droplet with one IVT droplet. Pairs of droplets were then fused with an AC field (350 V at 30 kHz) and the resulting emulsion collected off-chip and incubated for 120 min (high concentration of T7 RNA polymerase, NMM screenings) or 30 min (low concentration of T7 RNA polymerase, TO3-Biotin screenings) at 37° C. Droplet analysis and sorting: The emulsion was finally re-injected into an analysis and sorting microfluidic device mounted on a Thermo plate (Tokai Hit) holding the temperature at 45° C. as previously described[3]. Droplets were re-injected at a frequency of ~200 droplets/second, spaced with a stream of surfactant-free HFE 7500 fluorinated oil. The green fluorescence (TO1-Biotin in complex with the aptamer) of each droplet was analysed and the droplets having the highest green fluorescence were sorted. The gated droplets were deflected into collecting channel by applying a 1 ms AC field (1200 V, 30 kHz) and collected into a 1.5 mL tube. Collected droplets were recovered by flushing 200 µL of HFE 7500 fluorinated oil (3M) through the tubing. 100 µL of 1H, 1H, 2H, 2H-perfluoro-1-octanol (Sigma-Aldrich) and 200 µL of 200 µg/mL yeast total RNA solution (Ambion) were then added, the droplets were broken by vortexing the mixture and DNA-containing aqueous phase was recovered.

Quantification of RNA Produced in Droplets

A PCR mixture supplemented with DNA coding for RNA Mango ($\lambda=10$, ensuring that all the droplets were occupied) was emulsified in 2.5 pL droplets and the DNA amplified as above. The droplets were paired and fused with droplets of in vitro transcription mixture containing either a low (70 U of enzyme from New England Biolabs) or a high (20 µg/mL of enzyme purified in the lab) concentration of T7 RNA polymerase and the resulting emulsions were incubated for respectively 30 min or 120 min at 37° C. After incubation, the RNA-containing phase was recovered using 1H, 1H, 2H, 2H-perfluoro-1-octanol (Sigma-Aldrich) and the transcription was stopped by a phenol extraction followed by an ethanol precipitation in the presence of 300 mM sodium acetate pH 5.5 (Sigma-Aldrich). After centrifugation and a wash in 70% ethanol, the pellets were re-suspended in water. 10 U of Baseline-Zero™ DNase (Epicentre) and the corresponding buffer were added and a second incubation of 60 min at 37° C. was performed. The DNase was removed by phenol extraction and RNA recovered by ethanol precipitation.

Recovered RNAs, were reverse transcribed for 60 min at 55° C., followed by 5 min at 95° C., in a mixture containing 10 pmol of Reverse primer, 0.5 mM of each dNTPs RT Maxima (Thermo-Scientific) and the corresponding buffer according to recommended concentrations. The cDNA was amplified using SsoFast™ Evagreen supermix (Bio-Rad) supplemented with 0.2 µM of each primer (Forward and Reverse) using a CFX96 Touch™ Real TimePCR Detection System (Bio-Rad). Finally the cDNA was quantified using the calibration curve obtained with reactions performed with purified RNAs.

Enrichment Measurement

The pool molecules contained in 2 µL recovered from the sorted fractions were introduced into 100 µL of PCR mixture containing 0.1 µM of each primer (Fwd and Rev), 0.2 mM of each dNTP, 0.05 U/µL of DreamTaq™ and its corresponding buffer (Fermentas). The mixture was then subjected to an initial denaturation step of 30 sec at 95° C., followed by 20 cycles of: 5 sec at 95° C. and 30 sec at 60° C. 20 µL of PCR products were then in vitro transcribed in 250 µL of mixture containing 2 mM of each NTP, 25 mM MgCl$_2$, 40 mM Tris-HCl pH 8.0, 5 mM DTT, 1 mM Spermidine and 70 µg/mL T7 RNA polymerase. After 4 hours of incubation at 37° C., 10 U of Baseline-Zero™ DNase (Epicentre) and the corresponding buffer were added and the mixture was incubated for 60 min at 37° C. RNAs were recovered by phenol extraction followed by an ethanol precipitation in the presence of 300 mM sodium acetate pH 5.5 (Sigma-Aldrich). After centrifugation and a wash in 70% ethanol, the pellets were dissolved in denaturing loading buffer (0.05% bromophenol blue, 0.05% xylene cyanol, 20% glycerol, 1× TBE, 8 M urea) and the solution loaded onto a 12% denaturing 8 M urea acrylamide/bisacrylamide gel. The piece of gel containing RNA was identified by UV shadowing, sliced from the gel and transferred into a dialyze tube (MWCO=3 500, Spectrum Lab) filled with TBE. RNA was electro-eluted by placing the montage in TBE for 60 min at 100 V. Eluted RNA were filtered in centrifuge tube (porosity 0.45 µm, VWR) and ethanol precipitated in the presence of 300 mM sodium acetate pH 5.5. After centrifugation and a wash in 70% ethanol, the pellets were dissolved in DEPC-Treated water and quantified with Nanodrop (Thermo Scientific).

In the case of NMM screenings, 2 µM of RNA were incubated with 100 nM of TO1-Biotin in 40 mM Tris-HCl pH 8.0, 50 mM KCl, and 22 mM MgCl$_2$. Eventually, NMM (3 µM) was added and TO1-Biotin fluorescence (ex. 492 nm/em. 516 nm) measured. In the case of TO3-Biotin screenings, 300 nM of RNA and 100 nM of TO1-Biotin were used with or without 1.6 µM of TO3-Biotin. Both green (ex. 492 nm/em. 516 nm) and red (ex. 635 nm/em. 665 nm) fluorescence were measured.

TA-Cloning, Sequencing and Colony Screening

Genes contained in the libraries were diluted in a PCR mixture as a immediately above and thermocycled 25 times using a final extension step of 10 min at 72° C. PCR products were inserted in pTZ57R/T vector following manufacturer's instruction (InsTAclone PCR cloning Kit, Thermo-Scientific). Ligation products were recovered by phenol/chloroform extraction and ~100 ng of DNA used to transform Electro-10 blue bacteria (Agilent) placed in a 2 mm electroporation (MicroPulser, Bio-Rad). After an hour of recovery at 37° C. under agitation, bacteria were plated on Luria broth (LB)-Ampicillin agar plate and incubated overnight at 37° C. The colonies were picked, used to inoculate liquid LB and grown at 37° C. until saturation. Plasmids DNA were extracted using "GeneJet Plasmid Miniprep kit" (Thermo-Scientific), and sequences determined by Sanger approach (GATC Biotech).

Single colonies were introduced in 10 µL of a PCR mixture identical to that used for TA-cloning and the DNA amplified as above. 2 µL of PCR product added to 18 µL of in vitro transcription mixture containing 2 mM of each NTP, 25 mM MgCl$_2$, 40 mM Tris-HCl pH 8.0, 50 mM KCl, 5 mM DTT, 1 mM Spermidine, 70 µg/mL T7 RNA polymerase and 100 nM TO1-Biotin. The mix was then split in two and one aliquot was supplemented with 3 µM of NMM. The reaction was incubated in a real-time thermocycler (Mx 3005P, Agilent) for 2 hours at 37° C. and the green fluorescence (ex. 492 nm/em. 516 nm) measured every minute.

DMS Probing of Mangos

DMS (Denaturing): Protocol is adapted from Lorsch and Szostak, 1994[13]. 50 nM RNA was 3' end labelled with $^{32}$pCp and gel purified. The resulting RNA was incubated in 50 mM HEPES pH 7.5 (volume 50 µL) at room temperature for 30 min. After incubation, 10 µg carrier RNA was added. The sample was then heated to 90° C. for 3 min before the addition of 0.5 µL of 25% DMS (diluted in ethanol) and heated to 80° C. for 1 min. 150 µL ice cold ethanol+5 µL 3 M NaCl was then immediately added and moved to −20° C. for 30 min. DMS modified RNA was pelleted by centrifuge at 16,300 RCF at 4° C. for 20 min.

DMS (Native): 50 nM 3' end labeled RNA was incubated in 50 mM HEPES pH 7.5, 1 mM MgCl$_2$, 140 mM either KCl or NaCl, with or without 500 nM TO1-Biotin (final volume 50 µL) at room temperature for 30 min. After incubation, 10 µg carrier RNA was added. The sample was then incubated at room temperature for 15 min after the addition of 0.5 µL of 100% DMS. 150 µL ice cold ethanol+5 µL 3 M NaCl was then immediately added and pelleted as for the denaturing DMS protocol.

Reduction: Pellets were resuspended in 10 µL 1 M Tris buffer pH 8 and 10 µL of freshly prepared 0.2 M sodium borohydride was added. Reaction was carried out on ice and in the dark for 30 min. Reactions were stopped by ethanol precipitation as above.

Aniline Cleavage: To the resulting pellet, 20 µL (1 part Aniline, 7 parts ddH$_2$O, 3 parts glacial acetic acid) were added and incubated at 60° C. for 15 min in the dark. Samples were flash frozen by placing tubes in liquid nitrogen and lyophilized by speed vacuum centrifuge. Once dry, 20 µL ddH$_2$O was added, the sample refrozen and lyophilized once again. The pellet was resuspended in a 50% formamide denaturing solution before being loading on a 15% polyacrylamide gel (19:1 acrylamide:bis).

T1 RNase Ladder and Alkaline Hydrolysis Ladder: 200 pmol 3' end labeled RNA was incubated in 20 mM sodium citrate, 6.3 M urea, and 1 U/µL T1 RNase (Thermo Scientific) at 50° C. for 10 min. Samples was flash frozen in liquid nitrogen for 5 min, heat denatured in denaturing solution at 95° C. for 5 min prior to gel loading. Hydrolysis ladders were generated by incubating in 50 mM NaHCO$_3$ at 90° C. for 20 min and neutralizing using 0.17 M Tris-HCl.

Screening for Minimal Functional Mango Motifs

To identify the minimal functional motif of each Mango, truncated constructs were designed as shown in FIG. 9. DNA constructs (IDT) were transcribed by run-off transcription using T7 RNA polymerase. RNA was gel purified on 10% polyacrylamide gels. RNA concentrations were determined by NanoDrop readings at A$_{260}$, where extinction coefficients were estimated based on average 11,000 M$^{-1}$cm$^{-1}$ per base.

Affinity Measurements of Mango Variants

Fluorescence data was gathered using a Varian Cary Eclipse Spectrophotometer unless otherwise stated. Fluorescent titrations in the in vivo mimicking buffer (WB: 140 mM KCl, 1 mM MgCl$_2$, 10 mM NaH$_2$PO$_4$ pH 7.2, 0.05% Tween-20) were performed to determine binding affinities. Fluorescence was measured at the maximum excitation and emission wavelengths of each complex (FIG. 13). Curves were fitted using least squares (Kaleidagraph 4.5) using the following equation for TO1-Biotin:

$$F([RNA])=F_{max}[(K_D+[RNA]+[Fluorophore])/2-\sqrt{(([RNA]-[Fluorophore])2+K_D(K_D+2[RNA]+2[Fluorophore]))]/2}+F_{unbound} \quad (Eq. 1)$$

Where F([RNA]) is the fluorescence as a function of RNA concentration [RNA], $F_{max}$ is the maximal fluorescence of the bound complex and $F_{unbound}$ the fluorescence of the unbound fluorophore. When the fluorescence of $F_{unbound}$ was undetectable, it was set to zero.

Or to the following equation for TO3-Biotin and NMM experiments:

$$F([RNA])=F_{max}[RNA]/(K_D+[RNA])+F_{unbound} \quad (Eq. 2)$$

$F_{max}$ was determined using Eq. 1 or Eq. 2 as appropriate.

Temperature Dependent Fluorescence and UV Melting Curves

Temperature dependence measurements were started at 90° C. decreasing at a rate of 1° C./min until 20° C., then returned at 1° C./min until 90° C. was reached. Fluorescence measurements were obtained at the maximum excitation/emission of the fluorescent complex used and were measured in WB buffer using 1 µM RNA either with or without 5 µM TO1-Biotin. Temperature dependence of fluorescence and absorbance were measured using a Varian Cary Eclipse Fluorescence Spectrophotometer at excitation and emission peaks and a Varian Cary 100 Bio UV-visible spectrophotometer monitoring at 260 nm.

Circular Dichroism

Circular dichroism spectra were obtained on an Applied Photophysics Chirascan Circular Dichroism Spectrometer using 5 µM RNA, 140 mM monovalent salts and 7 µM TO1-Biotin. Spectra were scanned in 1 nm steps with a bandwidth of 1 nm. Data shown is the average of three repeats. Samples were measured using a 1 mm pathlength quartz cuvette (Starna Cells Inc.).

Formaldehyde Resistance Assay

RNA Mango aptamers were incubated with TO1-Biotin in WB buffer for at least one hour until equilibrium fluorescence was reached. Formaldehyde was then added such that final concentrations after dilution were 50 nM RNA, 100 nM TO1-Biotin and 0, 2, 4, or 8% formaldehyde. Fluorescence was measured as a kinetic run at a rate of 2 readings per minute using a Varian Cary Eclipse Fluorescence Spectrophotometer, ex/em=510±2.5/535±5 nm.

Cell Culture and Maintenance

HEK293T cells were grown in Dulbecco Modified Eagle's Medium containing 10% Fetal Bovine Serum, 2 mM D-Glucose, 2 mM L-Glutamine, 1 mM Sodium Pyruvate and 100 U/ml Penicillin/Streptomycin (Thermo Fisher) and maintained at 37° C. with 5% $CO_2$ in a humidified incubator. Cells used for imaging were cultured in Ibidi glass bottomed 8-well chamber slides (Ibidi GmbH).

5S-Mango RNA Synthesis and Purification

DNA encoding the F30 folding scaffold was modified to incorporate the Mango RNA sequences and ordered from (Intergrated DNA Technologies). The DNA was amplified by PCR to incorporate 5' SalI and 3' XbaI restriction sites. PCR products were digested using Fast Digest enzymes (Thermo Fisher) and ligated into SalI/XbaI linearized and Shrimp Alkaline Phosphotase (NEB) treated pAV5S-F30-2xdBroccoli (Addgene plasmid 66845, a gift from Dr S. Jaffrey). DNA encoding the full 5S-F30-Mango sequence was PCR amplified and a 5' T7 RNA polymerase promoter introduced. DNA was transcribed in vitro with T7 RNA polymerase (NEB) at 37° C. for 16 h in 40 mM Tris-HCl, 30 mM $MgCl_2$, 2 mM spermidine, 1 mM dithiothreitol, 5 mM rNTPs, 1 U/µl E. coli inorganic pyrophosphatase, 4 U/µl T7 RNA polymerase (pH 7.9). RNA was purified from an 8 M urea denaturing polyacrylamide and bis to acrylamide ratios here XX gel followed by elution in RNA elution buffer (40 mM Tris-HCl pH 8.0, 0.5 M sodium acetate, 0.1 mM EDTA) and ethanol precipitation. Fluorescence measurements were taken for each of the RNA constructs using a Varian Cary Eclipse Fluorescence Spectrophotometer (Agilent) containing 40 nM TO1-Biotin, 200 nM RNA, 10 mM Sodium Phosphate, 100 mM KCl and 1 mM $MgCl_2$ at pH 7.2. Similar measurements were also taken with a limiting amount of RNA (40 nM) in an excess of TO1-Biotin (200 nM) and the results showed a similar trend.

5S-Mango RNA Synthesis and Transfection

RNA was transfected directly into 8-well chamber slides using the Lipofectamine-based CRISPRMAX reagent following the manufacturers guidelines (Invitrogen). Initially 125 nM RNA containing 10 mM Sodium Phosphate buffer (pH 7.2), 100 mM KCl and 1 mM $MgCl_2$ was incubated at room temperature followed by a 1:1 dilution in OptiMEM prior to transfection. The RNA transfected was incubated at 37° C. for 1 hour in complete growth medium.

Cell Fixation and Immunostaining

Cells were fixed in PBS containing 4% paraformaldehyde for 10 min on ice (Thermo Fisher) followed by permeabilization in 0.2% Triton X-100 for 10 min at room temperature. Cells were first blocked (2% BSA in PBS) for 30 min followed by primary antibody (1:50-1:500 dilutions) incubation for 120 min in blocking solution.

Primary antibodies used here were: Anti-Ribosomal Protein S6 (MAB5436, R&D Systems), Anti-ATP5B (ab14730, Abcam), Anti-GW182 (ab7052, Abcam), Anti-EEA-1 (ab70521, Abcam), Anti-LSm3 (NBP2-14206, Novus Biologicals), Anti-TIAR (sc-398372, Santa Cruz). Secondary antibodies used were Donkey Anti-mouse and Donkey Anti-Rabbit Alexa Fluor 680 (Molecular Probes). Primary antibodies were washed three times for 20 min each in blocking solution followed by incubation with secondary antibody at 1:500 dilution for 60 min, which was subsequently washed as above. After immunostaining the cells were washed three times for 5 min each with PKM buffer (10 mM Sodium Phosphate, 100 mM KCl and 1 mM $MgCl_2$) followed by a 10 min incubation in 200 nM TO1-Biotin diluted in PKM buffer before replacing with imaging media (10 mM Sodium Phosphate, 100 mM KCl and 1 mM $MgCl_2$ 1 µg/ml Hoechst 33258).

Live-Cell Imaging and Fluorescence Microscopy

To visualize the nuclear boundary in live cells, a plasmid expressing a fluorescently tagged histone protein (EBFP2-H2B-6, Addgene plasmid 55243) was transfected using FuGene 6 (Promega) 24 h prior to RNA transfection. RNA was transfected directly into 8-well chamber slides (Ibidi GmbH) as described above, with an additional pre-incubation step with 250 nM of TO1-Biotin prior to the addition of the CRISPRMAX transfection reagent. Following incubation of the RNA transfection, the cells were washed once with PBS and replaced with live-cell imaging media (Fluorobrite DMEM supplemented with 20 mM HEPES, Invitrogen). Live and fixed cell images were taken using a Zeiss Elyra wide-field microscope by exciting at 405 nm (Blue), 488 nm (Green) and 642 nm (Far-Red) and detecting at 420-480 nm, 495-550 nm and >650 nm, respectively. Live cells were maintained at 37° C. with 5% $CO_2$ in a stage top incubator (Tokai Hit). Images were processed using FIJI and spot detection analysis was performed on each maximum projection by the spot detector plugin in the ICY image analysis software, which detects significant foci with a pixel area 3×3 pixels.

REFERENCES

1. Nicoludis, J. M. et al. Optimized End-Stacking Provides Specificity of N-Methyl Mesoporphyrin IX for Human Telomeric G-Quadruplex DNA. J. Am. Chem. Soc. 134, 20446-20456 (2012).
2. Dolgosheina, E. V. et al. RNA Mango Aptamer-Fluorophore: A Bright, High-Affinity Complex for RNA Labeling and Tracking. ACS Chem. Biol. 9, 2412-2420 (2014).
3. Autour, A., Westhof, E. & Ryckelynck, M. iSpinach: a fluorogenic RNA aptamer optimized for in vitro applications. Nucleic Acids Res. 44, 2491-2500 (2016).

4. Warner, K. D. et al. Structural basis for activity of highly efficient RNA mimics of green fluorescent protein. Nat. Struct. Mol. Biol. 21, 658-663 (2014).
5. Huang, H. et al. A G-quadruplex—containing RNA activates fluorescence in a GFP-like fluorophore. Nat. Chem. Biol. 10, 686-691 (2014).
6. Shaner, N. C., Steinbach, P. A. & Tsien, R. Y. A guide to choosing fluorescent proteins. Nat. Methods 2, 905-909 (2005).
7. Jeng, S. C. Y., Chan, H. H. Y., Booy, E. P., McKenna, S. A. & Unrau, P. J. Fluorophore ligand binding and complex stabilization of the RNA Mango and RNA Spinach aptamers. RNA (2016). doi:10.1261/rna.056226.116
8. Paige, J. S., Wu, K. Y. & Jaffrey, S. R. RNA Mimics of Green Fluorescent Protein. Science 333, 642-646 (2011).
9. Filonov, G. S., Kam, C. W., Song, W. & Jaffrey, S. R. In-Gel Imaging of RNA Processing Using Broccoli Reveals Optimal Aptamer Expression Strategies. Chem. Biol. 22, 649-660 (2015).
10. Karunatilaka, K. S. & Rueda, D. Post-transcriptional modifications modulate conformational dynamics in human U2-U6 snRNA complex. RNA 20, 16-23 (2014).
11. Smirnov, A., Entelis, N., Martin, R. P. & Tarassov, I. Biological significance of 5S rRNA import into human mitochondria: role of ribosomal protein MRP-L18. Genes Dev. 25, 1289-1305 (2011).
12. Ryckelynck, M. et al. Using droplet-based microfluidics to improve the catalytic properties of RNA under multiple-turnover conditions. RNA 21, 458-469 (2015).
13. Lorsch, J. R. & Szostak, J. W. In vitro selection of RNA aptamers specific for cyanocobalamin. Biochemistry (Mosc.) 33, 973-982 (1994).

EXAMPLES

Example 1: Crystal Structures of the Mango-II RNA Aptamer Reveal Heterogeneous Fluorophore Binding and Guide Engineering of Variants with Improved Selectivity and Brightness Several aptamers that induce fluorescence of their cognate small molecules by >1000-fold, and that can be used in vivo as RNA analogues of fluorescent proteins have been described.1-3 Among these, RNA Mango is noteworthy because of its small size (<30 nucleotides) and its high affinity for the thiazole orange-derived fluorophore, TO1-Biotin (Kd=3.1 nM). Moreover, its complex with the related fluorophore TO3-Biotin (Kd=8 nM) is one of the most red-shifted fluorogenic tags described to date, having an emission maximum of longer wavelength than the fluorescent protein mPlum.4 The Co-crystal structure of RNA Mango revealed a three-tiered G-quadruplex. TO1-Biotin binds on one of its flat faces, with each of its three heterocycles, benzothiazole (BzT), mehtylquinoline (MQ) and biotin sequestered under an unpaired nucleotide.5,6 Mango-II was recently obtained by subjecting the final pool of the RNA Mango selection to compartmentalization coupled to fluorescence sorting.7 Compared to the original aptamer (hereafter Mango-I), the new RNA is brighter (11,000 M-1 cm-1 vs. 17,000 M-1 cm-1 for Mango-I and Mango-II, respectively), and binds to both TO1-Biotin and TO3-Biotin (FIG. 35A) with higher affinity (Kd=1.1±0.3 nM and 1.4±0.3 nM, respectively). To elucidate the structural basis for the enhanced properties of Mango-II, and as a starting point for structure-guided engineering, we have now determined its co-crystal structures in complex with TO1-Biotin (FIG. 35B,C) and TO3-Biotin (FIG. 36) at 2.9 Å and 3.0 Å resolution, respectively (Table 6).

TABLE 6

Summary of crystallographic statistics

|  | Mango-II-TO1 | Mango-II-TO3 |
|---|---|---|
| Data collection |  |  |
| Space group | $C222_1$ | $C222_1$ |
| Cell dimensions |  |  |
| a, b, c (Å) | 36.83, 182.41, 107.49 | 37.10, 181.76, 108.290 |
| α, β, γ (°) | 90, 90, 90 | 90, 90, 90 |
| Resolution (Å) | 107.49-2.57 (2.68-2.57)$^a$ | 46.52-2.99 (3.2-2.99)$^a$ |
| $R_{merge}$ | 0.058 (>1) | 0.098 (0.93) |
| <I>/<σ(I)> | 18.6 (0.9) | 16.4 (0.5) |
| Completeness (%) | 98.8 (90.0) | 99.8 (99.6) |
| Redundancy | 8.8 (7.9) | 10.5 (4.1) |
| Refinement |  |  |
| Resolution (Å) | 91.21-2.90 (2.99-2.90) | 46.52-3.00 (3.19-3.00) |
| No. reflections | 15464 (1257) | 7735 (1268) |
| $R_{work}/R_{free}$ | 18.58/23.06 | 18.99/25.51 |
| No. atoms | 2453 | 2339 |
| RNA | 2283 | 2283 |
| TO1-Biotin | 162 | 48 |
| Ions | 8 | 8 |
| Water | 0 | 0 |
| B-factors (Å$^2$) | 75.32 | 57.38 |
| RNA | 75.29 | 57.53 |
| TO1-Biotin | 75.95 | 51.52 |
| Ions | 62.0 | 42.42 |
| Water | N.A. | N.A. |
| R.m.s deviations |  |  |
| Bond lengths (Å) | 0.007 | 0.006 |
| Bond angles (°) | 1.437 | 1.200 |

$^a$Values in parentheses are for highest-resolution shell.
One crystal was used for each data set.

Figure 37:
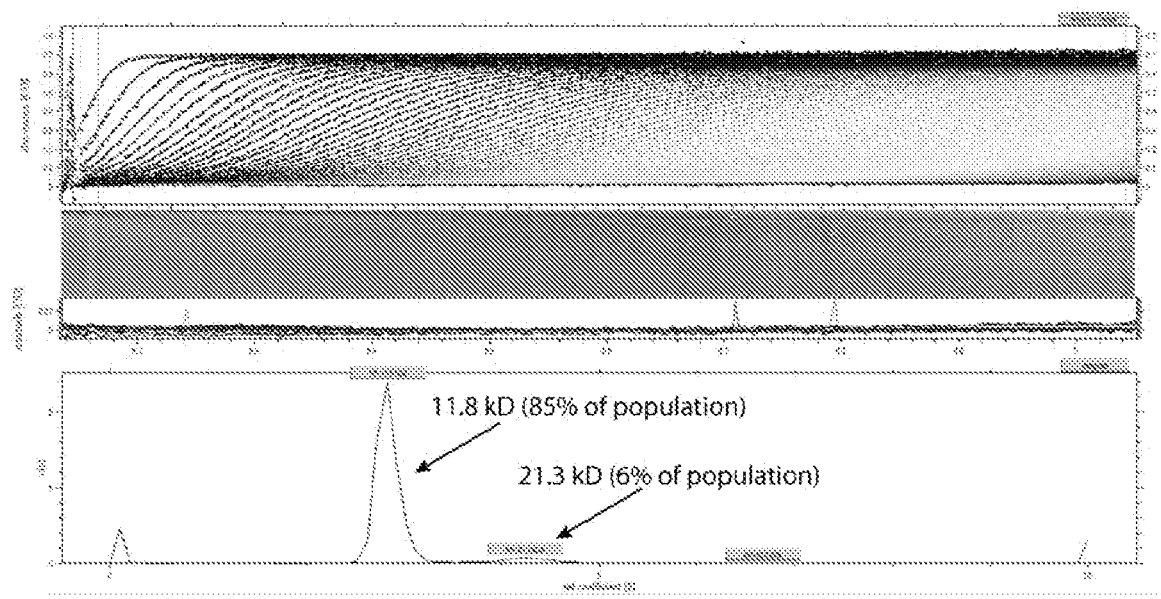

The two complexes crystallized in similar unit cells with three crystallographically independent RNAs (chains A, B, C) in the asymmetric unit (A.U.). Overall, the three RNAs in each structure are very similar (rmsd ~0.7 Å for all non-hydrogen RNA atoms), and so are the RNAs in complex with the two different fluorophores (rmsd ~0.2 Å between the best-ordered chains in each structure; the coordinate precisions of the two structures are 0.42 Å and 0.40 Å, respectively). The folds of Mango-I and Mango-II are overall similar, and this similarity extends to crystal packing, in which adjacent aptamers stack pairwise through their fluorophore-distal quadruplex faces. Nonetheless, and as in the case of Mango-II, analytical ultracentrifugation indicates the aptamer RNA is monomeric in solution (FIG. 37).

Mango-II has an almost identical melting profile in both the presence and absence of TO1-Biotin and is more thermostable than Mango-I.7 In addition, Mango-II is remarkably formaldehyde resistant; Mango-II reacted with formaldehyde, can still bind and induce fluorescence of TO1-Biotin. Together, these data suggest that the Mango-II aptamer has a pre-organized binding pocket.

Three structural differences between Mango-I and Mango-II are consistent with a higher stability of the latter RNA and its improved fluorophore affinity. First, each guanine in the T3 G-quartet is isolated from the T2 G-quartet by one of four adenine containing propeller loops (FIG. 38B). This approximate four-fold rotational symmetry is lacking in Mango-I where one T3 guanine buckles 30° out of plane of the other guanines.5 Second, the GAAAA junction between the P1 duplex and the quadruplex of Mango-II appears to have more hydrogen bonding interactions than that of Mango-I (FIG. 51). Consistent with a higher stability of the Mango-II junction, all P1 helices in the A.U. are crystallographically resolved. In contrast, only one of the two P1 s in the Mango-! A.U. exhibited electron density. Third, the T1 G-quartet (distal from the fluorophore) of Mango-II is augmented into a hexad by two adenines, A14 and A25 (FIG. 38A). The corresponding T1 in Mango-I is augmented by one adenine into only a pentad. 5 The higher stability of Mango-II may reflect the higher temperature at which it was selected (45° C. vs. 37° C. for Mango-I).

The five adenines in the four propeller loops and the planar T3 quadruplex they create together define the fluorophore binding pocket of Mango-II. In this complex, the MQ and BzT of TO1-Biotin are coplanar and, in chains A and B, stack on G13 and G29 of T3, respectively (FIG. 39A). The binding modes of the headgroup of the fluorophore in the Mango-I and Mango-II complexes are near-mirror images. When seen from above the plane of T3, the BzT and MQ heterocycles are arranged clockwise and counter-clockwise in the two structures, respectively. As a result, the long axes of the BzT and MQ heterocycles are parallel and perpendicular to those of the T3 guanines on which they stack in the Mango-I and Mango-II complexes, respectively (ref. 5, FIG. 40). The perpendicular stacking arrangement is also present in chain C of the Mango-II structure but the heterocycles of the fluorophore are rotated by 90° around the 4-fold symmetry axis of the G-quartet with respect to that found in the A and B chains (FIG. 39B). Concomitant with this rotation, four of the flap adenines of chain C of the A.U. (A17, A22, A23, and A28) adopt different conformations from those of chains A and B (FIG. 3B). A17 reorients from anti to syn; A22 and A28 become disordered; and A23 reorients from syn to anti. In additional contrast to the Mango-I structure, electron density for atoms 1' through 7' of the PEG linker is coplanar with the T3 guanine layer, with the biotin moiety being disordered in all three complexes. The increased coplanarity of the TO1 heterocycles is consistent with the higher quantum yield of Mango-II-TO1-Biotin complex (0.21 vs. 0.14 for the corresponding Mango-I complex).

In the structure of Mango-II bound to TO3-Biotin, electron density corresponding to the fluorophore was only observed for the headgroup (BzT, MQ, and the trimethine linker), and only in RNA chains A and B (FIGS. 39 C,D). Notably, in the two RNA chains with bound TO3-Biotin, the nucleobase of A22 stacks directly on G24 of T3. In chain B, A22 also is in van der Waals contact with the methine linker of TO3-Biotin. These interactions may further stabilize the complex, and the packing of A22 observed in chain B may directly promote fluorescence of TO3-Biotin by stabilizing a coplanar conformation BzT, MQ, and the extended methine linker of this fluorophore.

Highly selective fluorogenic RNAs would facilitate development of orthogonal fluorescent tags. The structural heterogeneity revealed by our Mango-II TO1-Biotin and TO3-Biotin co-crystal structures, as well as the comparable affinity of the aptamer for the two fluorophores, suggests that the fluorophore binding pocket of this aptamer is not highly stereoselective. To increase selectivity of Mango-II, we constructed mutants focusing on residue A22, which in our structures is conformationally plastic and appeared to have the most potential to influence TO3-Biotin discrimination. Mutants were analyzed for affinity and fluorescence enhancement of TO1-Biotin and TO3-Biotin (Table 8 & 9). Mutation to guanine reduced the binding affinity and fluorescence enhancement of both TO1-Biotin and TO3-Biotin (Table 8 & 9). Such an outcome is not unexpected, as G-quadruplex nucleic acids can undergo alternative folding when additional guanine bases are present.8 However, mutation to uridine or cytosine maintained the binding affinity for TO1-Biotin (0.9 nM) while decreasing the affinity of TO3-Biotin from ~1.4 nM to ~5.0 nM (Table 8 & 9). Unexpectedly, these mutations also increased the fluorescence enhancement of TO1-Biotin by 18% while decreasing the fluorescence enhancement of TO3-Biotin by 25% (Table 8 & 9).

TABLE 7

Summary of crystallographic statistics

| | Mango-II-A22U-TO1 |
|---|---|
| Data collection | |
| Space group | $C222_1$ |
| Cell dimensions | |
| a, b, c (Å) | 36.86, 181.03, 109.06 |
| α β, γ (°) | 90, 90, 90 |
| Resolution (Å) | 46.38-2.80 (2.95-2.80)[a] |
| $R_{merge}$ | 0.102 (0.956) |
| $<I>/<\sigma(I)>$ | 18.6 (1.1) |
| Completeness (%) | 99.8 (99.6) |
| Redundancy | 11.3 (8.7) |
| Refinement | |
| Resolution (Å) | 46.38-2.80 (2.95-2.80) |
| No. reflections | 9216 (1254) |
| $R_{work}/R_{free}$ | 18.59/23.69 |
| No. atoms | 2511 |
| RNA | 2349 |
| TO1-Biotin | 162 |
| Ions | 8 |
| Water | 0 |
| B-factors (Å$^2$) | 59.34 |
| RNA | 59.37 |
| TO1-Biotin | 58.74 |
| Ions | 54.6 |
| Water | N.A. |
| R.m.s deviations | |
| Bond lengths (Å) | 0.008 |
| Bond angles (°) | 1.55 |

[a]Values in parentheses are for highest-resolution shell.
One crystal was used for each data

TABLE 8

Binding and fluorescence of Mango-II and mutants to TO1-B and its derivatives.

| RNA | Ligand | $K_D$ (nM) | $FI_E$ |
|---|---|---|---|
| Mango II - WT | TO1-B | 1.1 ± 0.3 | 1303 ± 20 |
| Mango II - A22U | TO1-B | 0.9 ± 0.4 | 1543 ± 24 |
| Mango II - A22C | TO1-B | 0.9 ± 0.2 | 1407 † |
| Mango II - A22G | TO1-B | 6.4 ± 1.5 | 1224 † |
| Mango II - WT | TO3-B | 1.4 ± 0.3 | 61 ± 2 |
| Mango II - A22U | TO3-B | 5.0 ± 2.8 | 46 ± 3 |
| Mango II - A22C | TO3-B | 5.1 ± 1.4 | 37 † |
| Mango II - A22G | TO3-B | 7.6 ± 3.7 | 52 † |
| Mango II - A12U | TO1-B | 0.40 ± 0.07 | 1342 † |
| Mango II - A17U | TO1-B | 1.00 ± 0.16 | 1237 † |
| Mango II - A15U A20U A25U A26U A31U | TO1-B | 1.92 ± 0.39 | 1133 † |
| Mango II - A15U A20U A25U | TO1-B | 0.76 ± 0.24 | 1329 † |
| Mango II - WT | TO1-OAc | 56 ± 2 | 258 ± 10 |
| Mango II - A22U | TO1-OAc | 43 ± 3 | 315 ± 4 |
| Mango II - WT | TO1-ME | 2.41 ± 0.54 | 401 ± 6 |
| Mango II - A22U | TO1-ME | 4.81 ± 1.02 | 302 ± 6 |
| Mango II - WT | TO1-PA | 1.04 ± 0.57 | 493 ± 5 |
| Mango II - A22U | TO1-PA | 2.21 ± 1.09 | 275 ± 3 |

TABLE 8-continued

Binding and fluorescence of Mango-II and
mutants to TO1-B and its derivatives.

| RNA | Ligand | $K_D$ (nM) | $FI_E$ |
|---|---|---|---|
| Mango II - WT | TO1-PE | 0.37 ± 0.06 | 783 ± 13 |
| Mango II - A22U | TO1-PE | 1.00 ± 0.13 | 825 ± 14 |

† Indicates the fluorescence enhancement was calculated relative to wt from the binding titration.

To understand how the Mango-II A22U mutation results in increased TO1-Biotin fluorescence enhancement, we determined the co-crystal structure of this complex at 2.8 Å resolution (Table 7). The RNA structure is generally unchanged from that of the wild-type. The nucleobase of U22 is ordered but projects into solvent rather than interacting with T3. TO1-Biotin adopts the same orientation in all three chains in the A.U. with Bzt and MQ stacking on G29 and G13, respectively (FIGS. 39 E,F). Among our crystal structures, the binding pocket of the mutant is better ordered than that of either wild-type complex as judged by the mean real-space correlation coefficient (Table 10). Ligand-RNA shape complementarity (SC) analysis9 of each co-crystal structure indicates that the A22U binding pocket conforms to TO1-Biotin better than wildtype, with SC statistics of 0.796 (rms=0.004) and 0.750(rms=0.009), respectively. The SC statistic of Mango-II-TO3-Biotin complex, 0.800 (rms=0.019), was similar to that of Mango-II (A22U)-TO1-Biotin.

TABLE 9

RNA sequence table.

| # | RNA Name | Sequence | SEQ ID NO |
|---|---|---|---|
| 1 | Mango II-wt | GCGUACGAAG GAGAGGAGAG GAAGAGGAGA GUACGC | 6902 |
| 2 | Mango II-A22U | GCGUACGAAGGAGAGGAGAGGUAGAGGAGAGU ACGC | 6903 |
| 3 | wt* (8 bp) | GGCACGUACGAAGGAGAGGAGAGGAAGAGGAG AGUACGUGC | 6904 |
| 4 | A22U* | GGCACGUACGAAGGAGAGGAGAGGUAGAGGAG AGUACGUGC | 6905 |
| 5 | A22C* | GGCACGUACGAAGGAGAGGAGAGGCAGAGGAG AGUACGUGC | 6906 |
| 6 | A22G* | GGCACGUACGAAGGAGAGGAGAGGGAGAGGAG AGUACGUGC | 6907 |
| 7 | A12U* | GGCACGUACGAAGGUGAGGAGAGGAAGAGGAG AGUACGUGC | 6908 |
| 8 | A17U* | GGCACGUACGAAGGAGAGGUGAGGAAGAGGAG AGUACGUGC | 6909 |
| 9 | A15U A20U A25U A26U A31U* | GGCACGUACGAAGGUGAGGUGAGGUUGAGGU GAGUACGUGC | 6910 |
| 10 | A15U A20U A25U* | GGCACGUACGAAGGUGAGGUGAGGUAGAGGAG AGUACGUGC | 6911 |

TABLE 10

Mean CC values for binding pocket residues
in respective complexes and chains.

| | Mango-II-TO1 | Mango-II-TO3 | Mango-II-A22U-TO1 |
|---|---|---|---|
| Chain A | 0.9282 | 0.9433 | 0.9605 |
| Chain B | 0.9181 | 0.9201 | 0.9431 |
| Chain C | 0.8606 | 0.8790 | 0.9248 |

Binding pocket residues are defined as G13, G18, G24, G29, A12, A17, A22, A23 and A28

To extend our crystallographic observations into solution conditions, we examined the fluorescence lifetimes of the wildtype and A22U mutant Mango-II RNAs in complex with TO1-Biotin. The A22U mutation increases the average lifetime of the emission from 1.51 (±0.06) ns to 1.92 (±0.03) ns. The lifetime of the Mango-II-TO1-Biotin complex has two components, and both are increased in the mutant compared to the wild-type: the first from 0.52 (±0.02) ns to 0.72 (±0.01) ns, and the second from 2.33 (±0.12) ns to 2.904 (±0.001) ns (FIG. 41, Table 11). Our X-ray structures show that the wild-type Mango-II has two different modes of TO1-Biotin binding, while the A22U mutant is more homogeneous (FIG. 39). The longer lifetimes of the mutant are consistent with this, and in particular suggest reduced torsional freedom in the atoms of the methine linker, as has been shown previously for other complexes of thiazole orange with nucleic acids.10

TABLE 11

Parameters from the analysis of fluorescence lifetime data.

| Parameter | TO1-Biotin | Mango II wt | Mango II A22U |
|---|---|---|---|
| $\tau_1$ (ns) | 0.11 | 0.52 (±0.02) | 0.72 (±0.01) |
| $\alpha_1$ (%) | 63 | 45 (±3) | 45 (±2) |
| $\tau_2$ (ns) | 0.50 | 2.33 (±0.12) | 2.904 (±0.001) |
| $\alpha_2$ (%) | 25 | 55 (±3) | 55 (±2) |
| $t_3$ (ns) | 2.63 | \ | \ |
| $\alpha_3$ (%) | 12 | \ | \ |
| $\tau_i$ (ns) * | 1.77 | 2.05 (±0.09) | 2.53 (±0.02) |
| $\tau_a$ (ns) * | 0.51 | 1.51 (±0.06) | 1.92 (±0.03) |

* $\tau_i$ is the intensity-weighted average lifetime, and $\tau_a$ is the amplitude-weighted average lifetime calculated from the data presented above. The latter is used in the text when discussing and comparing the TCSPC data for the different structures.

The Inventor's mutant co-crystal structure shows no direct contacts between U22 and TO1-Biotin. To gain further insight into how the U22 mutation improves Mango-II properties, we examined the effect of varying the length of the linker between the thiazole orange and biotin moieties of TO1-Biotin. We determined the affinity and fluorescence enhancement of four compounds: TO1-OAc (TO1-acetate), TO1-ME (TO1-methylester), TO1-PA (TO1-propanylamide), TO1-PE (TO1-pentenoylester) (FIG. 42, Table 8 & 9). Binding affinity and fluorescence enhancement of TO1-OAc is drastically diminished, and nearly identical between the wild-type and A22U mutant. However, the TO1-ME and TO1-PA exhibit greater fluorescence enhancement and binding affinity with the wild-type than with A22U. This suggests that in the absence of an extended linker, the A22 stabilizes the binding pocket, presumably by stacking on G24 as observed in chain B of the Mango-I-TO3-Biotin co-crystal structure (FIGS. 39 C,D). Further extension of the linker stabilizes the binding pocket by stacking on T3 but becomes sterically hindered by a bulky purine in position 22. The A22U mutation would limit steric clashes while preventing misfolding of the G-quadruplex core. Thus, the improved properties of the Mango-II A22U mutant may arise from improved packing of the linker of the fluorophore with an RNA with a homogeneous or predominant conformation.

The inventors demonstrate that Mango-II is a versatile platform for fluorescence enhancement of thiazole-orange derived fluorophores, and have shown that variants of this RNA tag, designed with the aid of crystal structures, have improved properties. Analysis of the fluorophore-RNA shape complementarity of each of our structures reveals that fluorescence enhancement correlates directly with the SC statistic. The Mango-II-TO3-Biotin and Mango-II(A22U)-TO1-Biotin complexes both yield similarly high SC statistics, possibly indicating an upper limit to the shape complementarity attainable for this type of complex. The high SC statistic observed for the A22U mutant-TO1-Biotin complex also correlates with improved binding affinity, fluorescence enhancement and fluorescence lifetime. Fluorescence binding studies on TO1-Biotin variants independently suggest that these improvements are due to removal of steric constraints on the ligand by the transversion mutation to a pyrimidine, consistent with our crystallographic analysis. By achieving enhanced fluorescence properties through improved ligand-RNA packing and structural homogeneity, this work demonstrates that even functionally selected fluorogenic RNAs can potentially be improved through detailed structural and mechanistic analysis.

REFERENCES

1. Paige, J. S.; Wu, K. Y.; Jaffrey, S. R., RNA mimics of green fluorescent protein. Science 2011, 333 (6042), 642-646.
2. Dolgosheina, E. V.; Jeng, S. C. Y.; Panchapakesan, S. S. S.; Cojocaru, R.; Chen, P. S. K.; Wilson, P. D.; Hawkins, N.; Wiggins, P. A.; Unrau, P. J., RNA Mango aptamer-fluorophore: A bright, high-affinity complex for RNA labeling and tracking. ACS Chem. Biol. 2014, 9 (10), 2412-2420.
3. Tan, X. H.; Constantin, T. P.; Sloane, K. L.; Waggoner, A. S.; Bruchez, M. P.; Armitage, B. A., Fluoromodules consisting of a Promiscuous RNA aptamer and red or blue fluorogenic cyanine dyes: selection, characterization, and bioimaging. J. Am. Chem. Soc. 2017, 139 (26), 9001-9009.
4. Rodriguez, E. A.; Campbell, R. E.; Lin, J. Y.; Lin, M. Z.; Miyawaki, A.; Palmer, A. E.; Shu, X. K.; Zhang, J.; Tsien, R. Y., The growing and glowing toolbox of fluorescent and photoactive proteins. Trends Biochem. Sci. 2017, 42 (2), 111-129.
5. Trachman, R. J.; Demeshkina, N. A.; Lau, M. W. L.; Panchapakesan, S. S. S.; Jeng, S. C. Y.; Unrau, P. J.; Ferré-D'Amaré, A. R., Structural basis for high-affinity fluorophore binding and activation by RNA Mango. Nat Chem Biol 2017, 13 (7), 807-813.
6. Trachman, R. J.; Truong, L.; Ferre-D'Amare, A. R., Structural principles of fluorescent RNA aptamers. Trends Pharmacol. Sci. 2017, 38 (10), 928-939.
7. Autour A et al., Fluorogenic RNA Mango aptamers for imaging small non-coding RNAs in mammalian cells Nat. Comm. 2018 (In Press), DOI: 10.1038/s41467-018-02993-8.
8. Phan, A. T.; Kuryavyi, V.; Gaw, H. Y.; Patel, D. J., Small-molecule interaction with a five-guanine-tract G-quadruplex structure from the human MYC promoter. Nat. Chem. Biol. 2005, 1 (3), 167-173.
9. Lawrence, M. C.; Colman, P. M. Shape complementarity at protein/protein interfaces. JMB 1993, 234, 946-950.
10. Jarikote, D. V.; Krebs, N.; Tannert, S.; Roder, B.; Seitz, O., Exploring base-pair-specific optical properties of the DNA stain thiazole orange. Chem. Eur. J. 2007, 13, 300-310.
11. Leontis, N. B.; Westhof, E., Geometric nomenclature and classification of RNA base pairs. RNA 2001, 7 (4), 499-512.

Example 2—an RNA Aptamer of Unusual Structural Complexity Induces Bright Fluorescence of a Thiazole Orange Derivative In order to elucidate the molecular basis for the unusually bright fluorescence of the Mango-III-TO1-Biotin complex, and as a starting point for structure-guided optimization of this tool for live-cell imaging of RNAs, we have now determined its co-crystal structure at 2.35 Å resolution, revealing a compact aptamer RNA of unusual structural complexity. The thiazole orange (TO) headgroup of the fluorophore is constrained between a long-range Watson-Crick base pair and a G-quadruplex to a planar conformation that would maximize its fluorescence, thereby explaining the high quantum yield of Mango-III.

Results

Overall Structure of Mango-III Bound to TO1-Biotin

A 38-nt construct comprising the conserved 28-nt Mango-III core flanked by nucleotides presumed to form a 5-base pair Watson-Crick duplex was co-crystalized with TO1-Biotin. The structure was solved by the single-wavelength anomalous dispersion (SAD) method using data from an iridium derivative (Table 12, Methods).

TABLE 12

Summary of crystallographic statistics

| | Mango-III-TO1 | Mango-III-A15U-TO1 | SuperMango-III-TO1 |
|---|---|---|---|
| Data collection | | | |
| | | | |
| Space group | $P2_12_12_1$ | H3 | $I4_122$ |
| Cell dimensions | | | |
| | | | |
| a, b, c (Å) | 63.03, 67.59, 76.67 | 91.95, 91.95, 161.69 | 53.27, 53.27, 188.04 |
| α β, γ (°) | 90, 90, 90 | 90, 90, 120 | 90, 90, 90 |
| Resolution (Å) | 46.10-2.35 (2.39-2.35)$^a$ | 45.97-2.90 (2.98-2.90)$^a$ | 40.59-1.51 (1.55-1.51) |
| $R_{merge}$ | 0.06 (>1) | 0.038 (0.91) | 0.05 (>1) |
| $<I>/<\sigma(I)>$ | 50.6 (1.2) | 10.3 (1.0) | 20.9 (1.5) |
| Completeness (%) | 99.9 (100) | 98.5 (99.0) | 99.9 (98.6) |
| Redundancy | 7.2 (7.1) | 2.3 (2.2) | 10.2 (10.6) |

TABLE 12-continued

Summary of crystallographic statistics

| | Mango-III-TO1 | Mango-III-A15U-TO1 | SuperMango-III-TO1 |
|---|---|---|---|
| Refinement | | | |
| Resolution (Å) | 38.3-2.35 (2.43-2.35) | 45.98-2.90 (3.03-2.90) | 40.59-1.55 (1.61-1.55) |
| No. reflections | 12717 (1237) | 11055 (1224) | 20013 (1951) |
| $R_{work}/R_{free}$ | 19.28/20.92 | 19.29/23.07 | 16.8/19.12 |
| No. atoms | 1806 | 3171 | 996 |
| RNA | 1632 | 2283 | 787 |
| TO1-Biotin | 107 | 93 | 52 |
| Ions | 9 | 5 | 8 |
| Water | 25 | 4 | 143 |
| B-factors (Å$^2$) | 76.8 | 79.75 | 33.90 |
| RNA | 76.91 | 80.17 | 32.07 |
| TO1-Biotin | 74.29 | 67.45 | 34.09 |
| Ions | 79.7 | 65.02 | 33.35 |
| Water | 79.1 | 58.93 | 41.81 |
| R.m.s deviations | | | |
| Bond lengths Å | 0.006 | 0.007 | 0.005 |
| Bond angles | 1.265 | 1.541 | 1.06 |

[a]Values in parentheses are for highest-resolution shell. One crystal was used for each data set.

Figure 44:
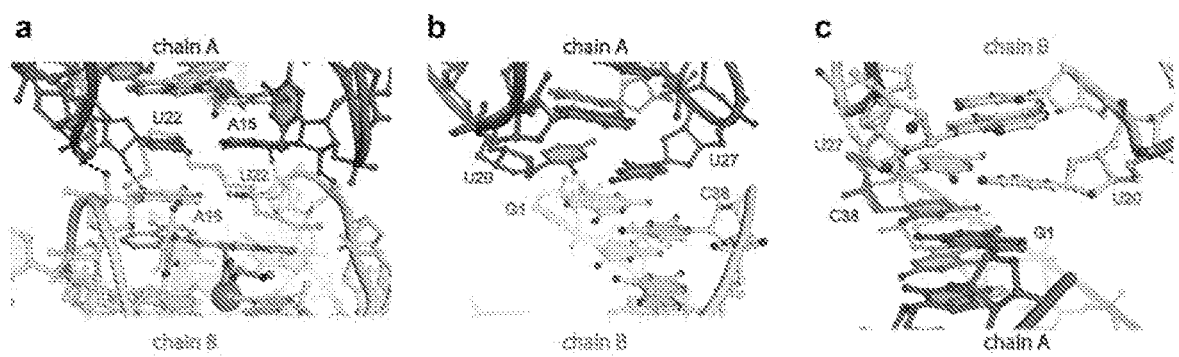
Figure 45:
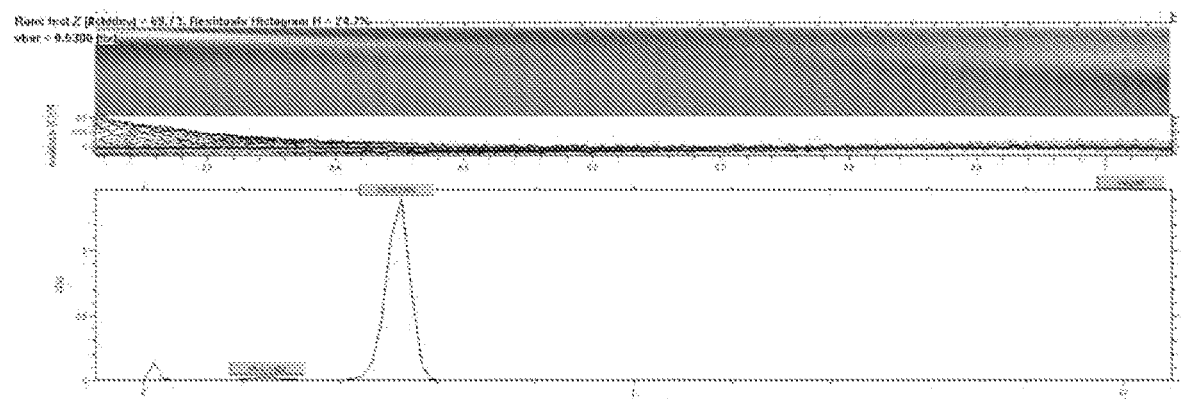

The crystallographic asymmetric unit (ASU) contains two similar RNA-fluorophore complexes (RMSD=0.15 Å for all non-hydrogen atoms). The two RNAs in the ASU each make three crystal contacts involving duplex stacking (FIG. 44). Analytical ultracentrifugation and dynamic light scattering (FIG. 45) however, indicate that Mango-III is a monomer in solution.

Figure 46D:
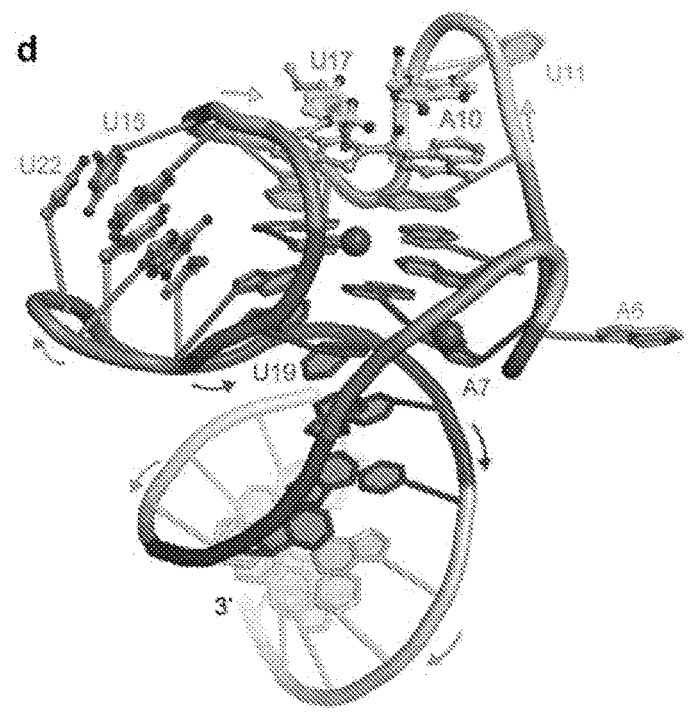

The structure of Mango-III (FIG. 46 b,c) is organized around a two-tiered G-quadruplex with all-parallel connectivity, except for G18 of the top tier (T2), which is antiparallel. This quadruplex, which coordinates a canonical axial K+ ion (MA), stacks on a base triple, which in turn stacks coaxially on an A-form duplex (paired element P1). Two nucleotides from the loop connecting G14 and G18 of T2, and four nucleotides from the loop that follows G20 (the last of the eight guanines of the G-quadruplex) form the three base pairs of a second helix (P2) that is juxtaposed with the G-quadruplex. U17, which is extruded from the middle of P2, forms a trans Watson-Crick pair with A10 from the propeller loop that connects G9 to G13, on the diagonally opposite side of the T2 G-quartet. The benzothiazole (BzT) and methylquinoline (MQ) of the bound TO1-Biotin are sandwiched between the A10•U17 tertiary base pair and T2 of the G-quadruplex. Reflecting the high structural complexity of this aptamer RNA, only two nucleobases (A6, U11) of the 28-nucleotide conserved core of Mango-III do not share at least a hydrogen bond with another nucleobase. In comparison, six of the 22 nucleotides of the Mango-I core are fully unpaired (FIG. 46 c).

A coaxial duplex-triplex-quadruplex stack Mango-I is comprised of a three-tiered G-quadruplex flexibly connected to its adjacent A-form duplex P1 through a GAA"A-tetraloop-like junction (A denotes the site of insertion of the quadruplex). The corresponding residues of Mango-III adopt a completely different structure. Instead of folding like the first three nucleotides of a GNRA tetraloop, G1, A2 and A3 of Mango-III continue the duplex structure of P1 by Watson-Crick base-pairing with complementary nucleotides at the 3' end of the aptamer (FIG. 46 d). A25 of Mango-III (which corresponds in sequence to the last tetraloop residue of Mango-I) forms an expanded base triple with A7 (which is part of the propeller loop between G5 and G8 of the Mango-III quadruplex) and U19 (which connects G18 an G20 of the Mango-III quadruplex) (FIG. 46 b, FIG. 47a). The A7•U19•A25 triple is unusual because only two direct hydrogen bonds connect the three nucleobases, but these each also hydrogen bonds through its Watson-Crick face to a common water molecule (W1) that lies approximately at the center of the triple.

The expanded A7•U19•A25 triple links the P1 duplex with the quadruplex of Mango-III through three sets of interactions. First, the base triple stacks below the T1 of the quadruplex and above the closing A3•U26 base pair of P1. Second, the 2'-OH of U26 donates a hydrogen bond to the N1 of A7 of the triple, in effect expanding it to a pseudo-tetrad. Third, a hydrated cation (MB, Sr2+ in this crystal structure, but likely Mg2+ under physiological conditions) and a network of ordered water molecules connects the phosphate of A7 to the minor grooves of both, A3 and G4, thereby spanning the duplex-quadruplex junction. Overall, these interactions likely produce a rigid connection between P1 and the G-quadruplex moieties of Mango-III, which is consistent with the identical (within coordinate precision) relative arrangements of the two elements in the two crystallographically independent aptamer RNAs in the A.U.

A Partially Parallel Non-Canonical Duplex

The P2 duplex of Mango-III is unique because of the chain direction of its two strands, and because each of its three base pairs is non-canonical. The backbones of the trans Watson-Crick U15•U22 and trans Hoogsteen A16•A23 base pairs are parallel. The third base pair is formed between U24 and G21, whose backbones are locally anti-parallel, being on opposite ends of the same loop connecting G20 of T1 (the last guanine of the G-quadruplex) to A25 of the base triple. The G21•U24 pair is formed in cis, and comprises a single hydrogen bond. The unusual structure of the P2 duplex is reflected in variable C1'-C1' distances (8.5 Å, 11.4 Å and 12.6 Å for the three pairs) that differ from that typical for canonical antiparallel A-form RNA duplexes (10.7 Å), and appears to be stabilized by a cross-strand stacking of A16 on G21. This latter interaction gives rise to two reciprocal hydrogen bonds between the N1 of A16 and the 2'-OH of G21, and the O6 of G21 and the 2'-OH of A16.

Formation of a duplex such as P2 between nucleotides in a propeller loop of a G-quadruplex and residues 3' to it is unusual. P2 contributes to the overall structure of Mango-III and formation of its fluorophore binding pocket in three important ways. First, because P2 is followed immediately by A25, formation of the duplex anchors the 2-tiered G-quadruplex onto the base triple. Second, G18 and G20 form the only non-contiguous and anti-parallel guanine stack in the Mango-III G-quadruplex, and P2 anchors the backbones of these two nucleotides next to each other. This may be further facilitated by a hydrogen bond between the pro-Rp non-bridiging phosphate oxygen (NBPO) of U10 and the 2'-OH of G14 from the adjacent guanine stack (FIG. 49 a). Third, P2 helps position U17 of the tertiary base pair in the fluorophore binding pocket of Mango-III, where it plays a functionally essential role.

The TO1-Biotin-Binding Site of Mango-III

Unbiased residual electron density corresponding to the BzT and MQ heterocycles as well as the four proximal atoms of the PEG linker of TO1-Biotin unambiguosly located the TO headgroup between T2 of the G-quadruplex and the tertiary A10•U17 trans Watson-Crick base pair (FIG. 49 b) A strong anomalous difference Fourier feature corroborated the location of the sulfur atom of BzT. Unlike in its Mango-I complex, where the planes of BzT and MQ subtended a 45° angle, and the biotin moiety stacked on the G-quadruplex and hemmed in the MQ ring, when bound to Mango-III the BzT and MQ rings are either coplanar (chain B) o modestly angled (23°, chain A), and the biotin projects out into solvent where it is presumed disordered. A further distinction between the Mango-I and Mango-III complexes is that whereas in the former the sulfur of BzT projects outward from the quadruplex, it lies at the center of T2 in the latter, where it is in van der Waals contact with the 06 of G18.

To test the functional significance of the tertiary A10•U17 base pair of Mango-III, we generated all sixteen combinations of nucleotides at these two positions, and examined their effect on TO1-Biotin binding and fluorescence enhancement (FIG. 52). With one exception, these mutations resulted in a least a 10-fold decrease in binding affinity and more than a 24% loss in fluorescence enhancement. The exception was the A10U point mutant, which not only exhibited TO1-Biotin binding affinity indistinguishable from that of the Mango-III wild-type, but also a 22% higher fluorescence enhancement. Thus, the tertiary base pair of Mango-III is important for fluorescence enhancement, and two of the sixteen possible nucleotide pairs yield bright fluorescence. Binding of TO1-Biotin to Mango-III appears to be further stabilized by U12, whose nucleobase is perpendicular to the T2 and A10-U17 planes, and where it hydrogen bonds through its N3 to the N3 of A10 and through its 2'-OH to the pro-Sp NBPO of G14 (FIG. 49 a,b). The nucleobase of this perpendicular U12 is in van der Waals contact with the proximal atoms of the PEG linker of TO1-Biotin. Previous characterization of Mango-III showed that the U12C mutant was 40% less fluorescent. We made the U12A and an abasic residue 12 variants, and found that they exhibited greater than 10-fold loss of affinity and greater than 45% loss in fluorescence enhancement. Thus, U12 appears to provide optimal interactions, both intramolecular and with the bound fluorophore.

Structure of the Enhanced Mango-III(A10U) Mutant

To determine the structural basis of the improvement in fluorescence resulting from the A12U mutation of Mango-III, we determined the crystal structure of this variant in complex with TO1-Biotin at 2.9 Å resolution (Table 1, Methods, and FIG. 4c, d). The mutant crystallized with four independent aptamer-fluorophore complexes in the A.U. The overall structures of the four chains are similar, but two of them (chains B and D) have partially disordered P2 helices where the cross-strand-stacked A16 and G21 are ordered, but U15, A23 and U24 are partially disordered. In all four chains, the U10 base resulting from the mutation forms a trans Watson-Crick pair with U17. The C1'-C1' distance of the U10•U17 base pair of the mutant (11.1 Å) is largely unchanged from that of the A10•U17 pair of the wild-type Mango-III (11.2 Å).

In both structures, N3 of U17 donates a hydrogen to bond with either N3 of the wild type A15 or 02 of U15. The distance of this hydrogen bond decreases from ~2.95 Å in the wild type structure to ~2.7 Å in the A15U mutant. This further reduces the overlap of the nucleotide in position 15 with the methylquinoline. As a result, TO1-Biotin is observed in two distinct conformations in the ASU of the A15U mutant, with two copies found in the E conformation and two copies in the Z conformation (FIG. 48 C). Both TO1-Biotin fluorophores in the wild type structure are in the Z-conformation.

The mutant base pair results in reduced overlap with the ligand. This is consistent with fluorescence binding data showing that the more extended TO3-Biotin fluorophore is disrupted by pyrimidine substitutions in the cap and favored by purine substitutions (FIG. 52). Interestingly, Mango-III and the Mango-III A15U mutant bound to a broad set of TO1 fluorophore derivatives (FIG. 53) in contrast to Mango-I.

Structure Guided Reselection of Mango-III

Given the improved fluorescence enhancement observed in the A22U mutant and the detrimental effects of mutagenesis to T1' and T1, as well as the structurally implied instability of these two regions, we hypothesized that structure guided reselection would improve the fluorescence enhancement and or stability of the Mango-III aptamer. A starting pool of $4.1 \times 10^6$ sequences was generated by mixing two RNA pools in equal proportion, with the first pool (pool 1) randomized at ten positions in the conserved Mango-III core (8, 12, 15, 17, 22, 24, 26, 29, 30, 31) and the second pool (pool 2) randomized at the same positions as pool 1 with an additional random insertion 3' to position 31 to potentially allow for a canonical G-tetrad to form. An engineering work flow was implemented consisting of one round of SELEX*, to enrich high affinity aptamers, followed by seven rounds of IVC to select for bright aptamers. The selection converged on five sequences with frequencies of 58%, 12%, 8.5%, 1.2% and 0.4% (FIG. 50). Identical to the Mango-III-A15U mutant, all five sequences possessed uridines at binding pocket positions 15, 17, and 22 indicating that the rationally designed A15U mutant is optimal for fluorescence enhancement. However, all five sequences contained the insertion 3' to position 31 as well as mutations in the helix-T1 junction, T1, and T1' indicating that the region distal from the binding pocket is indeed suboptimal.

The inter-tier interactions of A21 and G26 appear to be the most stable in P2. This interaction network is observed in all six protamers of our two structures, whereas two protamers in the ASU of Mango-III-A15U show U20, A28, and U29 in an unfolded state. However, even the unfolded conformations in the Mango-III (A15U)-TO1-Biotin complex resolve the pro-RP oxygen of U20 hydrogen bonding to the 02' of G19, suggesting that the nucleotide in the 20 position can promote a stable binding-pocket regardless of base composition. Indeed, mutagenesis of the bases in P2 show that T3' is the most tolerant to nucleotide changes, with TO1-Biotin Kds ranging from 1.6 nM to 9.7 nM. while mutagenesis of P2' and P1' exhibit Kds ranging from 140 nM to 250 nM. Seeing as the A21 residue is adjacent to the cap nucleotide U22, the binding of fluorophore may couple folding of both U22 and A21. These binding data support the importance of A21 and G26 in stabilizing the fluorophore binding pocket and the precarious nature of U29, given its location adjacent to the mixed tetrad, T1.

Methods

Crystallography

RNAs were chemically synthesized (Dharmacon); deprotected according the manufacturers protocol and gel purified. RNAs were exchanged into 20 mM MOPS-KOH pH 7.0, 150 mM KCl and 10 µM EDTA through centrifugal ultrafiltration (3,000-Da cutoff, Millipore); filtered (0.1 µm cutoff, Amicon Ultrafree-MC, Millipore); and stored at 4° C. Some RNAs were in vitro transcribed and purified by electrophoresis on 14% polyacrylamide (19:1 acrylamide/bisacrylamide), 1×TBE, 8M Urea gels; electroeluted from gel slices; washed once with 1M KCl; desalted by ultrafiltration and a partial list appears in FIG. 52.

Crystallization of Mango-III-TO1-Biotin was performed by heating RNA 1 (20 mM MOPS-KOH pH 7.0, 150 mM KCl, 10 µM EDTA) to 95° C. for 3 minutes, placed at 21° C. for 10 minutes, mixed with equimolar concentration of TO1-Bitoin then kept at 21° C. for 30 minutes. For crystallization, 0.2µ of RNA solution (300 µM) and 0.2 µl reservoir solution were mixed and equilibrated against 0.04 M Na Cacodylate pH 6.5, 0.08 M NaCl, 0.012 M KCl, 0.02 M $MgCl_2$, 0.012 M Spermine·4 Cl, 5.5% Sucrose, 31% MPD. Strongly fluorescent (500 nm illumination), tretraganol pyramidal crystals grew in 1-3 days to maximum dimensions of 300×100×100 µm³. Additional cryoprotection was not necessary prior to mounting the crystal in a nylon loop and vitrifying by plunging into liquid nitrogen. Data collection was performed under a cryo-cooled nitrogen stream at APS 22-BM with a beam wavelength of 0.977 Å as well as APS 24-ID-C at 1.495 Å resulting in data sets with a maximum resolution of 2.35 Å. Data were reduced in HKL2000 with 10% of reflections flagged for $R_{Free}$ calculation. Phases were obtained by soaking crystals in drop conditions above supplemented with 10 mM Iridium hexamine for 90 minutes and then vitrifying by plunging into liquid nitrogen. Data sets of iridium soaked crystals were collected at APS 22-ID at a wavelength of 0.957 Å. SHELXC reported a significant anomalous signal extending to 3.5 Å from a single crystal diffracting to 3.2 Å. Two heavy atom sites were located by SHELXD with density modification performed in SHELXE resulting in an uninterpretable map. Sites from SHELXD were loaded into AutoSol resulting in phase solution with a figure of merit of 0.22. The resulting density modified map showed decent density contrast for a helical region allowing for 16 bases to be modeled directly into the SAD map. This model was then refined using Pehnix.refine and molecular replaced into the native data set (2.35 Å resolution) collected at APS 22-BM using the program Phaser, resulting in a TFZ score of 12.1. Manuel building and refinement was performed in Coot and Phenix.refine, respectively, using the HL coefficients generated from the Iridium dataset as a target.

Mango-III-A15U-TO1-Biotin was crystallized by adding 0.2 µl of RNA 2 solution (300 µM, prepared similarly to above with addition of TO1-Biotin) and 0.2 µl reservoir solution were mixed and equilibrated against 1.6 M Ammonium Citrate, 3.0% glycerol and 4% Acetone. Strongly fluorescent, equilateral triangular rod like crystals, grew in 1-2 days with dimensions of 80×(20×20×20) µm. Supplementation of the growth conditions was not necessary for cryoprotection. Crystals were mounted in a nylon loop and vitrifying by plunging into liquid nitrogen. Data were collected at ALS beamline 502 at a wavelength of 1.105 Å. Data were reduced in DIALS with 5% of reflections being flagged for $R_{Free}$ calculation. Phasing was performed by molecular replacement using the program Phaser with coordinates from the Mango-III-TO1 structure from above with residues 1, 2, 15, 22, 37 and 38 deleted along with the TO1 ligand. A replacement solution was found with a TFZ score of 15.2. Multiple rounds of building and refinement were performed in Coot and Phenix.refine respectively. Simulated annealing was performed every 6 refinement cycles at 5000 K until an $R_{Free}$ of 0.25 was reached. A new set of $R_{Free}$ flags composing 10% of reflections was selected and building and refinement continued with 4 rounds of simulated annealing.

Analytical Ultracentrifugation

Analytical Ultracentrifugation was performed on RNA 1 in the presence and absence of TO1-Biotin. Cells contained RNA Mango at 5 µM concentration in addition to 20 mM MOPS-KOH, pH 7.0, 150 mM KCl, 10 µM EDTA. Samples were prepared as noted above. 500 scans were collected and averaged on a Beckman XLI analytical ultracentrifuge. Absorbance was measured at 295 nm, under constant velocity with a run speed of 60,000 r.p.m. at 20° C. The viscosity and density of the buffer were calculated to be 0.01015 P and 1.0068 g ml⁻¹, respectively, with the Sednterp server (http://rasmb.org/sednterp).

Fluorescence Binding Experiments

RNA Preparation

RNAs 3-10 were in vitro transcribed via run off transcription with oligonucleotides purchased from IDT and purified by electrophoresis on 10% polyacrylamide (19:1 acrylamide/bisacrylamide), 1×TBE, 8M Urea gels; electroeluted from gel slices; washed once with 1M KCl; desalted by ultrafiltration. RNA concentrations were determined by reading the Absorbance at 260 nm on a NanoDrop Spectrophotometer (ThermoFisher Scientific), and using the extinction coefficients determined with the nearest neighbor method using the IDT OligoAnalyzer online tool.

Binding Affinity Measurements

Fluorescence readings were recorded using a Varian Cary Eclipse Spectrophotometer set to measure at the maximum excitation and emission wavelengths of the Mango II aptamer dye complex. Fluorescence titrations were performed in Mango selection buffer (WB: 140 mM KCl, 1 mM $MgCl_2$, 10 mM $NaH_2PO_4$ pH 7.2, 0.05% Tween-20). To determine binding affinity and Fmax, curves were fitted using least squares (Kaleidagraph 4.5) using the following equation for TO1-Biotin:

$$F = F_0 + \frac{F_{max}}{2}\left(K_D + [RNA] + [TO] - \sqrt{([RNA] - [TO])^2 + K_D(K_D + 2[RNA] + 2[TO])}\right)$$

Or to the following equation for TO3-Biotin:

$$F = F_0 + \frac{F_{max}[RNA]}{K_D + [RNA]}$$

Fluorescence Enhancement Measurements

Fluorescence enhancement experiments were performed on a Photon Technologies International/820 Photomultiplier Detection System with an excitation and emission wavelength centered at 510 nm and 535 nm, respectively, for TO1-Biotin and TO1 derivatives while TO3-Biotin excitation and emission were 635 nm and 660 nm, respectively.

The bandwidth for all measurements was 1.5 nm for all experiments. Measurements were performed in a 0.2 cm path length cuvette in a background of 20 mM MOPS pH 7.0, 150 mM KCl, 10 µM EDTA. Fluorescence readings were taken in the absence of RNA at a ligand concentration of 0.82 µM. A concentrated, annealed stock of RNA was then added to the cuvette resulting in a final concentration of 2 µM RNA and allowed to equilibrate for 1 minute prior to taking an emission reading. Fluorescence enhancement was determined by dividing the fluorescence signal of ligand in the presence of RNA by the fluorescence signal in the absence of RNA corrected for the background of the instrument.

Fluorescence Lifetime Measurements

Fluorophore lifetime measurements were performed by using an in-house modified 2-photon fluorescence microscope based on a Zeiss LSM 510 unit capable of Time-Correlated Single-Photon Counting (TCSPC) measurements. A diode-pumped solid state laser (Millenia Prime, Spectra Physics, Newport, Calif.) was used to pump a Ti:Sapphire Tsunami oscillator (Model 3960C, Spectra Physics, Newport, Calif.), operating in femtosecond mode, at a repetition rate of 80 MHz, and tunable in the near infrared region. The output beam of the Ti:Sapphire laser was directed into an acousto-opto modulator (MT110/B50/A1.5 IR/S, AA Optoelectronic, France), controlled through the Zeiss LSM electronics and software, to attenuate the power before steering it into the LSM unit. The beam was reflected onto a 700/488 dichroic mirror and directed into the back aperture of a Plan Apochromat 63×, NA 1.4, oil immersion objective, and expanded to fill the back pupil. The fluorescence from the sample was collected from the same objective, intercepted by a 733LP dichroic mirror, sent toward the back port of the microscope, filtered through an ET700SP-2P filter (Chroma Technologies, Bellows Falls, Vt.) to remove residual scattering from the laser, and further passed through a 540/50 nm bandpass filter (Semrock, Rochester, N.Y.). The fluorescence is finally focused onto the photocathode of a H7422P-40 GaAsP photomultiplier detector (Hamamatsu, Japan). The large NA of the objective contributes to a certain degree of depolarization of the incoming excitation beam, as well as of the detected fluorescence. According to Fisz (J. Chem. Phys. A, 2007 and 2009), this would allow one to omit an analyzer (polarizer) in front of our detector, because magic angle conditions are achieved by using a 45° angle detection (i.e. unpolarized) configuration. The signal from the detector and the synchronization signal from the laser are directed into an SPC150 photon counting card (Becker & Hickl, Germany), controlled by the SPCM64 proprietary software from the manufacturer (Becker & Hickl, Germany). The data were collected with a 12.5 ns time window in TCSPC histogramming mode with 1024 channels, with a width of 12.2 ps each.

For the experiments the laser was tuned at 780 nm, and the power adjusted to 18 mW before the objective lens. RNA samples were diluted to a concentration of ~3-5 µM in buffer. TO-1B was measured at a concentration of 50 µM due to low fluorescence signal of the compound, compared to the RNA-bound version. An 80 µl droplet was deposited onto a #1.5 coverslip, previously treated with BSA to avoid nonspecific binding of RNA to the glass, and covered to avoid evaporation. The excitation was focused ~5 µm above the upper surface of the coverslip to reduce scatter and to avoid collecting signal from molecules immobilized on the glass surface. The beam was kept stationary by using the LSM controller to simply open the excitation shutter, and data were collected until the maximum count in the peak channel of the TCSPC histogram reached $10^4$ photons. Experiments were repeated in triplicate. An instrument response function (IRF) was collected on every day of measurement by recording the second harmonic generation (SHG) signal from crushed urea crystals deposited onto a glass coverslip, in this case the bandpass filter before the detector was substituted with a 440 nm short pass filter to collect the 390 nm SHG. The data collected with the SPCM64 software were stored as *.sdt files for subsequent analysis.

Fluorescence Lifetime Data Analysis

Data were analyzed using the SPCImage software (Becker & Hickl, Germany). The fluorescence decay curves were fit using exponential functions of the form:

$$I(t) = \sum_{i=1}^{n} a_i e^{-t/\tau_i}$$

Where n is at most equal to 3 in our software. The data fitting routine uses a least-square algorithm where the exponential function is first reconvoluted with the measured IRF and then fit to the data. The shift of the IRF for each dataset, as well as a scatter contribution were included as free parameters during fitting. The number of exponentials used to fit the data was adapted in order to minimize the $\chi^2$ value, which together with the randomness of the residuals was used to evaluate the goodness of the fit.

REFERENCES

1. Otwinski, Z. & Minor, W. Processing of X-ray diffraction data collected in oscillation mode. *Methods Enzymol.* 276, 307-326
2. Kabsch, W. XDS. Acta Cryst. D Biol Crystallogr 66, 125-132 (2010)
3. McCoy, A. J. et al. Phaser crystallographic software. *J. Appl. Cryst.* 40, 658-674 (2007)
4. Emsley, P., Lohkamp, B., Scott, W. G. & Cowtan, K. Features and development of Coot. Acta Crystallogr. *D Biol. Crystallogr.* 66, 486-501
5. Adams, P. D. et al. PHENIX: a comprehensive Python-based system for macromolecular structure solution. Acta Crystallogr. D Biol Crystallogr. 66, 213-221 (2010)

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US11434490B2). An electronic copy of the "Sequence Listing" will also be available from the USPTO upon request and payment of the fee set forth in 37 CFR 1.19(b)(3).

The invention claimed is:
1. A RNA aptamer comprising an active core sequence as set forth in:

(SEQ ID NO: 2)
5'- GG@(T$_1$/WGW)GG(#$_1$H/WG)WGGN@(#$_2$/-)G(T$_2$/H)GNH
(AN@T$_3$/G)-3' with the proviso that the active core sequence is not the sequence as set forth in SEQ ID NO: 1: GAAGGGACG-GUGCGGAGAGGAGA
wherein, within the active core sequence:
  represents no nucleotide (gap);
  K represents U or G;
  S represents C or G;
  R represents A or G;
  W represents A or U;
  H represents A, C or U;
  N represents A, C, G or U; and
  @ represents N or a deletion;
and wherein T$_1$ represents any nucleotide, T$_2$ and T$_3$ being defined as follows:
when T$_1$ is A, T$_2$ can be either A, G or U; and
  when T$_1$ is A and T$_2$ is A, then T$_3$ is U;
  when T$_1$ is A and T$_2$ is G, then T$_3$ is U; and
  when T$_1$ is A and T$_2$ is U, then T$_3$ is A or U; or
when T$_1$ is C, T$_2$ can be either G or U; and
  when T$_1$ is C and T$_2$ is G, then T$_3$ is C or G; and
  when T$_1$ is C and T$_2$ is U, then T$_3$ is G; or
when T$_1$ is G, T$_2$ can be either G or C, and T$_3$ is C; or
when T$_1$ is U, T$_2$ can be either A or C; and
  when T$_1$ is U and T$_2$ is A, then T$_3$ is A or U; and
  when T$_1$ is U and T$_2$ is C, then T$_3$ is A;
  wherein #$_1$ and #$_2$ represents any nucleotide pair such that
    when #$_1$ is A, then #$_2$ represents A, C, G or U; or
    when #$_1$ is C, then #$_2$ is C; or
    when #$_1$ is G, then #$_2$ is G; or
    when #$_1$ is U, then #$_2$ represents A, G or U;
wherein the aptamer adopts a determined tridimensional conformation which is a fluorophore binding conformation, said aptamer when it adopts the fluorophore binding conformation being liable interact with a fluorophore;
wherein the aptamer further comprises, contiguous with the active core sequence, a 5' leader sequence attached, or operably linked to (by covalent bound, i.e. phosphodiester bound), to the 5' terminus of the active core and a 3' tail sequence attached, or operably linked to (by covalent bridge mentioned below), to the 3' terminus of the active core, and wherein the 5' leader sequence and the 3' tail sequence together mediate the juxtaposition of the 5' terminus of the active core and the 3' terminus of the active core when the aptamer is the fluorophore binding conformation.

2. The aptamer according to claim 1, wherein said aptamer can interact with a fluorophore, said fluorophore being selected from group consisting of the following compounds of the following Formula I and Formula II:

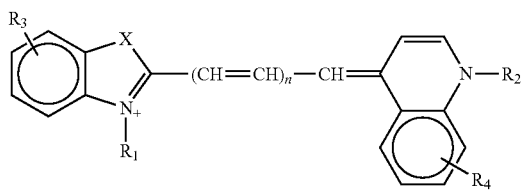

(I)

wherein:
  X represents O, S, Se, or C(CH$_3$)$_n$;
  R$_1$ represents an alkyl having from 1-6 carbons;
  R$_2$ represents an alkyl having from 1-6 carbons;
  R$_3$ is either a fused benzene, an alkyl having 1-6 carbons, a methoxy or H;
  R$_4$ is an alkyl having 1-6 carbons, a methoxy or H; and
  n=zero or an integer from 1-6;

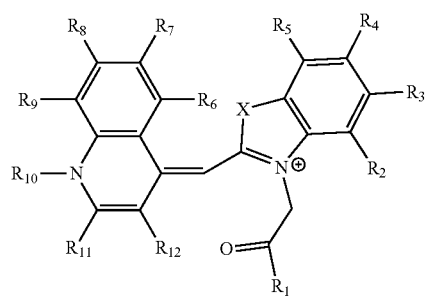

(II)

wherein:
  R$_1$ represents any substituent;
  R$_2$ through R$_5$ represent H, F, Cl, Br, I, CH$_3$, linear polymers, or extended heterocycles
  R$_6$-R$_9$ represent H, F, Cl, Br, I, CH$_3$, linear polymers, or extended heterocycles
  R$_{10}$ represents H, F, Cl, Br, I, CH$_3$, linear polymers, or extended heterocycles,
  R$_{11}$ through R$_{12}$ represent H, F, Cl, Br, I, CH$_3$, linear polymers, or extended heterocycles
  X represents the following atoms O, S and Se; and
  n is 1 or 3 or 5.

3. The aptamer according to claim 1, wherein the core active sequence comprises the following sequence:

(SEQ ID NO: 5)
5'-$\$_1$GGNT$_1$GG#$_1$HUGGHA#$_2$GT$_2$GNHAN@T$_3\$_2$-3' wherein:
H represents A, C or U
N represents A, C, G or U
@ represents any nucleotide or no nucleotide
$_1$ and #$_2$ represents any nucleotide pair such that
  when #$_1$ is A, then #$_2$ represents A, C, G or U; or
  when #$_1$ is C, then #$_2$ is C; or
  When #$_1$ is G, then #$_2$ is G; or
  when #$_1$ is U, then #$_2$ represents A, G or U,
$\$_1$ and $\$_2$ represent any pair of nucleotides such that
when $\$_1$ is A, then $\$_2$ is A, G or U; or
when $\$_1$ is C, then $\$_2$ is A, G or U; or
when $\$_1$ is G, then $\$_2$ is A, C, G or U; or
when $\$_1$ is U, then $\$_2$ is A, G.

4. The RNA aptamer according to claim 1, wherein the core active sequence comprises the following sequence:

(SEQ ID NO: 6)
GG@WGWGGWGWGGN@GHGGHG wherein:
W represents A or U;
H represents A, C or U;
N represents A, C, G or U; and
@ represents N or a no nucleotide.

5. The RNA aptamer according to claim 1, wherein the core active sequence comprises the following sequence:

$$\text{GAA(GG)}_1\text{AA(GG)}_2\text{NUU(GG)}_3\text{UAN'G}_{4i}\text{UG}_{4ii}\text{GUAUAUUC} \quad \text{(SEQ ID NO: 7)}$$

wherein:
N is any nucleotide, N' the anti-watson crick partner to N wherein $(GG)_1$, $(GG)_2$, $(GG)_3$ and $G_{4i}$ and $G_{4ii}$ form a quadruplex structure when the active core is in the fluorophore binding conformation, with the 5' terminus of the active core being juxtaposed to the 3' terminus of the active core.

6. The RNA aptamer according to claim 1, wherein the core active sequence comprises the following sequence:

$$\text{[G/C]NR(GG)}_1\text{[R/D]AG[A/U](GG)}_2\text{NGN(GG)}_3\text{A*[A/U/D]GA*} \quad \text{(SEQ ID NO: 8)}$$
$$\text{(GG)}_4\text{[A/C]R[A/D]}$$

wherein:
A* is A or N,
N is any nucleotide
R is a purine,
D denotes the absence of nucleotide,
wherein $(GG)_1$, $(GG)_2$, $(GG)_3$ and $(GG)_4$ form a quadruplex structure when the active core is in the fluorophore binding conformation, with the 5' terminus of the active core being juxtaposed to the 3' terminus of the active core.

7. The RNA aptamer according to claim 1, wherein the core active sequences comprises one of the sequences as set forth in SEQ ID NO: 7 to SEQ ID NO: 6887.

8. The RNA aptamer comprising a core active sequence as defined in claim 1, with the proviso that said aptamer active core does not have the core sequence: GNR(GG)$_1$GNN (GG)$_2$NGN(GG)$_3$AGN(GG)$_4$AGA SEQ ID NO: 6888, wherein R is a purine, and N is any nucleotide.

9. The RNA aptamer according to claim 1, wherein the 5' leader sequence and the 3' tail sequence are complementary, so that binding of the 5' leader sequence to the 3' tail sequence mediates the juxtaposition of the 5' terminus of the active core and the 3' terminus of the active core when the aptamer is the fluorophore binding conformation.

10. The RNA aptamer according to claim 1, wherein the 5' leader sequence and the 3' tail sequence are complementary to a target sequence, the target sequence comprising:
a leader bait sequence that is complementary to the 3' tail sequence of the aptamer; and,
a tail bait sequence that is complementary to the 5' leader sequence of the aptamer;
the leader and tail bait sequences being juxtaposed in the target sequence, so that binding of:
the 5' leader sequence to the tail bait sequence; combined with,
binding of the 3' tail sequence to the leader bait sequence;
mediates the juxtaposition of the 5' terminus of the active core and the 3' terminus of the active core when the aptamer is the fluorophore binding conformation.

11. The RNA aptamer according to claim 1, wherein the leader and tail bait sequences being contiguous in the target sequence.

12. The RNA aptamer according to claim 1, wherein juxtaposition of the 5' terminus of the active core and the 3' terminus of the active core when the aptamer is the fluorophore binding conformation brings a phosphate group from the 5' terminus to within 10 Å, or to within 9 Å or to within 8 Å, of a phosphate group from the 3' terminus.

13. The RNA aptamer according to claim 1, wherein the aptamer has a fluorophore binding affinity of at least 400 nM, 300 nM, 200 nM, 100 nM, 50 nM, 40 nM, 30 nM, 20 nM, 10 nM, 5 nM, 1 nM or 0.5 nM when the core is in a fluorophore binding conformation.

14. The RNA aptamer according to claim 1, wherein the fluorophore-aptamer complex has a brightness of at least 7,000 $M^1$ $cm^{-1}$, 8,000 $M^{-1}cm^{-1}$, 9,000 $M^{-1}cm^{-1}$, 10,000 $M^{-1}$ $cm^{-1}$, 43,000 $M^{-1}cm^{-1}$.

15. The RNA aptamer according to claim 1, wherein the fluorophore-aptamer complex has a fluorescent lifetime of at least 1 ns, or at least 2 ns, or at least 3 ns, or at least 4 ns or at least 5 ns, or at least 6 ns, or in the range of 1-6 ns.

16. The RNA aptamer according to claim 1, wherein the fluorophore-aptamer complex is fluorescent in a formaldehyde solution.

17. The RNA aptamer according to claim 1, wherein the secondary aptamer sequence has affinity for a secondary target moiety.

* * * * *